(12) United States Patent
Stowell Laurence et al.

(10) Patent No.: US 9,187,735 B2
(45) Date of Patent: Nov. 17, 2015

(54) METAL ABSTRACTION PEPTIDE WITH SUPEROXIDE DISMUTASE ACTIVITY

(71) Applicants: University of Kansas, Lawrence, KS (US); Echogen, Inc., Lenexa, KS (US)

(72) Inventors: Jennifer Ann Stowell Laurence, Lawrence, KS (US); Mary Elizabeth Krause, Lawrence, KS (US); Timothy A. Jackson, Lawrence, KS (US); Amanda Michelle Glass, Overton (NE); George Laurence, Lawrence, KS (US)

(73) Assignees: UNIVERSITY OF KANSAS, Lawrence, KS (US); ECHOGEN, INC., Lawrence, KS (US)

( * ) Notice: Subject to any disclaimer, the term of this patent is extended or adjusted under 35 U.S.C. 154(b) by 0 days.

(21) Appl. No.: 13/905,457

(22) Filed: May 30, 2013

(65) Prior Publication Data

US 2013/0330314 A1 Dec. 12, 2013

Related U.S. Application Data

(60) Provisional application No. 61/654,547, filed on Jun. 1, 2012.

(51) Int. Cl.
| | | |
|---|---|---|
| C12N 9/02 | (2006.01) | |
| C12P 7/62 | (2006.01) | |
| C07K 14/62 | (2006.01) | |
| A61K 38/00 | (2006.01) | |

(52) U.S. Cl.
CPC .............. *C12N 9/0089* (2013.01); *C07K 14/62* (2013.01); *C12P 7/62* (2013.01); *C12Y 115/01001* (2013.01); *A61K 38/00* (2013.01)

(58) Field of Classification Search
None
See application file for complete search history.

(56) References Cited

U.S. PATENT DOCUMENTS

| | | |
|---|---|---|
| 4,569,794 A | 2/1986 | Smith et al. |
| 4,582,907 A | 4/1986 | Campbell |
| 4,732,864 A | 3/1988 | Tolman |
| 5,102,990 A | 4/1992 | Rhodes |
| 5,137,819 A | 8/1992 | Kilburn et al. |
| 5,202,247 A | 4/1993 | Kilburn et al. |
| 5,225,180 A | 7/1993 | Dean et al. |
| 5,340,731 A | 8/1994 | Kilburn et al. |
| 5,443,815 A | 8/1995 | Dean et al. |
| 5,443,816 A | 8/1995 | Zamora et al. |
| 5,464,823 A | 11/1995 | Lehrer et al. |
| 5,496,714 A | 3/1996 | Comb et al. |
| 5,496,934 A | 3/1996 | Shoseyov et al. |
| 5,646,016 A | 7/1997 | Mccoy et al. |
| 5,654,272 A | 8/1997 | Dean |
| 5,656,591 A | 8/1997 | Tomita et al. |
| 5,679,548 A | 10/1997 | Barbas |
| 5,700,444 A | 12/1997 | Zamora et al. |
| 5,750,081 A | 5/1998 | Smart |
| 5,759,516 A | 6/1998 | Zamora et al. |
| 5,785,948 A | 7/1998 | Itaya et al. |
| 5,789,555 A | 8/1998 | Pollak et al. |
| 5,834,247 A | 11/1998 | Comb et al. |
| 5,837,814 A | 11/1998 | Shoseyov et al. |
| 5,879,659 A | 3/1999 | Edwards et al. |
| 5,891,418 A | 4/1999 | Sharma |
| 5,951,964 A | 9/1999 | Dean et al. |
| 5,994,339 A | 11/1999 | Crapo et al. |
| 5,997,844 A | 12/1999 | Dean et al. |
| 6,057,367 A | 5/2000 | Stamler et al. |
| 6,074,627 A | 6/2000 | Dean et al. |
| 6,127,356 A | 10/2000 | Crapo et al. |
| 6,143,524 A | 11/2000 | Mccoy et al. |
| 6,180,824 B1 | 1/2001 | Stamler et al. |
| 6,228,373 B1 | 5/2001 | Bergstrand et al. |
| 6,248,304 B1 | 6/2001 | Lister-James et al. |
| 6,261,536 B1 | 7/2001 | Zamora et al. |
| 6,270,765 B1 | 8/2001 | Deo et al. |
| 6,274,552 B1 | 8/2001 | Tamarkin et al. |
| 6,291,247 B1 | 9/2001 | Riopelle et al. |
| 6,319,401 B1 | 11/2001 | Josic et al. |
| 6,331,285 B1 | 12/2001 | Sharma |
| 6,338,834 B1 | 1/2002 | Jurisson et al. |
| 6,359,004 B1 | 3/2002 | Stamler et al. |
| 6,365,161 B1 | 4/2002 | Deo et al. |
| 6,395,272 B1 | 5/2002 | Deo et al. |
| 6,407,208 B1 | 6/2002 | Chen et al. |
| 6,410,690 B1 | 6/2002 | Deo et al. |
| 6,537,520 B1 | 3/2003 | Rajopadhye et al. |
| 6,607,709 B1 | 8/2003 | Jurisson et al. |
| 6,608,110 B2 | 8/2003 | Stamler et al. |
| 6,632,922 B1 | 10/2003 | Deming et al. |
| 6,653,442 B1 | 11/2003 | Chang et al. |
| 6,664,305 B2 | 12/2003 | Jungbauer et al. |
| 6,667,389 B1 | 12/2003 | Dean et al. |

(Continued)

FOREIGN PATENT DOCUMENTS

| | | | |
|---|---|---|---|
| CA | 2322795 A1 | 9/1999 | |
| CA | 2329144 A1 | 11/1999 | |

(Continued)

OTHER PUBLICATIONS

Krause et al. Inorganic Chemistry. 2010, 49, 362-463.*
Salvemini et al. Nature Reviews. vol. 1, May 2002, 367-374.*
Office action dated Jan. 15, 2013 for U.S. Appl. No. 13/305,247.
Office action dated Oct. 10, 2013 for U.S. Appl. No. 13/305,247.
Aoki, et al. Cell labeling for magnetic resonance imaging with the T1 agent manganese chloride. NMR Biomed. Feb. 2006;19(1):50-9.

(Continued)

*Primary Examiner* — Amber D Steele
*Assistant Examiner* — Schuyler Milton
(74) *Attorney, Agent, or Firm* — Wilson Sonsini Goodrich & Rosati

(57) ABSTRACT

Compositions comprising peptides that are capable of binding a metal are disclosed. Such compositions can be used for binding metal in a variety of contexts and environments. In various embodiments, peptides are used for antioxidant activity, anti-inflammatory activity, anti-pain therapy, as chemical reagents, and/or as superoxide dismutase mimics.

78 Claims, 31 Drawing Sheets

(56) References Cited

U.S. PATENT DOCUMENTS

| | | |
|---|---|---|
| 6,680,045 B2 | 1/2004 | Jurisson et al. |
| 6,680,365 B1 | 1/2004 | Deming |
| 6,685,912 B2 | 2/2004 | Zamora et al. |
| 6,686,446 B2 | 2/2004 | Deming et al. |
| 6,723,893 B1 | 4/2004 | Brown et al. |
| 6,736,973 B1 | 5/2004 | Podgornik et al. |
| 6,770,455 B1 | 8/2004 | Kiesewetter et al. |
| 7,022,737 B2 | 4/2006 | Stamler et al. |
| 7,033,520 B2 | 4/2006 | Kappel et al. |
| 7,052,673 B2 | 5/2006 | Rajopadhye et al. |
| 7,135,605 B2 | 11/2006 | Acey et al. |
| 7,208,138 B2 | 4/2007 | Haroon et al. |
| 7,238,340 B1 | 7/2007 | Mcbride et al. |
| 7,321,045 B2 | 1/2008 | Rajopadhye et al. |
| 7,329,727 B2 | 2/2008 | Deming |
| 7,332,149 B1 | 2/2008 | Rajopadhye et al. |
| 7,396,814 B2 | 7/2008 | Sharma et al. |
| 7,470,677 B2 | 12/2008 | Crapo et al. |
| 7,592,304 B2 | 9/2009 | Bar-or |
| 7,605,123 B2 | 10/2009 | Radhakrishnan et al. |
| 7,632,803 B2 | 12/2009 | Bar-or |
| 7,741,053 B2 | 6/2010 | Mehigh et al. |
| 7,790,167 B2 | 9/2010 | Tamarkin et al. |
| 7,799,561 B2 | 9/2010 | Hernan et al. |
| 7,807,678 B2 | 10/2010 | Sharma et al. |
| 7,872,095 B2 | 1/2011 | Radhakrishnan et al. |
| 7,875,700 B2 | 1/2011 | Radhakrishnan et al. |
| 7,968,519 B2 | 6/2011 | Deming et al. |
| 7,968,548 B2 | 6/2011 | Sharma et al. |
| 7,973,008 B2 | 7/2011 | Bar-or |
| 8,017,728 B2 | 9/2011 | Bar-or et al. |
| 8,110,402 B2 | 2/2012 | Laurence et al. |
| 8,137,989 B2 | 3/2012 | Tamarkin et al. |
| 8,252,595 B2 | 8/2012 | Stowell et al. |
| 8,263,548 B2 | 9/2012 | Bar-or |
| 8,278,111 B2 | 10/2012 | Laurence et al. |
| 2001/0038822 A1 | 11/2001 | Jurisson et al. |
| 2002/0061599 A1 | 5/2002 | Elling et al. |
| 2003/0035774 A1 | 2/2003 | Adjei et al. |
| 2003/0055003 A1 | 3/2003 | Bar-or et al. |
| 2003/0060408 A1 | 3/2003 | Bar-or et al. |
| 2003/0096870 A1 | 5/2003 | Stamler et al. |
| 2003/0130185 A1 | 7/2003 | Bar-or et al. |
| 2003/0207815 A1 | 11/2003 | Stamler et al. |
| 2004/0002081 A1 | 1/2004 | Urthaler et al. |
| 2004/0018974 A1 | 1/2004 | Arbogast et al. |
| 2004/0109853 A1 | 6/2004 | McDaniel |
| 2004/0234497 A1 | 11/2004 | Luo et al. |
| 2004/0265908 A1 | 12/2004 | Acey et al. |
| 2005/0002861 A1 | 1/2005 | Krause et al. |
| 2005/0112607 A1 | 5/2005 | Bamdad et al. |
| 2005/0123507 A1 | 6/2005 | Ameri et al. |
| 2005/0148101 A1 | 7/2005 | Bamdad et al. |
| 2005/0226813 A1 | 10/2005 | Bonasera et al. |
| 2006/0115514 A1 | 6/2006 | Gengrinovitch |
| 2008/0015224 A1* | 1/2008 | Wilcox ............ 514/315 |
| 2009/0136594 A1 | 5/2009 | McLeroy et al. |
| 2009/0208412 A1 | 8/2009 | Lovhaug et al. |
| 2010/0213411 A1 | 8/2010 | Hosoya |
| 2010/0221305 A1 | 9/2010 | Armeri et al. |
| 2010/0221839 A1* | 9/2010 | Laurence et al. ............ 436/73 |
| 2011/0097742 A1 | 4/2011 | Yang et al. |
| 2011/0124553 A1 | 5/2011 | Radhakrishnan et al. |
| 2011/0212902 A1 | 9/2011 | Bar-or |
| 2011/0212903 A1 | 9/2011 | Bar-or |
| 2012/0040915 A1 | 2/2012 | Mukhopadhyay et al. |
| 2012/0088848 A1 | 4/2012 | Deming et al. |
| 2012/0174712 A1 | 7/2012 | Laurence et al. |
| 2012/0177579 A1 | 7/2012 | Laurence et al. |
| 2012/0177580 A1 | 7/2012 | Laurence et al. |
| 2012/0177667 A1 | 7/2012 | Laurence et al. |
| 2012/0329987 A1 | 12/2012 | Laurence et al. |
| 2013/0018172 A1 | 1/2013 | Laurence et al. |
| 2014/0135484 A1 | 5/2014 | Stowell et al. |

FOREIGN PATENT DOCUMENTS

| | | |
|---|---|---|
| EP | 0295826 A1 | 12/1988 |
| EP | 0184355 B1 | 1/1992 |
| EP | 0629347 B1 | 7/1997 |
| EP | 0711305 B1 | 11/2001 |
| EP | 0665853 B1 | 8/2002 |
| EP | 0871654 B1 | 4/2003 |
| EP | 0719790 B1 | 7/2003 |
| EP | 0888130 B1 | 7/2003 |
| EP | 1437145 A1 | 7/2004 |
| EP | 0602899 B1 | 10/2004 |
| EP | 0723398 B1 | 3/2005 |
| EP | 1068224 B1 | 5/2005 |
| EP | 0831891 B1 | 10/2005 |
| EP | 0963219 B1 | 11/2005 |
| EP | 0827412 B1 | 1/2006 |
| EP | 1044022 B1 | 3/2006 |
| EP | 0637968 B2 | 7/2006 |
| EP | 1212366 B1 | 9/2007 |
| EP | 1231217 B1 | 1/2010 |
| EP | 2320231 A2 | 5/2011 |
| EP | 1220870 B1 | 4/2012 |
| EP | 2320231 A3 | 7/2012 |
| WO | WO 87/04622 A1 | 8/1987 |
| WO | WO 92/18166 A1 | 10/1992 |
| WO | WO 93/14640 A1 | 8/1993 |
| WO | WO 94/19493 A1 | 9/1994 |
| WO | WO 95/04753 A1 | 2/1995 |
| WO | WO 95/10185 A1 | 4/1995 |
| WO | WO 95/13832 A1 | 5/1995 |
| WO | WO 96/30397 A1 | 10/1996 |
| WO | WO 96/40223 A1 | 12/1996 |
| WO | WO 96/40789 A1 | 12/1996 |
| WO | WO 97/06824 A2 | 2/1997 |
| WO | WO 97/18826 A1 | 5/1997 |
| WO | WO 97/18827 A1 | 5/1997 |
| WO | WO 97/06824 A3 | 7/1997 |
| WO | WO 97/33627 A2 | 9/1997 |
| WO | WO 97/33877 A1 | 9/1997 |
| WO | WO 97/33627 A3 | 2/1998 |
| WO | WO 98/33808 A2 | 8/1998 |
| WO | WO 98/33808 A3 | 2/1999 |
| WO | WO 99/47561 A1 | 9/1999 |
| WO | WO 99/57992 A1 | 11/1999 |
| WO | WO 99/60134 A1 | 11/1999 |
| WO | WO 00/43791 A2 | 7/2000 |
| WO | WO 01/25265 A1 | 4/2001 |
| WO | WO 00/43791 A3 | 7/2001 |
| WO | WO 01/50127 A2 | 7/2001 |
| WO | WO 01/50127 A3 | 1/2002 |
| WO | WO 02/01230 A2 | 1/2002 |
| WO | WO 02/01230 A3 | 8/2003 |
| WO | WO 2004/000204 A2 | 12/2003 |
| WO | WO 2004/060409 A1 | 7/2004 |
| WO | WO 2004/106361 A2 | 12/2004 |
| WO | WO 2005/004842 A2 | 1/2005 |
| WO | WO 2004/000204 A3 | 3/2005 |
| WO | WO 2005/004842 A3 | 4/2005 |
| WO | WO 2006/014673 A2 | 2/2006 |
| WO | WO 2006/054904 A2 | 5/2006 |
| WO | WO 2006/056984 A2 | 6/2006 |
| WO | WO 2006/014673 A3 | 8/2006 |
| WO | WO 2006/056984 A3 | 10/2006 |
| WO | WO 2006/054904 A3 | 4/2007 |
| WO | WO 2004/106361 A3 | 11/2007 |
| WO | WO 2009/140408 A2 | 11/2009 |
| WO | WO 2009/146099 A2 | 12/2009 |
| WO | WO 2009/140408 A3 | 1/2010 |
| WO | WO 2009/146099 A3 | 2/2010 |

OTHER PUBLICATIONS

Bachran, et al. A lysine-free mutant of epidermal growth factor as targeting moiety of a targeted toxin. Life Sci. Jan. 31, 2011;88(5-6):226-32. doi: 10.1016/j.lfs.2010.11.012. Epub Nov. 19, 2010.

Boswell, et al. Impact of Drug Conjugation on Pharmacokinetics and Tissue Distribution of Anti-STEAP1 Antibody-Drug Conjugates in

(56) References Cited

OTHER PUBLICATIONS

Rats. Bioconjug Chem. Oct. 19, 2011;22(10):1994-2004. doi: 10.1021/bc200212a. Epub Oct. 3, 2011.
Breeman, et al. Radiolabelled regulatory peptides for imaging and therapy. Anticancer Agents Med Chem. May 2007;7(3):345-57.
Bremner, et al. Effects of changes in dietary zinc, copper and selenium supply and of endotoxin administration on metallothionein I concentrations in blood cells and urine in the rat. J Nutr. Sep. 1987;117(9):1595-602.
Chang, et al. A major kinetic trap for the oxidative folding of human epidermal growth factor. J Biol Chem. Feb. 16, 2001;276(7):4845-52. Epub Nov. 21, 2000.
Chang, et al. The disulfide folding pathway of human epidermal growth factor. J Biol Chem. Apr. 21, 1995;270(16):9207-16.
Chen, et al. Pegylated Arg-Gly-Asp peptide: 64Cu labeling and PET imaging of brain tumor alphavbeta3-integrin expression. J Nucl Med. Oct. 2004;45(10):1776-83.
Ciaccio, et al. High-yield expression in *E. coli* and refolding of the bZIP domain of activating transcription factor 5. Protein Expr Purif Dec. 2008;62(2):235-43. doi: 10.1016/j.pep.2008.07.011. Epub Aug. 3, 2008.
Crapo, et al. Preparation and assay of superoxide dismutases. Methods Enzymol. 1978;53:382-93.
De Leon-Rodriguez, et al. The synthesis and chelation chemistry of DOTA-peptide conjugates. Bioconjug Chem. Feb. 2008;19(2):391-402. Epub Dec. 12, 2007.
Delaglio, et al. NMRPipe: a multidimensional spectral processing system based on UNIX pipes. J Biomol NMR. Nov. 1995;6(3):277-93.
Di Bartolo, et al. New 64Cu PET imaging agents for personalised medicine and drug development using the hexa-aza cage, SarAr. Org Biomol Chem. Sep. 7, 2006;4(17):3350-7. Epub Jul. 19, 2006.
Franz, et al. Lanthanide-binding tags as versatile protein coexpression probes. Chembiochem. Apr. 4, 2003;4(4):265-71.
Gill, et al. Increased phosphotyrosine content and inhibition of proliferation in EGF-treated A431 cells. Nature. Sep. 24, 1981;293(5830):305-7.
Goddard, T. D., Kneller, D. G. (2004) Sparky. San Francisco: University of California. Revised May 30, 2008.
Goethals, et al. 55Co-EDTA for renal imaging using positron emission tomography (PET): a feasibility study. Nucl Med Biol. Jan. 2000;27(1):77-81.
Gracia, et al. Lead toxicity and chelation therapy. Am J Health Syst Pharm. Jan. 1, 2007;64(1):45-53.
Hammarstrom, et al. Rapid screening for improved solubility of small human proteins produced as fusion proteins in *Escherichia coli*. Protein Sci. Feb. 2002;11(2):313-21.
Huang, et al. The NMR solution structure of human epidermal growth factor (hEGF) at physiological pH and its interactions with suramin. Biochem Biophys Res Commun. Nov. 26, 2010;402(4):705-10. doi: 10.1016/j.bbrc.2010.10.089. Epub Oct. 26, 2010.
International search report and written opinion dated Jan. 10, 2014 for PCT/US2013/043467.
Jansen, et al. Co-registration of PET and MRI in different courses of MS using Cobalt-55 as a Calcium-tracer. Acta Neurol Belg. Sep. 1997;97(3):178-82.
Junutula, et al. Site-specific conjugation of a cytotoxic drug to an antibody improves the therapeutic index. Nat Biotechnol. Aug. 2008;26(8):925-32. doi: 10.1038/nbt.1480. Epub Jul. 20, 2008.
Knor, et al. Synthesis of novel 1,4,7,10-tetraazacyclodecane-1,4,7,10-tetraacetic acid (DOTA) derivatives for chemoselective attachment to unprotected polyfunctionalized compounds. Chem.—Eur. J. 2007; 13:6082-6090.
Le, et al. *Escherichia coli* expression and refolding of E/K-coil-tagged EGF generates fully bioactive EGF for diverse applications. Protein Expr Purif Apr. 2009;64(2):108-17. doi: 10.1016/j.pep.2008. 11.005. Epub Nov. 25, 2008.

Lee, et al. Scale-up process for expression and renaturation of recombinant human epidermal growth factor from *Escherichia coli* inclusion bodies. Biotechnol Appl Biochem. Jun. 2000;31 ( Pt 3):245-8.
Lewis Philips, et al. Targeting HER2-positive breast cancer with trastuzumab-DM1, an antibody-cytotoxic drug conjugate. Cancer Res. Nov. 15, 2008;68(22):9280-90. doi: 10.1158/0008-5472.CAN-08-1776.
Lewis, et al. A Facile, Water-Soluble Method for Modification of Proteins with DOTA. Use of Elevated Temperature and Optimized pH to Achieve High Specific Activity and High Chelate Stability in Radiolabeled Immunoconjugates. Bioconjugate Chem. 1994 ;5, 565-576.
Lewis, et al. An improved method for conjugating monoclonal antibodies with N-hydroxysulfosuccinimidyl DOTA. Bioconjug Chem. Mar.-Apr. 2001;12(2):320-4.
Lewis, et al. Maleimidocysteineamido-DOTA derivatives: new reagents for radiometal chelate conjugation to antibody sulfhydryl groups undergo pH-dependent cleavage reactions. Bioconjug Chem. Jan.-Feb. 1998;9(1):72-86.
Li, et al. DOTA-D-Tyr(1)-octreotate: a somatostatin analogue for labeling with metal and halogen radionuclides for cancer imaging and therapy. Bioconjug Chem. Jul.-Aug. 2002;13(4):721-8.
Li, et al. Vinyl Sulfone Bifunctional Derivatives of DOTA Allow Sulfhydryl- or Amino-Directed Coupling to Antibodies. Conjugates Retain Immunoreactivity and Have Similar Biodistributions. Bioconjugate Chem. 2002; 13:110-115.
Martin, et al. Double-lanthanide-binding tags: design, photophysical properties, and NMR applications. J Am Chem Soc. Jun. 6, 2007;129(22):7106-13. Epub May 12, 2007.
McQuade, et al. Imaging of melanoma using 64Cu- and 86Y-DOTA-ReCCMSH(Arg11), a cyclized peptide analogue of alpha-MSH. J Med Chem. Apr. 21, 2005;48(8):2985-92.
Nielsen, et al. Toxicokinetics of nickel in mice studied with the gamma-emitting isotope 57Ni. Fundam Appl Toxicol. Aug. 1993;21(2):236-43.
Nitz, et al. Structural origin of the high affinity of a chemically evolved lanthanide-binding peptide. Angew Chem Int Ed Engl. Jul. 12, 2004;43(28):3682-5.
Office action dated Jan. 31, 2014 for U.S. Appl. No. 13/596,281.
Office action dated Feb. 14, 2014 for U.S. Appl. No. 13/429,052.
Office action dated Feb. 24, 2014 for U.S. Appl. No. 13/428,864.
Ogiso, et al. Crystal structure of the complex of human epidermal growth factor and receptor extracellular domains. Cell. Sep. 20, 2002;110(6):775-87.
Perazella, et al. Nephrogenic systemic fibrosis, kidney disease, and gadolinium: is there a link? Clin J Am Soc Nephrol. Mar. 2007;2(2):200-2. Epub Feb. 7, 2007.
Porter, et al. Iron mobilization from hepatocyte monolayer cultures by chelators: the importance of membrane permeability and the iron-binding constant. Blood. Nov. 1988;72(5):1497-503.
Samuni, et al. Multifunctional antioxidant activity of HBED iron chelator. Free Radic Biol Med. Jan. 15, 2001;30(2):170-7.
Schagger, et al. Tricine-SDS-PAGE. Nat Protoc. 2006;1(1):16-22.
Sculimbrene, et al. Lanthanide-binding tags as luminescent probes for studying protein interactions. J Am Chem Soc. Jun. 7, 2006;128(22):7346-52.
Sharma, et al. Recombinant human epidermal growth factor inclusion body solubilization and refolding at large scale using expanded-bed adsorption chromatography from *Escherichia coli*. Protein Expression and Purification. Jul. 2008; 60(1):7-14.
Siao, et al. In vitro binding of heavy metals by an edible biopolymer poly(gamma-glutamic acid). J Agric Food Chem. Jan. 28, 2009;57(2):777-84. doi: 10.1021/jf803006r.
Tabbi, et al. High Superoxide Dismutase Activity of a Novel, Intramolecularly Imidazolato-Bridged Asymmetric Dicopper(II) Species. Design, Synthesis, Structure, and Magnetism of Copper(II) Complexes with a Mixed Pyrazole-Imidazole Donor Set. Inorg Chem. Mar. 12, 1997;36(6):1168-1175.
Voss, et al. Positron emission tomography (PET) imaging of neuroblastoma and melanoma with 64Cu-SarAr immunoconjugates. Proc Natl Acad Sci U S A. Oct. 30, 2007;104(44):17489-93. Epub Oct. 22, 2007.

(56) References Cited

OTHER PUBLICATIONS

Wadas, et al. Coordinating radiometals of copper, gallium, indium, yttrium, and zirconium for PET and SPECT imaging of disease. Chem Rev. May 12, 2010;110(5):2858-902. doi: 10.1021/cr900325h.

Waibel, et al. Stable one-step technetium-99m labeling of His-tagged recombinant proteins with a novel Tc(I)-carbonyl complex. Nat Biotechnol. Sep. 1999;17(9):897-901.

Wakankar, et al. Physicochemical stability of the antibody-drug conjugate Trastuzumab-DM1: changes due to modification and conjugation processes. Bioconjug Chem. Sep. 15, 2010;21(9):1588-95. doi: 10.1021/bc900434c.

Wang, et al. Efficient preparation and PEGylation of recombinant human non-glycosylated erythropoietin expressed as inclusion body in E. coli. Int J Pharm. Feb. 15, 2010;386(1-2):156-64. doi: 10.1016/j.ijpharm.2009.11.016. Epub Nov. 20, 2009.

Wangler, et al. Radiolabeled peptides and proteins in cancer therapy. Protein Pept Left. 2007;14(3):273-9.

Wohnert, et al. Protein alignment by a coexpressed lanthanide-binding tag for the measurement of residual dipolar couplings. J Am Chem Soc. Nov. 5, 2003;125(44):13338-9.

Wu, et al. microPET imaging of glioma integrin {alpha} v{beta}3 expression using (64)Cu-labeled tetrameric RGD peptide. J Nucl Med. Oct. 2005;46(10):1707-18.

Wu, et al. Trapping of intermediates during the refolding of recombinant human epidermal growth factor (hEGF) by cyanylation, and subsequent structural elucidation by mass spectrometry. Protein Sci. Apr. 1998;7(4):1017-28.

Yang, et al. Rational design of protein-based MRI contrast agents. J Am Chem Soc. Jul. 23, 2008;130(29):9260-7. doi: 10.1021/ja800736h. Epub Jul. 25, 2008.

Zheng, et al. A new class of macrocyclic lanthanide complexes for cell labeling and magnetic resonance imaging applications. J Am Chem Soc. Nov. 23, 2005;127(46):16178-88.

Zweit, et al. Nickel-57-doxorubicin, a potential radiotracer for pharmacokinetic studies using PET: production and radiolabelling. J Nucl Biol Med. Dec. 1994;38(4.Suppl 1):18-21.

U.S. Appl. No. 09/674,962, filed Nov. 8, 2000, Hauer et al.

Ackerman, et al. Structural and spectral studies of copper(II) and nickel(II) complexes of pyruvaldehyde mixed bis{N(4)-substituted thiosemicarbazones}. Polyhedron. 1999; 18(21):2759-2767.

Adams, et al. New biarsenical ligands and tetracysteine motifs for protein labeling in vitro and in vivo: synthesis and biological applications. J Am Chem Soc. May 29, 2002;124(21):6063-76.

Andersen, et al. Molecular mechanisms of in vivo metal chelation: implications for clinical treatment of metal intoxications. Environ Health Perspect. Oct. 2002;110 Suppl 5:887-90.

Andersen. Principles and recent developments in chelation treatment of metal intoxication. Chem Rev. Sep. 8, 1999;99(9):2683-710.

Bal, et al. Induction of oxidative DNA damage by carcinogenic metals. Toxicol Lett. Feb. 28, 2002;127(1-3):55-62.

Barondeau, et al. Nickel superoxide dismutase structure and mechanism. Biochemistry. Jun. 29, 2004;43(25):8038-47.

Bryngelson, et al. Expression, reconstitution, and mutation of recombinant Streptomycescoelicolor NiSOD. J Am Chem Soc. Jan. 21, 2004;126(2):460-1.

Bryngelson, et al. Nickel Superoxide Dismutase. Metal Ions in Life Sciences. 2007; 2:417-443.

Cai, et al. Kinetic study of acrylamide radical polymerization initiated by the horseradish peroxidase-mediated system. Int. J. Chem. Kinetics. 2012; 44(7):475-481.

Cherifi, et al. Transition metal complexes of L-cysteine containing di- and tripeptides. J Inorg Biochem. Jan. 1990;38(1):69-80.

Chivers, et al. Regulation of high affinity nickel uptake in bacteria. Ni2+-Dependent interaction of NikR with wild-type and mutant operator sites. J Biol Chem. Jun. 30, 2000;275(26):19735-41.

Chohan, et al. Ligand oxidations in high-spin nickel thiolate complexes and zinc analogues. Inorg Chem. Nov. 29, 2004;43(24):7726-34.

Choudhury, et al. Examination of the nickel site structure and reaction mechanism in Streptomyces seoulensis superoxide dismutase. Biochemistry. Mar. 23, 1999;38(12):3744-52.

Christlieb, et al. Ligands for molecular imaging: the synthesis of bis(thiosemicarbazone) ligands. Chemistry. Aug. 16, 2006;12(24):6194-206.

Chung, et al. A high-affinity metal-binding peptide from Escherichia coli HypB. J Am Chem Soc. Oct. 29, 2008;130(43):14056-7. Epub Oct. 4, 2008.

Cowley, et al. Fluorescence studies of the intra-cellular distribution of zinc bis(thiosemicarbazone) complexes in human cancer cells. Chem Commun (Camb). Feb. 21, 2005;(7):845-7. Epub Jan. 21, 2005.

Coyle, et al. Metallothionein: the multipurpose protein. Cell Mol Life Sci. Apr. 2002;59(4):627-47.

Derango, et al. Enzyme-mediated polymerization of acrylic monomers. Biotechnology Techniques. 1992; 6(6):523-526.

Desoize, et al. Particular aspects of platinum compounds used at present in cancer treatment. Crit Rev Oncol Hematol. Jun. 2002;42(3):317-25.

Donaldson, et al. Structural characterization of proteins with an attached ATCUN motif by paramagnetic relaxation enhancement NMR spectroscopy. J Am Chem Soc. Oct. 10, 2001;123(40):9843-7.

European search report dated Nov. 7, 2012 for EP Application No. 09747491.0.

Evans, et al. Application of chiral mixed phosphorus/sulfur ligands to enantioselective rhodium-catalyzed dehydroamino acid hydrogenation and ketone hydrosilylation processes. J Am Chem Soc. Mar. 26, 2003;125(12):3534-43.

Fernandez, et al. Structure, function, and inhibition of chemokines. Annu Rev Pharmacol Toxicol. 2002;42:469-99.

Fiedler, et al. Spectroscopic and computational studies of Ni Superoxide dismutatse: Electronic structure contributions to enzymatic function. J Am Chem Soc. Apr. 20, 2005;127(15):5449-62.

Gale, et al. Dipeptide-based models of nickel superoxide dismutase: solvent effects highlight a critical role to Ni-S bonding and active site stabilization. Inorg Chem. Oct. 17, 2011;50(20):10460-71. Epub Sep. 20, 2011.

Gale, et al. Exploring the effects of H-bonding in synthetic analogues of nickel superoxide dismutase (Ni-SOD): experimental and theoretical implications for protection of the Ni-SCys bond. Inorg Chem. Aug. 2, 2010;49(15):7080-96.

Gale, et al. Toward functional Ni-SOD biomimetics: achieving a structural/electronic correlation with redox dynamics. Inorg Chem. Oct. 3, 2011;50(19):9216-8. Epub Sep. 2, 2011.

Gale, et al. Versatile methodology toward NiN(2)S(2) complexes as nickel superoxide dismutase models: structure and proton affinity. Inorg Chem. Jul. 6, 2009;48(13):5620-2.

Gao, et al. CAAX-box protein, prenylation process and carcinogenesis. Am J Transl Res. May 25, 2009;1(3):312-25.

GenBank entry AAH31758.1 for murine metallothionein 2. Jan. 25, 2007.

GenBank entry AAH36990.1, for murine metallothionein 1. Jul. 15, 2006.

Gielda, et al. Zinc competition among the intestinal microbiota. mBio.asm.org. Jul./Aug. 2012; 3(4):e00171-12.

Glennon, et al. Nickel(II) transport in human blood serum. Studies of nickel(II) binding to human albumin and to native-sequence peptide, and ternary-complex formation with 1-histidine. Biochem J. 1982; 203:15-23.

Green. Copper-62 radiopharmaceuticals for diagnostic imaging with positron emission tomography (PET). Transition Met. Chem. 1997; 22:427-429.

Greenwood, et al. Manganese, Technetium and Rhenium. In Chemistry of the Elements. 2001, Butterworth Heinemann: Oxford. p. 1040-1069.

Harford, et al. Amino Terminal Cu(II)- and Ni(II)-Binding (ATCUN) Motif of Proteins and Peptides: Metal Binding, DNA Cleavage, and Other Properties. Acc. Chem. Res. 1997; 30:123-130.

Heinrich, et al. A square-planar di-N-carboxamido, dithiolato—cobalt(III) complex related to nitrile hydratase metallic site. Addition of axial ligands and EXAFS study of the derived dicyano and diisocyanido complexes. Inorganica Chimica Acta. 2001; 318:117-126.

(56) References Cited

OTHER PUBLICATIONS

Herbst, et al. Role of conserved tyrosine residues in NiSOD catalysis: a case of convergent evolution. Biochemistry. Apr. 21, 2009;48(15):3354-69.

Hiltunen. Search for new and improved radiolabeling methods for monoclonal antibodies. A review of different methods. Acta Oncol. 1993;32(7-8):831-9.

Hiromura, et al. Intracellular metal transport proteins. Trends in New Element Research. 2001; 35:23-25.

Holland, et al. Functionalized bis(thiosemicarbazonato) complexes of zinc and copper: synthetic platforms toward site-specific radiopharmaceuticals. Inorg Chem. Jan. 22, 2007;46(2):465-85.

International search report and written opiniondated Aug. 22, 2012 for PCT Application No. US2012/021382.

International search report dated Oct. 13, 2009 for PCT Application No. US09/43821.

Islam, et al. HAD, a Data Bank of Heavy-Atom Binding Sites in Protein Crystals: a Resource for use in Multiple Isomorphous Replacement and Anomalous Scattering Acta Cryst. (1998) D54, 1199-1206.

Jalilian, et al. Development of [67Ga]2-acetylpyridine 4,4-dimethyl thiosemicarbazone for detection of malignanciesy. Journal of Labelled Compounds and Radiopharmaceuticals. 2007; 50;414-415.

Jang, et al. Metal Ion Complexation by Peptide Monolayer formed on Au Electrodes Asian Chemical Congress Program, Aug. 25, 2005.

Jin, et al. DNA cleavage by copper-ATCUN complexes. Factors influencing cleavage mechanism and linearization of dsDNA. J Am Chem Soc. Jun. 15, 2005;127(23):8408-15.

Johnson, et al. Spectroscopic and computational investigation of three Cys-to-Ser mutants of nickel superoxide dismutase: insight into the roles played by the Cys2 and Cys6 active-site residues. J Biol Inorg Chem. Jun. 2010;15(5):777-93. Epub Mar. 24, 2010.

Kelland. The resurgence of platinum-based cancer chemotherapy. Nat Rev Cancer. Aug. 2007;7(8):573-84. Epub Jul. 12, 2007.

Kim, et al. Mixed Bis(thiosemicarbazone) Ligands for the Preparation of Copper Radiopharmaceuticals: Synthesis and Evaluation of Tetradentate Ligands Containing Two Dissimilar Thiosemicarbazone Functions. J. Med. Chem. 1997; 40:132-136.

Klaassen, et al. Metallothionein: an intracellular protein to protect against cadmium toxicity. Annu. Rev. Pharmacol. Toxicol. (1999) 39 p. 267-294.

Knipp,et al. Reaction of Zn7metallothionein with cis- and trans-[Pt(N-donor)2C12] anticancer complexes: trans-Pt(II) complexes retain their N-donor ligands. J Med Chem. Aug. 23, 2007;50(17):4075-86. Epub Aug. 1, 2007.

Kovala-Demertzi, et al. Platinum(II) and Palladium(II) Complexes of Pyridine-2-Carbaldehyde Thiosemicarbazone as Alternative Antiherpes Simplex Virus Agents. Bioinorganic Chemistry and Applications 2007; 1-6.

Krause, et al. MAPping the chiral inversion and structural transformation of a metal-tripeptide complex having ni-superoxide dismutase activity. Inorg Chem. Mar. 21, 2011;50(6):2479-87. Epub Jan. 31, 2011.

Krause, et al. Novel tripeptide model of nickel superoxide dismutase. Inorg Chem. Jan. 18, 2010;49(2):362-4.

Kruszynski, et al. [2-Acetylpyridine 1,1-(hexane-1,6-diyl)thiosemicarbazone-j3N,N0,S]chloroplatinum(II). Acta Crystallographica Section E 2005, E61, m2376-m2378.

Kuchar, et al. Biosynthesis of metal sites. Chem Rev. Feb. 2004;104(2):509-25.

Kulon, et al. Specific interactions of metal ions with Cys-Xaa-Cys unit inserted into the peptide sequence. J Inorg Biochem. Nov. 2007;101(11-12):1699-706. Epub Apr. 19, 2007.

Kumar, et al. Evaluation of an 111In-radiolabeled peptide as a targeting and imaging agent for ErbB-2 receptor expressing breast carcinomas. In Cancer Res. Oct. 15, 2007;13(20):6070-9.

Laurence, et al. Effect of N-terminal truncation and solution conditions on chemokine dimer stability: nuclear magnetic resonance structural analysis of macrophage inflammatory protein 1 beta mutants. Biochemistry. Jun. 30, 1998;37(26):9346-54.

Laurence, et al. Letter to the editor: 1H, 15N, 13C resonance assignments of the human protein tyrosine phosphatase PRL-1. J Biomol NMR. Jul. 2004;29(3):417-8.

Leach, et al. The role of complex formation between the *Escherichia coli* hydrogenase accessory factors HypB and SlyD. J Biol Chem. Jun. 1, 2007;282(22):16177-86. Epub Apr. 10, 2007.

Lee, et al. A discrete five-coordinate Ni(III) complex resembling the active site of the oxidized form of nickel superoxide dismutase. Chemistry. Jan. 2, 2012;18(1):50-3. doi: 10.1002/chem.201102690. Epub Dec. 9, 2011.

Lobana, et al. Bonding and structure trends of thiosemicarbazone derivatives of metals—An overview. Coordination Chemistry Reviews. 2009; 253:977-1055.

Mal, et al. The ATCUN domain as a probe of intermolecular interactions: application to calmodulin-peptide complexes. J Am Chem Soc. Nov. 27, 2002;124(47):14002-3.

Maroney, et al. Theoretical Study of the Oxidation of Nickel Thiolate Complexes by O(2). Inorg Chem. Feb. 14, 1996;35(4):1073-1076.

Maroney. Structure/function relationships in nickel metallobiochemistry. Curr Opin Chem Biol. Apr. 1999;3(2):188-99.

Martinez-Huitle, et al. Electrochemical behaviour of dopamine at covalent modified glassy carbon electrode with L-cysteine: preliminary results. Materials Research. 2009; 2(4):375-384.

Mathrubootham, et al. Bisamidate and mixed amine/amidate NiN2S2 complexes as models for nickel-containing acetyl coenzyme A synthase and superoxide dismutase: an experimental and computational study. Inorg Chem. Jun. 21, 2010;49(12):5393-406.

Maurer, et al. Studies on the mechanism of hypoxic selectivity in copper bis(thiosemicarbazone) radiopharmaceuticals. J Med Chem. Mar. 28, 2002;45(7):1420-31.

Meloni, et al. Organization and assembly of metal-thiolate clusters in epithelium-specific metallothionein-4. Journal of Biological Chemistry. 2006; 281(21):14588-14595.

Mendieta, et al. Complexation of cadmium by the C-terminal hexapeptide Lys-Cys-Thr-Cys-Cys-Ala from mouse metallothionein: study by differential pulse polarography and circular dichroism spectroscopy with multivariate curve resolution analysis. Analytica Chimica Acta. 1999; 390 (1-3):15-25.

Morier-Teissier, et al. Synthesis and antitumor properties of an anthraquinone bisubstituted by the copper chelating peptide Gly-Gly-L-His. J Med Chem. Jul. 23, 1993;36(15):2084-90.

Morleo, et al. Iron-nucleated folding of a metalloprotein in high urea: resolution of metal binding and protein folding events. Biochemistry. Aug. 10, 2010;49(31):6627-35.

Murray, et al. Axial Coordination of Monodentate Ligands with Nickel(III) Peptide Complexes. Inorg. Chem. 1982; 21:3501-3506.

Neupane, et al. Probing variable axial ligation in nickel superoxide dismutase utilizing metallopeptide-based models: insight into the superoxide disproportionation mechanism. J Am Chem Soc. Nov. 28, 2007;129(47):14605-18. Epub Nov. 7, 2007.

Neupane, et al. The influence of amine/amide versus bisamide coordination in nickel superoxide dismutase. Inorg Chem. Dec. 25, 2006;45(26):10552-66.

Nielson, et al. Distinct metal-binding configurations in metallothionein. J Biol Chem. May 10, 1985;260(9):5342-50.

Odenheimer, et al. Rractions of Cisplatin with Sulfur-containing amino acids and peptides I. Cysteine and Glutathione. Inorganica Chimica Acta. 1982; 66:L41-L43.

Office action dated Feb. 6, 2013 for U.S. Appl. No. 13/429,052.
Office action dated May 31, 2012 for U.S. Appl. No. 13/341,223.
Office action dated Jun. 10, 2011 for U.S. Appl. No. 12/465,448.
Office action dated Jun. 21, 2012 for U.S. Appl. No. 13/429,167.
Office action dated Jul. 1, 2013 for U.S. Appl. No. 13/428,864.
Office action dated Jul. 10, 2013 for U.S. Appl. No. 13/429,052.
Office action dated Aug. 27, 2012 for U.S. Appl. No. 13/429,052.
Office action dated Aug. 28, 2013 for U.S. Appl. No. 13/596,281.
Office action dated Dec. 11, 2012 for U.S. Appl. No. 13/428,864.
Office action dated Dec. 13, 2010 for U.S. Appl. No. 12/465,448.

Ott, et al. Preclinical and clinical studies on the use of platinum complexes for breast cancer treatment. Anticancer Agents Med Chem. Jan. 2007;7(1):95-110.

Park, et al. Protective effect of metallothionein against the toxicity of cadmium and other metals. Toxicology. (2001) 163 p. 93-100.

(56) References Cited

OTHER PUBLICATIONS

Pasini, et al. Some aspects of the reactivity of amino acids coordinated to metal ions. J. inorg. nucl. Chem. 1974; 36:2133-2144.

Pietersz, et al. Preclinical characterization and in vivo imaging studies of an engineered recombinant technetium-99m-labeled metallothionein-containing anti-carcinoembryonic antigen single-chain antibody. J Nucl Med. Jan. 1998;39(1):47-56.

Purcell, et al. An Introduction to Inorganic Chemistry. Harcourt Brace publishers, ISBN 0-03-056-768-8, p. 432, 1980.

Rulisek, et al. Coordination geometries of selected transition metal ions (Co2+, Ni2+, Cu2+, Zn2+, Cd2+, and Hg2+) in metalloproteins. J Inorg Biochem. Sep. 1998;71(3-4):115-27.

Ryan, et al. Nickel superoxide dismutase: structural and functional roles of Cys2 and Cys6. J Biol Inorg Chem. Jun. 2010;15(5):795-807. Epub Mar. 24, 2010.

Sakurai, et al. Interaction of Copper(II) and Nickel(II) with L-Histidine and Glycylglycyl-L-histidine as an Albumin Model. Inorg. Chem. 1980; 19:847-853.

Scheinberg, et al. Tumor imaging with radioactive metal chelates conjugated to monoclonal antibodies. Science. Mar. 19, 1982;215(4539):1511-3.

Schmidt, et al. Solution structure of a functional biomimetic and mechanistic implications for nickel superoxide dismutases. Chembiochem. Sep. 1, 2008;9(13):2135-46.

Scott, et al. Medicinal inorganic chemistry approaches to passivation and removal of aberrant metal ions in disease. Chem Rev. Oct. 2009;109(10):4885-910.

Shearer, et al. [Me4N](Ni(II)(BEAAM)): a synthetic model for nickel superoxide dismutase that contains Ni in a mixed amine/amide coordination environment. Inorg Chem. Nov. 27, 2006;45(24):9637-9.

Shearer, et al. A nickel superoxide dismutase maquette that reproduces the spectroscopic and functional properties of the metalloenzyme. Inorg Chem. Mar. 20, 2006;45(6):2358-60.

Shearer, et al. Metallopeptide based mimics with substituted histidines approximate a key hydrogen bonding network in the metalloenzyme nickel superoxide dismutase. Inorg Chem. Nov. 16, 2009;48(22):10560-71.

Shearer, et al. Probing variable amine/amide ligation in Ni(II)N2S2 complexes using sulfur K-edge and nickel L-edge X-ray absorption spectroscopies: implications for the active site of nickel superoxide dismutase. Inorg Chem. Apr. 7, 2008;47(7):2649-60. Epub Mar. 11, 2008.

Shively. Metal Ion Complexes for Antibody Imaging and Therapy in Breast Cancer. 2002.

Shullenberger, et al. Design and Synthesis of a Versatile DNA-Cleaving Metallopeptide Structural Domain. JACS. 1993; 115:11038-11039.

Sigel, et al. Coordinating Properties of the Amide Bond: Stability and Structure of Metal Ion Complexes of Peptides and Related Ligands. Chem. Rev., 1982, 82 (4), pp. 385-426.

Skinner, et al. Enzyme activity of phosphatase of regenerating liver is controlled by the redox environment and its C-terminal residues. Biochemistry. May 26, 2009;48(20):4262-72.

Smith, et al. Effect of Nickel(II) and Cobalt(III) and Other Metal Ions on the Racemization of Free and Bound L-Alaninel JACS. 1983; 105:293-295.

Steinert, et al. Ni-NTA resins: your key to efficient purification of 6xHis-tagged proteins. Qiagen News. 1997; 4:11-15.

Takahara, et al. Crystal structure of double-stranded DNA containing the major adduct of the anticancer drug cisplatin. Nature. Oct. 19, 1995;377(6550):649-52.

Thauer. Nickel to the fore. Science. 2001; 2931:264-1265.

Thilakaraj, et al. In silico identification of putative metal binding motifs. Bioinformatics. Feb. 1, 2007;23(3):267-71. Epub Dec. 5, 2006.

Tietze, et al. Development of a functional cis-prolyl bond biomimetic and mechanistic implications for nickel superoxide dismutase. Chemistry. Jul. 5, 2010;16(25):7572-8.

Tietze, et al. New insight into the mode of action of nickel superoxide dismutase by investigating metallopeptide substrate models. Chemistry. 2009;15(2):517-23.

Torrado, et al. Exploiting polypeptide motifs for the design of selective cu(II) ion chemosensors. JACS. 1998; 120:609-610.

UK search and examination report dated May 11, 2012 for GB 1200554.2.

Vasak, et al. Chemistry and biology of mammalian metallothioneins. J. Bio. Inorg. Chem. 2011; 16:1067-1078.

Vila, et al. Cylometallated semicarbazone complexes of palladium(II). Crystal and molecular structure of [{Pd[C6H4C(Et)=NN(H)C(=O)NH2]}2(m-Ph2P(CH2)3PPh2)][ClO4]2. Journal of Organometallic Chemistry. 1998; 556:21-30.

Walsh, et al. Protein posttranslational modifications: the chemistry of proteome diversifications. Angew Chem Int Ed Engl. Dec. 1, 2005;44(45):7342-72.

Wierzba, et al. Production and properties of a bifunctional fusion protein that mediates attachment of vero cells to cellulosic matrices. Biotechnol Bioeng Jul. 20, 1995; 47(2):147-54.

Wuerges, et al. Crystal structure of nickel-containing superoxide dismutase reveals another type of active site. Proc Natl Acad Sci U S A. Jun. 8, 2004;101(23):8569-74. Epub Jun. 1, 2004.

Xuan, et al. Formation of Some Cysteine-Containing Peptide Monolayers on Au Electrodes and Their Applications for Metal Ion Sensing and Electrocatalytic Reactions. Bull. Korean Chem. Soc. 2008;29(7):1301-1302.

Yang, et al. Sub-ppt detection limits for copper ions with Gly-Gly-His modified electrodes. Chem Commun (Camb). Oct. 7, 2001;(19):1982-3.

Yokel. Blood-brain barrier flux of aluminum, manganese, iron and other metals suspected to contribute to metal-induced neurodegeneration. J Alzheimers Dis. Nov. 2006;10(2-3):223-53.

Yokoyama, et al. Mononuclear and dinuclear complexes of 99mTc. Int J Appl Radiat Isot. Oct. 1982;33(10):929-36.

Zhang, et al. A role for SlyD in the *Escherichia coli* hydrogenase biosynthetic pathway. J Biol Chem. Feb. 11, 2005 ;280(6):4360-6. Epub Nov. 29, 2004.

Zhao, et al. Horseradish peroxidase immobilized in macroporous hydrogel for acrylamide polymerization. Journal of Polymer Science Part A: Polymer Chemistry 2008; 46(6):2222-2232.

Zoroddu, et al. Molecular Mechanisms in Nickel Carcinogenesis: Modeling Ni(II) Binding Site in Histone H4. Environ Health Perspect. Oct. 2002;110 Suppl 5:719-23.

Zoroddu, et al. Multidimensional NMR spectroscopy for the study of histone H4-Ni(II) interaction. Dalton Trans. Jan. 21, 2007;(3):379-84. Epub Dec. 5, 2006.

Acchione, et al. Impact of linker and conjugation chemistry on antigen binding, Fc receptor binding and thermal stability of model antibody-drug conjugates. MAbs. May-Jun. 2012;4(3):362-72. doi: 10.4161/mabs.19449. Epub Apr. 26, 2012.

Adem, et al. Auristatin antibody drug conjugate physical instability and the role of drug payload. Bioconjug Chem. Apr. 16, 2014;25(4):656-64. doi: 10.1021/bc400439x. Epub Mar. 13, 2014.

Bal, et al. Ni(II) specifically cleaves the C-terminal tail of the major variant of histone H2A and forms an oxidative damage-mediating complex with the cleaved-off octapeptide. Chem Res Toxicol. Jul. 2000;13(7):616-24.

Beckley, et al. Investigation into temperature-induced aggregation of an antibody drug conjugate. Bioconjug Chem. Oct. 16, 2013;24(10):1674-83. doi: 10.1021/bc400182x. Epub Sep. 26, 2013.

Boylan, et al. Conjugation site heterogeneity causes variable electrostatic properties in Fc conjugates. Bioconjug Chem. Jun. 19, 2013;24(6):1008-16. doi: 10.1021/bc4000564. Epub May 31, 2013.

Dominy, et al. An electrostatic basis for the stability of thermophilic proteins. Proteins. Oct. 1, 2004;57(1):128-41.

Gill, et al. Nickel-dependent oxidative cross-linking of a protein. Chem Res Toxicol. Mar. 1997;10(3):302-9.

Glyakina, et al. Different packing of external residues can explain differences in the thermostability of proteins from thermophilic and mesophilic organisms. Bioinformatics. Sep. 1, 2007;23(17):2231-8. Epub Jun. 28, 2007.

(56) References Cited

OTHER PUBLICATIONS

Jackson, et al. In vitro and in vivo evaluation of cysteine and site specific conjugated herceptin antibody-drug conjugates. PLoS One. Jan. 14, 2014;9(1):e83865. doi: 10.1371/journal.pone.0083865. eCollection 2014.

Krause, et al. Embedding the Ni-SOD mimetic Ni-NCC within a polypeptide sequence alters the specificity of the reaction pathway. Inorg Chem. Jan. 7, 2013;52(1):77-83. doi: 10.1021/ic301175f. Epub Dec. 10, 2012.

Narhi, et al. Asn to Lys mutations at three sites which are N-glycosylated in the mammalian protein decrease the aggregation of *Escherichia coli*-derived erythropoietin Protein Eng. Feb. 2001;14(2):135-40.

Strop, et al. Location matters: site of conjugation modulates stability and pharmacokinetics of antibody drug conjugates. Chem Biol. Feb. 21, 2013;20(2):161-7.doi: 10.1016/j.chembiol.2013.01.010.

Wang, et al. Structural characterization of the maytansinoid-monoclonal antibody immunoconjugate, huN901-DM1, by mass spectrometry. Protein Sci. Sep. 2005;14(9):2436-46. Epub Aug. 4, 2005.

U.S. Appl. No. 14/088,009, filed Nov. 22, 2013, Laurence et al.

Finnegan, et al. Variable-temperature magnetic circular dichroism spectroscopy as a probe of the electronic and magnetic properties of nickel in jack bean urease. J. Am. Chem. Soc., 1991, 113 (10), pp. 4030-4032.

Fujii; et al., "Formation of four isomers at the asp-151 residue of aged human alphaA-crystallin by natural aging. Biochem Biophys Res Commun. Nov. 30, 1999;265(3):746-51."

Glass, et al. Controlling the chiral inversion reaction of the metallopeptide Ni-asparagine-crysteine-cysteine with dioxygen. Inorg Chem. Sep. 17, 2012; 51(18): 10055-63.

Notice of allowance dated Jul. 11, 2012 for U.S. Appl. No. 13/429,167.

Notice of allowance dated Jul. 25, 2012 for U.S. Appl. No. 13/341,223.

Notice of allowance dated Oct. 27, 2014 for U.S. Appl. No. 13/429,052.

Notice of allowance dated Dec. 23, 2011 for U.S. Appl. No. 12/465,448.

"Office action dated Feb. 6, 2015 for U.S. Appl. No. 13/305,247."

Office Action dated Jun. 19, 2014 for U.S. Appl. No. 13/350,247.

Office action dated Aug. 26, 2014 for U.S. Appl. No. 13/596,281.

Office action dated Aug. 27, 2014 for U.S. Appl. No. 13/429,052.

Office action dated Oct. 23, 2014 for U.S. Appl. No. 13/596,281.

Pelmenschikov, et al. Nickel superoxide dismutase reaction mechanism studied by hybrid density functional methods. J. Am. Chem. Soc. 2006, 128, 7466-7475.

U.S. Appl. No. 13/596,281, filed Aug. 28, 2012.

* cited by examiner

Panel A.

Panel B.

Panel A

Panel B

Panel A

Panel B

Panel A.

Panel B.

Panel A

Panel B ated O₂-free and incubated 300 minutes to achieve maximum formation of LLL-Ni$^{II}$-NCC, then treated with O₂. The spectrum shown with a solid black line was collected at t=300 minutes to allow for maximum complex formation, and then the sample was injected with O₂. The gray spectrum was collected after 800 total minutes of incubation (600 minutes

SEQUENCE LISTING

```
<160> NUMBER OF SEQ ID NOS: 12

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Asn Cys Cys
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Asn Cys Cys Gly Gly Lys
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Cys Cys
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Asn Asn Cys Cys
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Asn Gly Cys Cys
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 6

Gly Gly Gly Cys Cys Gly Gly Lys
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gly Asn Cys His Gly Gly Lys
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: D-amino acid

<400> SEQUENCE: 8

Gly Gly Asn Cys Cys
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 9

Gly Gly Asn Cys Cys
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-amino acid

<400> SEQUENCE: 10

Gly Gly Asn Cys Cys
1               5
```

```
<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: D-amino acid

<400> SEQUENCE: 11

Gly Gly Asn Cys Cys
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asn Asn Cys Cys Ile Gln
1               5
```

METAL ABSTRACTION PEPTIDE WITH SUPEROXIDE DISMUTASE ACTIVITY

CROSS REFERENCE

This application claims the benefit of U.S. Provisional Application No. 61/654,547, filed on Jun. 1, 2012, the contents of which is incorporated by reference herein in its entirety.

SEQUENCE LISTING

The instant application contains a Sequence Listing which has been submitted via EFS-Web and is hereby incorporated by reference in its entirety. The ASCII copy, created on Aug. 8, 2013, is named 41861-702.201_SL.txt and is 3,120 bytes in size.

BACKGROUND OF THE INVENTION

Peptide tags that can be encoded in the genetic material of an organism for recombinant expression of proteins have been utilized for purification and identification of protein products. The advantage of a peptide tag is that the tag is covalently attached to the protein of interest without the need for additional chemical steps to label the protein. Peptide-based tags have been developed to allow for detecting a tagged protein in cell culture assays or cell lysates using antibodies that recognize the peptide tag.

While these technologies might be useful in in-situ or in-vitro assays, the applications to in-vivo analysis remain limited. Moreover, such peptide tags have limited or no functionality outside of protein purification or identification.

SUMMARY OF THE INVENTION

In some embodiments, the invention provides a method of treating a defect in superoxide dismutase in a subject in need thereof, the method comprising administering to the subject a therapeutically-effective amount of: i) a peptide comprising a sequence $XC_1C_2$, wherein X is any natural or non-natural amino acid or amino acid analog, and further wherein $C_1$ and $C_2$ are each individually chosen from a cysteine and a sulfur-containing alpha or beta amino acid; and ii) a metal bound to the peptide.

In some embodiments, the invention provides a method of reducing pain in a subject in need thereof, the method comprising administering to the subject a therapeutically-effective amount of: i) a peptide comprising a sequence $XC_1C_2$, wherein X is any natural or non-natural amino acid or amino acid analog, and further wherein $C_1$ and $C_2$ are each individually chosen from a cysteine and a sulfur-containing alpha or beta amino acid; and ii) a metal bound to the peptide.

In some embodiments, the invention provides a method of reducing inflammation in a subject in need thereof, the method comprising administering to the subject a therapeutically-effective amount of: i) a peptide comprising a sequence $XC_1C_2$, wherein X is any natural or non-natural amino acid or amino acid analog, and further wherein $C_1$ and $C_2$ are each individually chosen from a cysteine and a sulfur-containing alpha or beta amino acid; and ii) a metal bound to the peptide.

In some embodiments, the invention provides a method of increasing in-vivo half-life of a therapeutic polypeptide, the method comprising: i) providing a therapeutic polypeptide with an amino terminus, wherein the amino terminus has a sequence $XC_1C_2$, wherein X is any natural or non-natural amino acid or amino acid analog, and further wherein $C_1$ and $C_2$ are each individually chosen from a cysteine and a sulfur-containing alpha or beta amino acid; ii) forming a complex between a metal and the therapeutic polypeptide under conditions suitable for chiral inversion of $C_2$; and iii) separating the metal from the therapeutic polypeptide with chirally inverted $C_2$, wherein the in-vivo half-life of the therapeutic polypeptide is increased.

In some embodiments, the invention provides a method of performing a chemical reaction, the method comprising contacting: i) a peptide comprising a sequence $XC_1C_2$, wherein X is any natural or non-natural amino acid or amino acid analog, wherein $C_1$ and $C_2$ are each individually chosen from a cysteine and a sulfur-containing alpha or beta amino acid, and wherein a metal is bound to the peptide; and ii) chemical starting materials, whereupon the chemical starting materials are combined into a product.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DESCRIPTION

Figure 1:
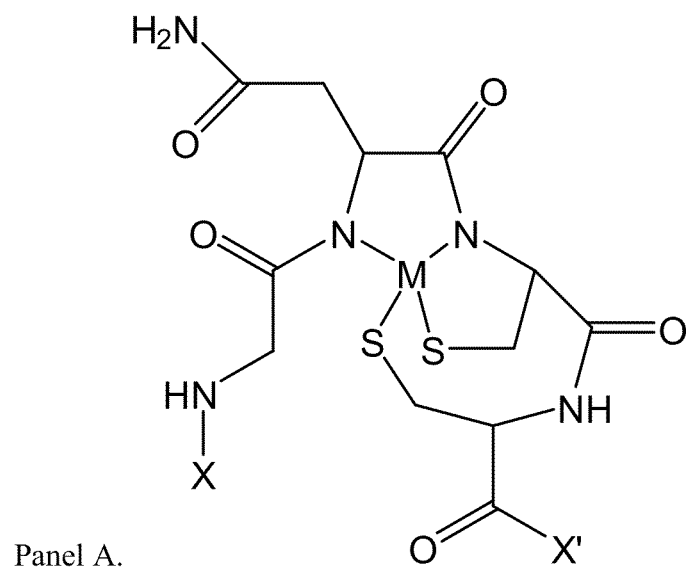
FIG. 1 panel A shows a possible binding arrangement for a polypeptide with metal. Panel B, shows a possible binding arrangement for a polypeptide with nickel showing the structure of Ni-GGNCC (SEQ ID NO. 1) with bisamide coordination.
Figure 1:
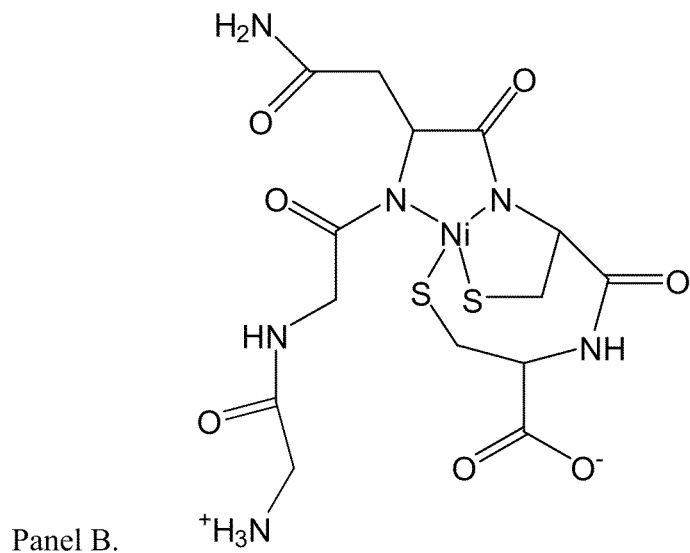

The present disclosure generally relates to metal abstraction peptide tags (MAP tags) and to methods of preparing and using such tags for a variety of uses.

DEFINITIONS

As used herein, the abbreviations for the natural L-enantiomeric amino acids are conventional and are as follows: alanine (A, Ala); arginine (R, Arg); asparagine (N, Asn); aspartic acid (D, Asp); cysteine (C, Cys); glutamic acid (E, Glu); glutamine (Q, Gln); glycine (G, Gly); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); valine (V, Val). Typically, X can indicate any amino acid. However, in some embodiments, X can be asparagine (N), glutamine (Q), histidine (H), lysine (K), or arginine (R).

When an amino acid sequence is represented as a series of three-letter or one-letter amino acid abbreviations, it will be understood that the left-hand direction is the amino terminal direction and the right-hand direction is the carboxy terminal direction, in accordance with standard usage and convention.

The term "metal" as used herein refers to metals in elemental form, metal atoms, and metal ions interchangeably.

The terms "purification", "separation", "extraction" and "isolation" are used interchangeably to refer to the process of separating a target polypeptide from other components in a polypeptide-containing sample.

"Operably linked" refers to a linkage in which the regulatory DNA sequences and the DNA sequence to be expressed are connected in such a way as to permit transcription and ultimately translation.

The term "host cell" refers to those cells capable of growth in culture and capable of hosting nucleic acids encoding the protein-based constructs described herein.

The term "X % sequence similarity" is not intended to be limited to sequences having a X % sequence similarity over their entire length, but rather includes sequence similarity over a portion of the length of the polynucleotide or polypeptide.

Metal Abstraction Peptide (MAP)

The present disclosure generally relates to tripeptide motifs and methods of using such motifs. These metal abstraction peptides (MAPs) have the ability to bind to metals, which makes them useful for a variety of applications. In particular, the tripeptides of the present disclosure have applications in site-specific modulation of peptides or proteins to which they are linked. End uses of the modulated proteins can include imaging, research, therapeutics, pharmaceuticals, chemotherapy, chelation therapy, and metal sequestering.

The present disclosure provides a tripeptide having the sequence $XC_1C_2$; wherein X is any natural or non-natural amino acid or amino acid analog such that $XC_1C_2$ is capable of binding a metal. In various embodiments, the tripeptide is capable of binding metal in a square planar orientation or square pyramidal orientation or both. In various embodiments, $C_1$ and $C_2$ are the same or different; and $C_1$ and $C_2$ individually are chosen from a cysteine and a cysteine-like non-natural amino acid or amino acid analog. In various embodiments, $C_1$ and $C_2$ are each individually chosen from sulfur-containing alpha or beta amino acids.

The present disclosure also provides a tripeptide having the sequence $XC_1C_2$ and a bound metal; wherein the metal is complexed with or bound to the tripeptide. In various embodiments, X is any natural or non-natural amino acid or amino acid analog such that $XC_1C_2$ and the bound metal are in a square planar orientation or square pyramidal orientation or both; and wherein $C_1$ and $C_2$ are the same or different; and wherein $C_1$ and $C_2$ individually are chosen from a cysteine and a cysteine-like non-natural amino acid or amino acid analog. In various embodiments, $C_1$ and $C_2$ are each individually chosen from sulfur-containing alpha or beta amino acids.

In addition, the present disclosure provides methods comprising complexing with a metal a tripeptide having the sequence $XC_1C_2$ to form a metal-$XC_1C_2$ complex; wherein X is any natural or non-natural amino acid or amino acid analog such that metal-$XC_1C_2$ complex has a square planar orientation or square pyramidal orientation or both; and wherein $C_1$ and $C_2$ are the same or different; and wherein $C_1$ and $C_2$ individually are chosen from a cysteine and a cysteine-like non-natural amino acid or amino acid analog. In various embodiments, $C_1$ and $C_2$ are each individually chosen from sulfur-containing alpha or beta amino acids.

The X in the MAP sequence can be any natural or non-natural amino acid. In some specific embodiments, X in the MAP sequence can be methionine (M), glycine (G), or asparagine (N). When an amino acid sequence is represented as a series of three-letter or one-letter amino acid abbreviations, it will be understood that the left-hand direction is the amino terminal direction and the right-hand direction is the carboxy terminal direction, in accordance with standard usage and convention. Generally, the present disclosure is related to short, novel peptide motifs that strongly bind with a select metal, referred to as metal abstraction peptides (MAP(s)). As such, these MAPs can be used, among other things, to extract the select metal from a composition. The MAPs of the present disclosure are three amino acids in length, and can be included in longer polypeptides and proteins at the N-terminus, C-terminus, or any position in between. In various embodiments, however, it can be advantageous for the MAP to be present in a polypeptide or protein configuration that presents the MAP for binding with a metal, such as being present in an external loop. The MAP can also be covalently attached to a polypeptide or protein through a linker, such as at the N-terminus, C-terminus, or through a side-chain from the polypeptide or protein. For example, such linkers can include amide bonds, or esters. The MAP also can be attached to a non-peptide entity. Non-peptide entities include without limitation carbohydrates, glycoproteins, and/or covalent linkers, including polyethylene glycol. Additionally, more than one MAP can be present on a particular molecule. In various embodiments, one or more MAPs can be covalently linked to an antibody. In various embodiments, the metal abstraction peptide (MAP) is a tripeptide capable of complexation with metal ions, as described in U.S. Patent Publication 2010/0221839.

A peptide of the invention can be administered to a subject. A plurality of animals can be subjects of the invention, an animal can be, for example, a human, dog, a cat, a horse, a cow, or a pig can be subjects of the invention. In some embodiments, a subject is a human. A subject can be of any age, including, for example, elderly adults, adults, adolescents, pre-adolescents, children, toddlers, and infants.

Chemical Structure/Peptide Sequence.

The MAPs of the present disclosure generally comprise at least three contiguous amino acid residues capable of binding a metal. The MAP tags of the present disclosure generally have a sequence represented by $XC_1C_2$, in which $C_1$ and $C_2$ can be the same or different and can be a cysteine, or a cysteine-like non-natural amino acid, or a cysteine-like amino acid analog. For example, $C_1$ and/or $C_2$ can be a sulfur-containing alpha- or beta-amino acid. In various embodiments, X is selected from N, Q, H, K, and R. In various embodiments, $XC_1C_2$ are L-amino acids. In various embodiments, $XC_1C_2$ are L-amino acids, where X is selected from N, Q, H, K, and R. In various embodiments, X is achiral, for example, X is glycine.

In certain embodiments, the MAP tag can be attached to another molecule. For example, the MAP tag can be attached to a non-peptide entity like a carbohydrate. For example, the carbohydrate can be a component in a glycoprotein. Alternatively, the carbohydrate can be hyaluronic acid or chondroitin. The attachment can be covalent, and can be affected through a linker. In various embodiments, the MAP is attached to an antibody for targeted delivery.

In some embodiments, the MAP tag can comprise a sequence as follows: $NC_1C_2$; $Z_1$—$NC_1C_2$—$Z_2$; $Z_1$—$NC_1C_2$; $NC_1C_2$—$Z_2$; $QC_1C_2$; $Z_1$-$QC_1C_2$—$Z_2$; $Z_1$-$QC_1C_2$; $QC_1C_2$—$Z_2$; $HC_1C_2$; $Z_1$—$HC_1C_2$—$Z_2$; $Z_1$—$HC_1C_2$; $HC_1C_2$—$Z_2$; $KC_1C_2$; $Z_1$—$KC_1C_2$—$Z_2$; $Z_1$—$KC_1C_2$; $KC_1C_2$—$Z_2$; $RC_1C_2$; $Z_1$—$RC_1C_2$—$Z_2$; $Z_1$—$RC_1C_2$; or $RC_1C_2$—$Z_2$. $Z_1$ can be any amino acid or any sequence of amino acids, and $Z_2$ can be any amino acid or sequence of amino acids that is equivalent or not equivalent to $Z_1$. Non-natural and amino acids analogues can be included as $Z_1$ and $Z_2$. In various embodiments, $Z_1$ and $Z_2$ are both natural amino acids or sequences of natural amino acids. In various embodiments, $XC_1C_2$ are L-amino acids, where X is selected from N, Q, H, K, and R. In various embodiments, $XC_1C_2$ are L-amino acids, where X is selected from N, Q, H, K, and R, and $Z_1$ and $Z_2$ are both sequences of natural amino acids. In various embodiments, X is achiral, for example, X is glycine. In some embodiments, the peptide is a sequence of three amino acids, for example, $XC_1C_2$, XCC, or NCC, and the N-terminus of the peptide is a free amine. In some embodiments, the free amine binds a metal more strongly than does an amide of the N-terminal amine.

In some embodiments, a MAP tag of the present disclosure can be encoded in line with a gene or nucleotide sequence that provides for targeted delivery of the MAP tag, either before MAP tag complexation with a metal or after complexation with a metal. This can be accomplished using genes, peptides, or other motifs known to be useful for targeting. For example, MAP tags can be incorporated within an antibody, growth factors, peptides, and the like. Additionally, it can be incorporated into a peptide or protein using any synthetic or biosynthetic method for peptide or protein production. In various embodiments, one or more MAPs are covalently linked to an antibody via a non-natural linker. In various embodiments, one or more MAPs are covalently linked to an antibody via a polyether linker, such as polyethylene glycol or polypropylene glycol.

In some uses, the MAP tag spontaneously reacts with a metal to form a peptide-metal complex. Metal-MAP complexes can form in solution or via transmetallation or any other process.

Metal Binding.

Metal binding by MAP tags according to the invention can be accomplished using atoms in very close proximity, and as such, extreme conditions are required to release the metal. Thermal and chemical denaturation of the MAP tag and the material to which it is covalently linked permits slow release of the metal. For example, use of extreme conditions (e.g. boiling temperature, denaturants, chelators) can lead to slow release of the metal over a period of time (e.g., several to many hours).

In certain embodiments, the MAP tags of the present disclosure, alone or when incorporated into a polypeptide, protein, glycoprotein, or antibody, can complex with a metal to form a MAP tag-metal complex having a square planar and/or square pyramidal geometry. The metal can complex with the MAP tag through 2N:2S coordination. In various embodiments, the metal-MAP complex can have an additional coordination site for complexation of an additional ligand to the metal, or for an additional site for chemical reactivity with the metal.

In general, the MAP tags of the present disclosure can bind, referring to IUPAC Group: Group 3 metals, such as Y; Group 4 metals such as Ti, Zr, Hf; Group 5 metals, such as V; Group 6 metals, such as Cr, Mo, W; Group 7 metals such as Mn, Tc, Re; Group 8 metals, such as Fe and Ru; Group 9 metals, such as Co, Rh, Ir; Group 10 metals such as Ni, Pd, Pt; Group 11 metals, such as Cu, Ag, Au; Group 12 metals, such as Zn, Cd, Hg; Group 13 metals, such as Al, Ga, In, Tl; Group 14 metals, such as Sn and Pb; and Group 15 metals, such as Bi. In certain embodiments, the MAP tag binds to lanthanides or actinides, such as U. In various embodiments, the MAP binds with alkine earth metals, such as Mg, Ca, Ba, Ra. The MAP tag can bind and form a MAP tag-metal complex with Zn, Ni, Cu, Co, Pt, Pd, Au, Ag, Pb, and Fe. In various embodiments, the metal is Ni. In various embodiments, the metal Ni converts between $Ni^{II}$ and $Ni^{III}$, and/or vice versa.

In some embodiments, a MAP tag is capable of binding metals with high affinity. A MAP tag can also be capable of abstracting a metal from various compositions ranging from fluids to solids. Consequently, the ability of MAP tags to abstract the metal, rather than share coordination, make them amenable for use in separating a specific metal from another composition. In some embodiments, the MAP tags are capable of sequestering a metal ion from compositions by complexing with the metal and then abstracting or removing the metal from a component in the composition, such as a chelating agent (e.g., NTA) or a solid support conjugated with, for example, IDA or NTA. As such, the MAP tag is a metal abstraction peptide (MAP) tag. In various embodiments, binding is best accomplished using a partial chelator as opposed to a chelator that coordinates at all available binding sites on the metal. In various embodiments, chelators like EDTA that coordinate Ni and Cu at all available binding sites on the metal proceed much more slowly.

A MAP tag can bind to metal in a plurality of ratios. In some embodiments, a MAP tag can bind to metal in a ratio of about 1:about 1; about 1:about 2; about 1:about 3; about 1:about 4; about 1:about 5; about 1:about 6; about 1:about 7; about 1:about 8; about 1:about 9; or about 1:about 10. In some embodiments, a MAP tag can bind to metal in a ratio of about 10:about 1; about 9:about 1; about 8:about 1; about 7:about 1; about 6:about 1; about 5:about 1; about 4:about 1; about 3:about 1; or about 2:about 1. In some embodiments, the ratio is 1:1.

Peptide Structures.

Stabilization of the three-dimensional structure of a protein can involve interactions between amino acids located near one another and/or far apart along the primary sequence of a protein. A peptide comprising a sequence $XC_1C_2$, wherein X is any natural or non-natural amino acid or amino acid analog, and further wherein $C_1$ and $C_2$ are each individually chosen from a cysteine and a sulfur-containing alpha or beta amino acid can be comprised in the primary structure of a peptide.

The secondary structure of a peptide comprising a sequence $XC_1C_2$ can be folded into an α-helix, a β-sheet, a β-turn, a β-strand, or a combination thereof. A peptide comprising a sequence $XC_1C_2$ can be functional when folded into a secondary structure comprising α-helixes and/or β-sheets.

In some embodiments, the functionality of the peptide comprising a sequence $XC_1C_2$ can provide a method of treating a defect in superoxide dismutase in a subject in need thereof. In some embodiments, the functionality of the peptide comprising a sequence $XC_1C_2$ can provide a method of reducing pain in a subject in need thereof. In some embodiments, the functionality of the peptide comprising a sequence $XC_1C_2$ can provide a method of reducing inflammation in a subject in need thereof. In some embodiments, the functionality of the peptide comprising a sequence $XC_1C_2$ can provide a method of increasing in-vivo half-life of a therapeutic polypeptide. In some embodiments, the functionality of the peptide comprising a sequence $XC_1C_2$ can provide a method of performing a chemical reaction.

A peptide comprising a sequence $XC_1C_2$ can be folded into a tertiary structure. Folding of the peptide into a tertiary structure can involve a plurality of molecular interactions. Non-limiting examples of molecular interactions that can influence the folding of a peptide comprising a sequence $XC_1C_2$ into a tertiary structure can include: a) hydrogen bonds; b) Van der Waals interactions; c) ionic bonds; d) disulfide bonds; e) hydrophobic interactions; and f) aromatic interactions. In some embodiments, a plurality of factors can influence the folding of a peptide comprising sequence $XC_1C_2$ into a tertiary structure. Non-limiting examples of factors that can influence the folding of a peptide comprising a sequence $XC_1C_2$ into a tertiary structure can include: a) pH; b) hydrophobicity of the environment surrounding the peptide; c) hydrophilicity of the environment surrounding the peptide; and d) interactions with additional molecules.

In some embodiments, a peptide comprising a sequence $XC_1C_2$ adopts a tertiary structure under physiological conditions, wherein a basic amino acid located at least 17 amino acids away from $C_1$ by amino acid sequence is located within 20 angstroms in space from $C_1$.

In some embodiments, a peptide comprising a sequence $XC_1C_2$ adopts a tertiary structure, wherein the sequence $XC_1C_2$ is available for binding metal. In some embodiments, a peptide comprising a sequence $XC_1C_2$ adopts a tertiary structure, wherein the sequence $XC_1C_2$ is not available for binding metal. In some embodiments, denaturing conditions can expose a $XC_1C_2$ sequence comprised in a peptide and render the sequence available for binding metal.

Peptide Lengths.

A peptide comprising a sequence $XC_1C_2$ can be incorporated into peptides of various sizes. A peptide comprising a sequence $XC_1C_2$ can be about 3 amino acids, about 4 amino acids, about 5 amino acids, about 6 amino acids, about 7 amino acids, about 8 amino acids, about 9 amino acids, about 10 amino acids, about 11 amino acids, about 12 amino acids, about 13 amino acids, about 14 amino acids, about 15 amino acids, about 16 amino acids, about 17 amino acids, about 18 amino acids, about 19 amino acids, about 20 amino acids, no more than 20 amino acids, no more than 25 amino acids, no more than 30 amino acids, no more than 35 amino acids, no more than 40 amino acids, no more than 45 amino acids, no more than 50 amino acids, no more than 55 amino acids, no more than 60 amino acids, no more than 65 amino acids, no more than 70 amino acids, no more than 75 amino acids, no more than 80 amino acids, no more than 85 amino acids, no more than 90 amino acids, no more than 95 amino acids, no more than 100 amino acids, no more than 110 amino acids, no more than 120 amino acids, no more than 130 amino acids, no more than 140 amino acids, no more than 150 amino acids, no more than 160 amino acids, no more than 170 amino acids, no more than 180 amino acids, no more than 190 amino acids, no more than 200 amino acids, no more than 225 amino acids, no more than 250 amino acids, no more than 275 amino acids, no more than 300 amino acids, no more than 325 amino acids, no more than 350 amino acids, no more than 375 amino acids, no more than 400 amino acids, no more than 425 amino acids, no more than 450 amino acids, no more than 475 amino acids, and no more than 500 amino acids. In some embodiments a peptide comprising a sequence $XC_1C_2$ is no more than 500 amino acids.

Site-Specific Chiral Inversion of Amino Acids

In various embodiments, the present disclosure relates to MAP(s) that demonstrate chiral inversion and/or have antioxidant activity, as well as methods of generating and using the same.

D-amino acids that have been observed in proteins and peptides often impart significant differences in biological function to the chiral peptide and protein variants; while some can act as inhibitors, others can act as activators. The introduction of a D-amino acid often alters the structure of the peptide or protein, which can in turn influence the biological activity of the parent peptide. Conversely, chiral mutagenesis of proteins has been shown to stabilize certain proteins, including insulin. Generally, naturally occurring, biosynthetic peptides and proteins that contain D amino acids are first generated entirely from L-amino acids, and the inversion occurs as a post-translational modification.

In various embodiments of the invention, the metal-tripeptide (MAP) complex undergoes chiral inversion in a site-specific manner. This modification is distinctive, as site-specific chiral inversion is not often observed in proteins. The structural change that occurs in this complex can be both site and structurally specific and can occur substantially more rapidly than random background. Moreover, random chiral changes often require highly elevated temperature to occur and result in an approximately equal mixture of both chiral forms, rather than a single form. In various embodiments of the invention, the chiral inversion by the MAP-based chemistry results in a substantially homogeneous single form. For example, chiral inversion by the MAP-based chemistry can result in a mixture with greater than about 70%, greater than about 80%, greater than about 90%, greater than about 95%, or greater than about 99% enrichment in one D-amino acid over the corresponding L-amino acid.

In one embodiment, the present disclosure provides methods for site-specific chiral inversion of amino acids. Such methods can proceed at reactions occurring at room temperature and near neutral pH in aqueous solution over the course of hours. In general, the amino acids comprise at least three contiguous L-enantiomeric (L) amino acid residues capable of binding a metal, or at least three contiguous amino acids including an achiral amino acid and two L-enantiomeric amino acids. In various embodiments, MAP tags affecting or participating in site-specific chiral inversion generally have a sequence represented by $XC_1C_2$, in which $C_1$ and $C_2$ can be the same or different and can be a cysteine, or a cysteine-like non-natural amino acid (e.g., a sulfur containing alpha- or beta-amino acid), and in which $C_2$ also can be histidine, or a histidine-like non-natural amino acid, and in which X can be any natural or non-natural amino acid or amino acid analog. In some embodiments, the peptide tag formed is capable of binding a metal in square planar and/or pyramidal geometry.

A particular molecule or complex of interest can comprise one or more of the amino acids represented by $XC_1C_2$ and can include additional amino acids (e.g., a peptide or protein), as well as non-peptide entities (e.g., carbohydrates) or linkers.

In certain embodiments, the amino acids represented by $XC_1C_2$ can complex with a metal ion having a square planar/pyramidal geometry. The metal ion can complex with the MAP tag through 2N:2S coordination. In general, suitable metal ions include, but are not limited to, ions of nickel, zinc, cobalt, platinum, and palladium.

Prior to complexation with a metal ion, the amino acids represented by $XC_1C_2$ are L-enantiomeric, or in the case of X, achiral. Upon complexation with a metal ion, one or more of the amino acids undergo a site-specific chiral inversion. For example, $LXLC_1LC_2$ can become $DXLC_1DC_2$ upon complexation with a metal ion provided X is a chiral amino acid. In another example, when X is an achiral amino acid, such as glycine, only $C_2$ can undergo the chiral inversion.

In one example, the NCC tripeptide contains all L-amino acids. Conversion to the D-containing form can occur after complexation with nickel resulting in inversion at two positions to produce a stable DLD-NCC-metal complex. In some examples, chiral inversion in NCC peptides occurs at the first and third carbon-α positions in the NCC sequence. The resulting DLD-peptide-metal complex is stable in aqueous solution and benefits from an increase in thermodynamic stability.

In another embodiment, the present disclosure provides methods and compositions for site-specific chiral inversion of amino acids that can be useful to protect against proteolysis.

In various embodiments, the resulting DLD-peptide is incorporated in a therapeutic peptide or protein. In various embodiments, D-amino acid containing peptides or proteins are resistant to degradation in-vivo. In various embodiments, the therapeutic peptide or protein comprising the DLD-peptide or achiral-L-D tripeptide has an increased half-life in-vivo.

In various embodiments, the invention is directed to methods of providing therapeutic peptides or proteins with increased half-lives in-vivo. In various embodiments, the method comprises providing a therapeutic peptide or protein comprising a MAP-tag as all L-enantiomers; exposing the MAP-tag to a metal under conditions such that the LLL-MAP-tag is converted to a DLD-tag; removing the metal; and isolating the resulting therapeutic peptide or protein to be administered to a subject in need thereof, wherein the therapeutic peptide or protein with a DLD-tag has increased resistance to proteolysis.

In various embodiments, the invention is directed to methods of providing therapeutic peptides or proteins with increased half-lives in-vivo. In various embodiments, the method comprises providing a therapeutic peptide or protein comprising a MAP-tag with a terminal L-enantiomer; exposing the MAP-tag to a metal under conditions such that the terminal L-amino acid is converted to a D-amino acid; removing the metal; and isolating the resulting therapeutic peptide or protein to be administered to a subject in need thereof, wherein the therapeutic peptide or protein with a terminal D-amino acid has increased resistance to proteolysis. Chiral inversion by the MAP-based chemistry can result in a mixture with greater than about 70%, greater than about 80%, greater than about 90%, greater than about 95%, or greater than about 99% enrichment in one D-amino acid over the corresponding L-amino acid. In various embodiments, the therapeutic protein with increased half-life in-vivo is insulin.

The MAP sequences can be 3 amino acids in length and can be included in longer polypeptides and proteins at the N-terminus, C-terminus, or any position in between. In certain embodiments, however, it can be advantageous for a MAP sequence to be present in a polypeptide or protein configuration that presents the MAP sequence for binding with a metal, such as being present in a linker region between two proteins or in an internal sequence within a protein. A MAP sequence also can be attached to a non-peptide entity (e.g., polymer, fluorophore, solid support, chemical linker, and the like). Additionally, more than one MAP sequence can be present on a particular molecule. In various embodiments, one or more MAPs are part of an antibody's protein sequence. In various embodiments, one or more MAPs are covalently linked to an antibody through amino acid side-chains of the antibody, through sugar moieties linked to the antibody, or through non-natural linkers such as polyethers.

Superoxide Dismutase Activity

Nickel superoxide dismutase, of which Ni-NCC is both a structural and functional mimic, is a complex enzyme with many factors governing its unique and efficient reactivity. In Ni-SOD, the amino acid residues involved in the mononuclear nickel binding site are found at the N-terminal end of the enzyme, comprising a nickel hook. The metal is bound in a 2N:2S, square planar nickel (II) geometry, utilizing two nonadjacent cysteine side chains, a backbone nitrogen, and the N-terminus as ligands. The presence of two cysteine ligands helps maintain the $Ni^{2+}/Ni^{3+}$ redox couple that is necessary to catalyze the disproportionation reaction. Without both cysteine amino acid residues, catalysis is not possible and coordination is a weak, octahedral arrangement. During catalysis, an axial histidine ligand is critical, to stabilizing the nickel (III) oxidized state and helping to tune the nickel redox potential for superoxide disproportionation; when the axial histidine is missing, the enzyme resides mostly in the nickel (II) (reduced) form, resulting in the rate of disproportionation decreasing by two orders of magnitude. Individual amino acid residues outside of the primary coordination sphere also impact reactivity. The primary coordination sphere determines the redox potential, which impacts reactivity, but larger structural differences and the secondary coordination sphere impact the reactivity without changing the redox potential.

Many complexes have been synthesized in attempt to maintain the reactivity of the enzyme in a simple, small-molecule based system to better understand how specific features of the enzyme facilitate catalysis. Ironically, the experiments that have probed the primary coordination sphere and the effect of individual ligands on redox potential and catalysis have produced diverse results. Two Ni complexes synthesized by Hegg et al. (Mathrubootham, V.; Thomas, J.; Staples, R.; McCraken, J.; Shearer, J.; Hegg, E. L. *Inorg. Chem.* 2010, 49, 5393, incorporated by reference) illustrate differences between amine/amide vs bis-amide species. In the bis-amide complex, the spectral features were shifted to higher energy and the system has a more negative oxidation potential. Peptide maquettes and other peptide-based mimics of Ni-SOD have provided a way to examine the reactivity of the enzyme, as individual components that contribute to reactivity can be modified. Shearer and coworkers (Neupane, K. P.; Shearer, J. *Inorg. Chem.* 2006, 45, 10552, incorporated by reference) have performed studies on maquettes of Ni-SOD. Studies on these maquettes have probed the role of N-terminal acetylation to check the importance of the mixed amine/amide coordination on the reactivity. When the maquette was acetylated to generate a bis-amide (versus not acetylated, with amine/amide coordination), the redox potential and superoxide scavenging activity of the complex changed. Like the synthetic complex, the spectral features are shifted to higher energy with bis-amide coordination. The acetylated maquette, however, has a quasi-reversible redox potential that is more positive compared to the amine/amide maquette.

In a 5-mer NCC system with two glycines preceding the NCC tripeptide, converting the amine/amide to bis-amide coordination shifts the spectral features to higher energy, but only modestly impacts superoxide scavenging activity and redox potential. Each of these systems have 2N:2S coordination, yet altering the nitrogen ligand composition leads to different outcomes, suggesting that even within the primary coordination sphere, features other than the ligand affect redox potential and catalytic activity. Despite amine/amide coordination, no chiral inversion has been observed in Ni-SOD or reported for peptide maquettes that contain the metal binding sequences that mimic the activity of Ni-SOD.

In various embodiments, the present invention relates to the use of various peptides with superoxide dismutase activity. In various embodiments, the superoxide dismutase activity of a metal-MAP complex in an in-vitro assay is at least about 50%, at least about 60%, at least about 70%, at least about 80%, at least about 90%, or at least about 100% of the superoxide dismutase activity of a wild-type or native enzyme. In various embodiments, the superoxide dismutase activity of a polypeptide, protein, glycoprotein, antibody, or other substrate with multiple metal-MAP complexes in an in-vitro assay is at least about 50%, at least about 60%, at least about 70%, at least about 80%, at least about 90%, or at least about 100% of the superoxide dismutase activity of a wild-type or native enzyme.

In one example, a MAP comprising the sequence peptide-Asn-Cys-Cys (NCC) can be formed through a reaction with IMAC resin-chelated nickel, which allows this NCC peptide to react with and abstract the metal, resulting in a high affinity Ni-peptide complex at neutral pH. The nickel-bound peptide, Ni-peptide-NCC, can contain a diamagnetic $Ni^{II}$ center bound in square planar geometry with 2N:2S coordination. In various embodiments, bound nickel cycles through $Ni^{II}$ and $Ni^{III}$ states.

In various embodiments, the structure of Ni-NCC has mixed amine/amide nitrogen coordination and cis deprotonated thiolates. Without wishing to be bound by theory, this coordination can resemble that of Ni in nickel superoxide dismutase (Ni-SOD), which can consist of two cysteinate sulfurs (Cys2 and Cys6) arranged cis to one another, the N-terminal amine, and the deprotonated amide nitrogen from the peptide backbone of Cys2. When bound to nickel, the tripeptide can act as a functional mimic of the enzyme nickel superoxide dismutase. Although a common function exists, the MAP amino acid sequence is not related to the sequence of the Ni-SOD enzyme participating in the same function.

In various embodiments, the Ni-MAP-tag peptide complex is part of a larger polypeptide, protein, glycoprotein, or antibody, and has superoxide dismutase activity without undergoing site-specific chiral inversion to DLD enantiomers. In various embodiments, the MAP-tag is XCC as all L enantiomers, where X is any amino acid. In various embodiments, the MAP-tag is NCC as all L enantiomers. The change from a mixed amine/amide in the MAP-tag to a bis-amide within a larger sequence only minorly impacts the superoxide scavenging activity and redox potential of the complex, but it substantially avoids the occurrence of chiral inversion. Without wishing to be bound by theory, the mechanism of chiral inversion in the Ni-NCC system aids in understanding the role of the nitrogen coordination on the electronic properties and chiral inversion aids in understanding how the exact chemical composition dictates electron transfer properties of the nickel metal center.

In various embodiments, a method is provided for treating a defect in superoxide dismutase in a subject in need thereof comprising administering a composition as disclosed herein to the subject. In various embodiments, one or more metal-MAP complexes are linked to a targeting moiety, such as an antibody. In various embodiments, Ni-MAP complex and/or proteins or polypeptides containing Ni-MAP complexes are used as models for Ni-SOD enzymes for in-vitro analysis or diagnosis.

Anti-Oxidant Active Agent

In certain embodiments, the present disclosure provides anti-oxidant compositions and methods. For example, the metal-MAP-tag complex has anti-oxidant properties. In various embodiments, the metal ion-MAP-tag complex is present as an active ingredient in a therapeutic or cosmetic composition. Such compositions can be targeted, or otherwise used, in applications or compositions benefiting from an anti-oxidant active agent. In various embodiments, one or more metal-MAP complexes are linked to a targeting moiety, such as an antibody. Linkage to the targeting moiety can be through a natural or non-natural linker such as a carbohydrate or polyether linker. In various embodiments, one or more metal-MAP complexes can be part of the primary sequence of a polypeptide, protein, glycoprotein, antibody, or other biologically-produced polymer.

In various embodiments, the metal-MAP complex has antioxidant activity and is administered to provide pain relief. While not wishing to be bound by theory, it is believed that the metal-MAP complex administered to provide pain relief interferes with or reduces the amount of reactive oxygen species present in-vivo. Reactive oxygen species are involved in pain feedback loops and signaling of inflammation in-vivo. In various embodiments, the metal-MAP complex is delivered to target and interfere with the pain feedback loop. In various embodiments, the metal-MAP complex provides an anti-inflammatory effect in-vivo or by in-vitro assay. In various embodiments, the metal-MAP complex reduces the amount of reactive oxygen species in-vivo or in an in-vitro assay. In various embodiments, the antioxidant activity is correlated to superoxide dismutase activity. In various embodiments, a method is provided for reducing pain and/or inflammation in a subject in need thereof comprising administering a composition as disclosed herein to the subject.

Dosing for the metal-MAP complex, in the methods of the invention can vary based on the subject. The dose can range from about $1 \times 10^{-10}$ g to about 5000 mg. Dose range can depend on the form of form and/or route of administration. For example, for systemic administration, non-limiting examples of dose ranges are, e.g. about 1 to about 5000 mg, or about 1 to about 3000 mg, or about 1 to about 2000 mg, or about 1 to about 1000 mg, or about 1 to about 500 mg, or about 1 to about 100 mg, or about 10 to about 5000 mg, or about 10 to about 3000 mg, or about 10 to about 2000 mg, or about 10 to about 1000 mg, or about 10 to about 500 mg, or about 10 to about 200 mg, or about 10 to about 100 mg, or about 20 to about 2000 mg, or about 20 to about 1500 mg, or about 20 to about 1000 mg, or about 20 to about 500 mg, or about 20 to about 100 mg, or about 50 to about 5000 mg, or about 50 to about 4000 mg, or about 50 to about 3000 mg, or about 50 to about 2000 mg, or about 50 to about 1000 mg, or about 50 to about 500 mg, or about 50 to about 100 mg, about 100 to about 5000 mg, or about 100 to about 4000 mg, or about 100 to about 3000 mg, or about 100 to about 2000 mg, or about 100 to about 1000 mg, or about 100 to about 500 mg. In some embodiments, the dose is about 100, about 200, about 300, about 400, about 500, about 600, about 700, about 800, about 900, or about 1000 mg. In some embodiments, the dose is 0.1 mg. In some embodiments, the dose is 1.0 mg. In some embodiments, the dose is about 10 mg. In some embodiments, the dose is about 100 mg. In some embodiments, the dose is about 500 mg. In some embodiments, the dose is about 1000 mg. All amounts are considered to be about the indicated amount.

Anti-Oxidant Preservative

In various embodiments, the present disclosure provides metal-MAP complexes as anti-oxidant ingredients in compositions. For example, the metal-MAP-tag complex has anti-oxidant properties which act as a preservative in the composition. Such compositions can be used in applications or compositions benefiting from an anti-oxidant component, which is not present in a therapeutically or cosmetically active amount. In various embodiments, the metal ion-MAP-tag complex is present in a therapeutic or cosmetic composition, wherein the metal ion-MAP-tag complex is present in an amount effective to provide anti-oxidant and/or preservative properties, where the metal-MAP-tag complex is not present as an active ingredient in the composition.

The metal-MAP complex can be used in combination with or in place of known preservatives, which can be used to form pharmaceutical compositions and dosage forms including, but not limited to, purite, peroxides, perborates, imidazolidinyl urea, diazolidinyl urea, phenoxyethanol, alkonium chlorides including benzalkonium chlorides, methylparaben, ethylparaben and propylparaben. In other embodiments, suitable preservatives for which the metal-MAP complex can be used in combination with or in place of include: benzalkonium chloride, purite, peroxides, perborates, thimerosal, chlorobutanol, methyl paraben, propyl paraben, phenylethyl alcohol, edetate disodium, sorbic acid, or Onamer M.

In some embodiments of the invention, metal-MAP complex can be employed at a level of from 0.004% to 0.02% w/v. In some compositions of the present application, the preservative can be employed at a level of from about 0.001% w/v to less than about 0.04% w/v, e.g. from about 0.001% w/v to about 0.008% w/v, or about 0.005% w/v. For example, formulations for application to skin can use metal-MAP complex at about 0.02% w/v or about 0.04% w/v. In some embodiments, a metal-MAP complex is used to replace other preservatives. In some embodiments, a metal-MAP complex is used in place of methyl paraben or propyl paraben such that formulations use methyl paraben or propyl paraben at less than 0.02% w/v. In some embodiments, these formulations use essentially no methyl paraben or no propyl paraben.

In some embodiments, the peptide is present in an amount from about 0.001% w/v to about 0.005% w/v, from about 0.001% w/v to about 0.01% w/v, from about 0.001% w/v to about 0.05% w/v, from about 0.001% w/v to about 0.1% w/v, from about 0.005% w/v to about 0.01% w/v, or from about 0.005% w/v to about 0.1% w/v.

Inflammation

In various embodiments, the present disclosure provides metal-MAP complexes as anti-inflammatories. A metal-MAP complex can be used to treat inflammation arising from a local response to cellular injury. A metal-MAP complex can be used to treat inflammation that is characterized by capillary dilatation, leukocytic infiltration, redness, heat, and/or pain. In some embodiments, a metal-MAP peptide can serve as a mechanism initiating the elimination of noxious agents and of damaged tissue associated with inflammation.

A metal-MAP peptide of the invention can be used to treat acute inflammation. Symptoms of acute inflammation can be present for a few days, or can persist for a few weeks. Symptoms can include redness, immobility, swelling, pain, discomfort, and heat. Examples of diseases, conditions, and situations which can be associated with acute inflammation include: acute bronchitis, infected ingrown toenail, sore throat from a cold or flu, a scratch/cut on the skin, exercise (especially intense training), acute appendicitis, acute dermatitis, acute tonsillitis, acute infective meningitis, acute sinusitis, or a bruise or abrasion.

A metal-MAP peptide of the invention can be used to treat chronic inflammation. Chronic inflammation can persist for months or even years. Symptoms of chronic inflammation can persist for months or years. Symptoms can include redness, immobility, swelling, pain, discomfort, and heat. Examples of diseases and conditions which can be associated with chronic inflammation include: asthma, chronic peptic ulcer, tuberculosis, rheumatoid arthritis, chronic periodontitis, ulcerative colitis and Crohn's disease, chronic sinusitis, and chronic active hepatitis.

Formulations

Administration of compositions or formulations containing the MAP of the present invention can be by any pharmaceutically- or cosmetically-acceptable route. For example, administration can be intravenous, intraperitoneal, intramuscular, topical, or any other route used for delivery of pharmaceutical or cosmetic compositions.

The compositions of the present invention comprise a pharmaceutically-acceptable excipient or carrier, which, as used herein, includes any and all solvents, diluents, or other liquid vehicle, dispersion or suspension aids, surface active agents, isotonic agents, thickening or emulsifying agents, preservatives, solid binders, and lubricants, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Some examples of materials which can serve as acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Injectable preparations, for example, sterile injectable aqueous or oleaginous suspensions can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions of the present invention can be formulated and employed in combination therapies. The compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. Therapies employed can achieve a desired effect for the same disorder (for example, an inventive composition can be administered concurrently with another agent), or they can achieve different effects (e.g., control of any adverse effects).

Kits are provided for carrying out the methods of administering the disclosed compositions to subjects and consumers in need thereof. Such kits can include a number of unit dosages, such as a 30-day supply, or a multi-course treatment regimen. Optionally associated with such container(s) can be a notice in the form prescribed by a governmental agency regulating the manufacture, use or sale of pharmaceutical or cosmetic products, which notice reflects approval by the agency of manufacture, use or sale for human administration.

In some embodiments, a kit includes written instructions on the use of the therapy. The written material can be, for example, a label. The written material can suggest conditions and methods of administration. The instructions provide the subject and the supervising physician with the best guidance for achieving the optimal clinical outcome from the administration of the therapy.

In some embodiments, the invention provides a use of a peptide and a metal in formulating a medicament for treating a defect in superoxide dismutase in a subject in need thereof, the medicament comprising: i) the peptide, wherein the peptide comprises a sequence $XC_1C_2$, wherein X is any natural or non-natural amino acid or amino acid analog, and further wherein $C_1$ and $C_2$ are each individually chosen from a cysteine and a sulfur-containing alpha or beta amino acid; and ii) the metal bound to the peptide.

In some embodiments, the invention provides a use of a peptide and a metal in treating a defect in superoxide dismutase in a subject in need thereof, wherein: i) the peptide comprises a sequence $XC_1C_2$, wherein X is any natural or non-natural amino acid or amino acid analog, and further wherein $C_1$ and $C_2$ are each individually chosen from a cysteine and a sulfur-containing alpha or beta amino acid; and ii) the metal is bound to the peptide.

In some embodiments, the invention provides a use of a peptide and a metal in formulating a medicament for reducing pain in a subject in need thereof, the medicament comprising: i) the peptide, wherein the peptide comprises a sequence $XC_1C_2$, wherein X is any natural or non-natural amino acid or amino acid analog, and further wherein $C_1$ and $C_2$ are each individually chosen from a cysteine and a sulfur-containing alpha or beta amino acid; and ii) the metal bound to the peptide.

In some embodiments, the invention provides a use of a peptide and a metal in reducing pain in a subject in need thereof, wherein: i) the peptide comprises a sequence $XC_1C_2$, wherein X is any natural or non-natural amino acid or amino acid analog, and further wherein $C_1$ and $C_2$ are each individually chosen from a cysteine and a sulfur-containing alpha or beta amino acid; and ii) the metal is bound to the peptide.

In some embodiments, the invention provides a use of a peptide and a metal in formulating a medicament for reducing inflammation in a subject in need thereof, the medicament comprising: i) the peptide, wherein the peptide comprises a sequence $XC_1C_2$, wherein X is any natural or non-natural amino acid or amino acid analog, and further wherein $C_1$ and $C_2$ are each individually chosen from a cysteine and a sulfur-containing alpha or beta amino acid; and ii) the metal bound to the peptide.

In some embodiments, the invention provides a use of a peptide and a metal in reducing inflammation in a subject in need thereof, wherein: i) the peptide comprises a sequence $XC_1C_2$, wherein X is any natural or non-natural amino acid or amino acid analog, and further wherein $C_1$ and $C_2$ are each individually chosen from a cysteine and a sulfur-containing alpha or beta amino acid; and ii) the metal is bound to the peptide.

Pharmaceutically Acceptable Salts

The invention provides the use of pharmaceutically-acceptable salts of any therapeutic compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, a iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Chemical Reagent

Enzymes, such as xanthine oxidase, horseradish peroxidase, chloroperoxidase, and alcohol oxidase, have been used to initiate polymerization reactions, including acrylamide and methacrylate chemistries, based on their ability to generate free radical species in solution. Enzymes, such as superoxide dismutase (SOD), have been used to control such reactions based on their ability to scavenge radical species. Without wishing to be bound by theory, it is believed that the metal-peptide complex can mimic SOD in controlling such reactions and/or the metal-peptide complex can be used to initiate such reactions.

Thus, in various embodiments, the metal-peptide complex according to the invention is used as a chemical reagent. In various embodiments, the metal-peptide complex is used as a reagent for scavenging superoxide. In various embodiments, the metal-peptide complex is used as a catalyst for scavenging superoxide in an industrial or laboratory process or chemical reaction. For example, in various embodiments, the metal-peptide complex according to the invention is used as a free-radical scavenger in a polymerization process.

In some embodiments, the metal-peptide complex according to the invention can be used to control polymerization reaction chemistry. In various embodiments, metal-peptide complex produces radical oxygen species, which can initiate a polymerization reaction.

In various embodiments, a method is provided for performing a chemical reaction, the method comprising contacting: i) a peptide comprising a sequence $XC_1C_2$, wherein X is any natural or non-natural amino acid or amino acid analog, wherein $C_1$ and $C_2$ are each individually chosen from a cysteine and a sulfur-containing alpha or beta amino acid, and wherein a metal is bound to the peptide; and ii) chemical starting materials, whereupon the chemical starting materials are combined into a product.

In some embodiments, the metal-peptide complex is used in catalytic amounts (for example, less than 1 equivalent) and/or in a catalytic cycle wherein active species are regenerated in situ in the absence of a quenching event. In some embodiments, the chemical starting materials are polymer precursors, i.e. monomers. In various embodiments, the metal-peptide complex is used to control the rate of a polymerization reaction, such as a (meth)acrylic-based polymerization reaction. Non-limiting examples of polymerization include radical, cationic, and anionic. Non-limiting examples of functional groups that can be polymerized include polyolefins, polyacetylides, polyesters, polyamides, polycarbonates, and polyurethanes.

In various embodiments, the metal-peptide complex according to the invention is used as a scavenger of cyanide anion.

Processes of Producing Maps

A MAP sequence of the present disclosure can be encoded in line with a gene or nucleotide sequence for expression using any recombinant technology system. Additionally, it can be incorporated into a peptide or protein using any synthetic or biosynthetic method for peptide or protein production.

Nucleic acids encoding polypeptides or polypeptide fusion proteins/chimeric proteins described herein can be used to construct recombinant expression vectors capable of expressing the polypeptides or polypeptide fusion proteins/chimeric proteins of the present invention. In some embodiments, nucleic acid constructs capable of expressing the protein constructs described herein comprise nucleotide sequences containing transcriptional and translational regulatory information and such sequences are operably linked to nucleotide coding sequences.

A large number of suitable vectors are known in the art. Selection of the appropriate vector can depend on 1) whether it is to be used for nucleic acid amplification or for nucleic acid expression, 2) the size of the nucleic acid to be inserted into the vector, and 3) the host cell to be transformed with the vector. A vector can contain various components specific to its function (e.g. amplification of nucleic acid or expression of nucleic acid) and the host cell for which it is compatible.

In some embodiments, host cells are capable of expressing one or more polypeptides or polypeptide fusion proteins/chimeric proteins described herein. The host cells of the present invention encompass cells in prokaryotic, eukaryotic, and insect cells. In some embodiments, host cells are capable of modulating the expression of the inserted sequences, or modifying and processing the gene or protein product in the specific fashion desired. For example, expression from certain promoters can be elevated in the presence of certain inducers (e.g., zinc and cadmium ions for metallothionine promoters). In some embodiments, modifications (e.g., phosphorylation) and processing (e.g., cleavage) of protein products are important for the function of the protein. Host cells of the present invention can have characteristic and specific mechanisms for the post-translational processing and modification of a protein. Suitable cell lines or host systems to ensure the correct modification and processing of the expressed protein are well known in the art. In some embodiments, host cells secrete minimal amounts of proteolytic enzymes. In some embodiments, host systems of viral origin are utilized to perform the processes described for host cells herein.

Various expression vector/host systems can be utilized equally well by those skilled in the art for the recombinant expression of polypeptides or polypeptide fusion proteins/chimeric proteins described herein. Such systems include but are not limited to microorganisms such as bacteria transformed with recombinant bacteriophage DNA, plasmid DNA or cosmid DNA expression vectors containing the desired nucleic acid sequence encoding polypeptides or polypeptide fusion proteins/chimeric proteins described herein; yeast transformed with recombinant yeast expression vectors containing the desired nucleic acid sequence encoding polypeptides or polypeptide fusion proteins/chimeric proteins described herein; insect cell systems infected with recombinant virus expression vectors (e.g., baculovirus) containing the desired nucleic acid sequence encoding polypeptides or polypeptide fusion proteins/chimeric proteins described herein; plant cell systems infected with recombinant virus expression vectors (e.g., cauliflower mosaic virus CaMV; tobacco mosaic virus, TMV) or transformed with recombinant plasmid expression vectors (e.g., Ti plasmid) containing the desired nucleic acid sequence encoding polypeptides or polypeptide fusion proteins/chimeric proteins described herein; or animal cell systems infected with recombinant virus expression vectors (e.g. adenovirus, vaccinia virus) including cell lines engineered to contain multiple copies of the nucleic acid sequence encoding polypeptides or polypeptide fusion proteins/chimeric proteins described herein, either stably amplified (e.g., CHO/dhfr, CHO/glutamine synthetase) or unstably amplified in double-minute chromosomes (e.g., murine cell lines).

In the case of cell or viral based samples, organisms can be treated prior to purification to preserve and/or release a target polypeptide. In certain embodiments, the cells are fixed using a fixing agent. In some embodiments, the cells are lysed. The cellular material can be treated in a manner that does not disrupt a significant proportion of cells, but which removes proteins from the surface of the cellular material, and/or from the interstices between cells. For example, cellular material can be soaked in a liquid buffer, or, in the case of plant material, can be subjected to a vacuum, in order to remove proteins located in the intercellular spaces and/or in the plant cell wall. If the cellular material is a microorganism, proteins can be extracted from the microorganism culture medium. Compositions and methods for polypeptide secreting microorganisms and other cell cultures are known in the art and can be applied when suitable. Alternatively, the polypeptides can be packed in inclusion bodies. The inclusion bodies can further be separated from the cellular components in the medium. In some embodiments, the cells are not disrupted. A cellular or viral polypeptide that is presented by a cell or virus can be used for the attachment and/or purification of intact cells or viral particles.

Polypeptides can also be synthesized in a cell-free system prior to extraction.

EXAMPLES

To facilitate a better understanding of the present invention, the following examples of specific embodiments are given. In no way should the following examples be read to limit, or to define, the entire scope of the invention.

Example 1

Generation of Metal Peptide Complexes.

The peptides NCC, GCC, and NCC with a d-cysteine in the middle position [ldl-NCC] were purchased from Genscript Corporation (Piscataway, N.J., USA). The NCC peptides with a d-cysteine in the third position [lld-NCC] and with both d-asparagine in the first position and d-cysteine in the third position [dld-NCC] were purchased from Neo-Peptide (Cambridge, Mass., USA). FIG. 1 panel A illustrates a general structure of a peptide comprising a metal abstraction peptide sequence NCC reacting with a metal ion (M) to form a metal-peptide complex. FIG. 1 panel B illustrates a Ni-GGNCC (SEQ ID NO: 1) peptide complex coordinated in a 2N:2S geometry with two amide backbone nitrogen atoms and two cysteine side chains. Nickel-peptide complexes were generated in aqueous solution at neutral to basic pH. Incubation of the peptide for approximately 30 minutes with immobilized metal affinity chromatography (IMAC) resin (GE Healthcare) charged with nickel ensured a clean reaction with no undesired side products and no free metal ions in solution, yielding a reddish-brown complex, varying slightly by the identity of the peptide. Aged Ni-NCC samples were allowed to age for >40 days.

CD and Absorption Studies.

A 1.5 mM solution of Ni-NCC was prepared in 50 mM potassium phosphate, pH 7.4, and used as is or sparged with argon. Immediately after incubation, samples were placed in a cuvette with a 1-cm path length and scanned from 800-300 nm using both absorption and CD spectroscopy. Samples were aged and monitored at various timepoints over the course of several days. Background scans of buffer alone were subtracted from each scan. Absorption studies were performed on an Agilent 8453 UV/Visible spectrophotometer. Circular dichroism analysis was performed on a J-815 (Jasco Corporation) spectropolarimeter. The CD data presented represent the average of at least five scans. To accurately control the time frame of Ni-NCC aging for activity assays, the complex also was formed in solution upon addition of one equivalent of $NiSO_4$.

MCD Experiments.

Samples of Ni-NCC were prepared in 50 mM potassium phosphate buffer at pH 7.4 sparged with argon. Solid sucrose was added as a glassing agent and the mixture was heated to form a saturated solution. CD spectra of sucrose-saturated samples demonstrated no significant changes in features compared with samples lacking sucrose, indicating that this procedure did not perturb the structures of the Ni-NCC complex. The samples were placed in an MCD cell and flash frozen in liquid $N_2$. Spectra were collected on a J-815 (Jasco Corporation) spectropolarimeter interfaced with a magnetocryostat (Oxford Spectromag 4000-8). To remove contributions from CD signals, MCD data represent difference spectra of accumulations at +7 and −7T. Because the signal intensities from paramagnetic species display inverse temperature dependence, spectra were collected at several temperatures.

Deconvolution of CD and Absorption Data.

Deconvolution of CD and absorption data was performed using Igor Pro (Wavemetrics). Iterative Gaussian deconvolutions were performed with a constant peak width of 1650 cm. Absorption band energies were kept within 10% of the corresponding CD bands due to the broad nature of the absorption spectrum.

ESI-MS.

Samples were diluted 100× in a 1:1 mixture of methanol/water and analyzed on an LCT Premier (Waters Corporation) operating in negative ion mode, as described previously.

Deuterium Exchange.

A solution of 50 mM potassium phosphate was prepared in $D_2O$ and adjusted with NaOD and DCl to a pD of 7.4. Samples of 1.5 mM NCC and GCC were prepared in this solution. Transmetallation was performed as described. After removal of the solid resin, 10 μL of the sample was back-exchanged into one mL of a 1:1 water/methanol mixture and analyzed using ESI-MS operating in negative ion mode. The original samples were then incubated for 24 hours and analyzed in the same manner.

Electrochemistry.

Electrochemical data were collected. A 3 mL sample of 3 mM Ni-NCC was prepared in 50 mM sodium borate at pH 10. CV data were collected with a CH1812C Electrochemical Analyzer potentiostat (CH Instruments) with a three-electrode setup (platinum working electrode, Bioanalytical Systems, Inc.; Pt auxiliary electrode; Ag/AgCl reference electrode) in a glass CV cell. Potential was applied from zero to 1.2 V with a scan rate of 0.2 V per second, and current was measured. The same experiment was attempted on a 3 mM Ni-NCC sample in 50 mM potassium phosphate at the same pH. The sample was incubated for 24 hours and analyzed again.

Coordination of Cyanide and IR Analysis.

Samples of Ni-NCC were prepared at a concentration of 3 mM in 50 mM sodium borate at pH 10 and 50 mM potassium phosphate at pH 7.4. A sample of Ni-NCC in phosphate buffer was incubated for 24 hours. One equivalent of potassium cyanide was added to each of the three Ni-NCC samples. Samples were flash frozen and lyophilized. IR analysis was performed to observe the cyanide peak in each sample. IR spectra were acquired from dry powder samples on a Perkin Elmer Spectrum 100 FT-IR spectrometer equipped with a universal ATR (Attenuated Total Reflection) sampling accessory. The spectrum of solid potassium cyanide was used to compare the shift of $\nu(C\equiv N)$ vibration from the free to the nickel-coordinated state.

Computations.

Spin-restricted density functional theory (DFT) computations were performed using ORCA 2.8.0 and employed the conductor-like screening model (COSMO) with an epsilon value of 80 to approximate water. Geometry optimizations used the BP86 functional and the aug-TZVP basis set (a triple-zeta basis set with diffuse and polarization functions). Because these computations employed the resolution of identity (RI) approximation, the TZV/J auxiliary basis set was also used. Single point and time-dependent DFT (TD-DFT) computations used the B3LYP functional and the aug-TZVP basis set. In order to evaluate if the inclusion of explicit water molecules H-bonded to charged groups gave rise to geometries markedly different than those obtained using COSMO, a water molecule was added to hydrogen bond with the C-terminal carboxylate in the LLL, DLD, and DDL models of Ni-NCC. Observations of differences in bond lengths of less than 0.015 Å support a conclusion that the use of COSMO is sufficient to account for major solvation effects in this system.

Ni-SOD Xanthine/Xanthine Oxidase Coupled Assay.

Ni-SOD activity was determined, except Ni-NCC was generated in situ using one equivalent $NiSO_4$. Ni-NCC was aged for 0-120 minutes, and the Ni-SOD activity was determined using the standard xanthine/xanthine oxidase method developed by Crappo and coworkers. All reagents were generated in 50 mM potassium phosphate, 100 μM EDTA reaction buffer at pH 7.8 except for Ni-NCC, which was generated in 50 mM potassium phosphate, pH 7.4. 600 μM cytochrome c from bovine heart (Sigma), 300 μM xanthine (Sigma) and enough xanthine oxidase from buttermilk (Sigma) to cause a change in absorbance at 550 nM of 0.02-0.04 AU per minute were added to a final volume of 300 μL with reaction buffer. The change in absorbance at 550 nm was monitored on a Cary 100 UV-Visible spectrophotometer (Varian). The assay was performed with 100 μM Ni-NCC.

Preparation and Spectroscopic Characterization of Ni-NCC.

Metal incorporation into the described complex was accomplished via transmetallation. Peptides were incubated with IMAC resin in either 50 mM potassium phosphate buffer at pH 7.4 or in 50 mM sodium borate at pH 10. Absorption and CD spectroscopies were utilized to characterize the Ni-NCC complex. Studies have shown that pH, ionic strength, and concentration of the metal-peptide complex do not change the spectral features of the system; however, these studies show that the initial spectra differ between buffer systems but later converge to a common final state. pH was not a factor in the differences between spectra, as Ni-NCC samples analyzed in phosphate buffer at pH 10 directly after incubation exhibited the same spectral features as those in phosphate buffer at pH 7.4.

Over time, the spectral features of Ni-NCC in phosphate buffer changed to resemble those in borate buffer, suggesting rearrangement to a more stable structure occurred. Although samples were prepared in sparged solutions, no further precautions were taken to avoid oxygen dissolution during aging. To ensure complete conversion, a Ni-NCC sample in phosphate buffer was aged in air for up to 90 days and analyzed again. ESI-MS of the Ni-NCC complex in various conditions demonstrated that the peptide mass did not change with the changes in spectral features (m/z=392.98), indicating a lack of oxidation of thiolate ligands. Varied pH did not affect the overall rate of the aging process. This suggests that the changes observed in the CD are due to more subtle changes about the metal center. A Ni-GCC sample was examined in the same manner to evaluate the influence of the chirality at the first position. Although the spectral changes for the two complexes are not identical, a similar perturbation of CD signals was observed for Ni-GCC over a comparable time frame.

Spectral Deconvolutions.

In contrast to the changes in the CD spectra of Ni-NCC, absorption spectra of Ni-NCC freshly prepared in phosphate buffer and that same sample aged for 40 days appeared nearly identical. Both feature a broad envelope centered at 21 000 $cm^{-1}$ ($\epsilon$=210 $M^{-1}$ $cm^{-1}$) with a higher energy feature at 29 000 $cm^{-1}$ ($\epsilon$=1400$^{-1}$ $cm^{-1}$). These data are consistent with both species having a four-coordinate $Ni^{II}$ center in an $N_2$:$S_2$ square planar geometry. To quantitatively evaluate the CD spectral changes, spectral deconvolutions of these data were performed to determine the energies and signs of the electronic transitions. Whereas freshly prepared Ni-NCC displays signals with positive sign at 18 900, 22 170, and 26 520 $cm^{-1}$, the spectrum of the aged sample shows negative bands at similar energies (Table 1). These transitions shift to slightly lower energies ($\Delta$~200-900 $cm^{-1}$) with age. Bands 1-4 of freshly prepared Ni-NCC were previously assigned as d-d transitions and their energies should be very sensitive to changes in geometry about the $Ni^{II}$ center. The observation that the energies of these bands shift by <900 $cm^{-1}$ upon aging demonstrates that fresh and aged Ni-NCC have nearly identical coordination environments. The major spectral perturbations are predominately due to changes in sign and intensity of CD features. These minor changes in the d-d transition energies (Table 1) along with the virtually identical absorption spectra of fresh and aged Ni-NCC demonstrate that the geometry and ligands of the $Ni^{II}$ center are unaltered and that neither dimerization of the complex nor oxidation of the thiolate ligand occurs.

TABLE 1

Table 1. Transition energies derived from Gaussian deconvoluted CD spectra of freshly prepared and aged Ni-NCC in phosphate buffer. Bands having opposite sign in the fresh and aged spectra are shown in italics.

| Band | Freshly Prepared Δε ($M^{-1}cm^{-1}$) | Freshly Prepared Energy ($cm^{-1}$) | Aged Δε ($M^{-1}cm^{-1}$) | Aged Energy ($cm^{-1}$) |
|---|---|---|---|---|
| 1 | −0.1 | 14200 | *a* | *a* |
| 2 | *−0.21* | *16270* | *0.04* | *16000* |
| 3 | *0.22* | *18900* | *−0.1* | *18000* |
| 4 | 0.64 | 22170 | −0.78 | 21600 |
| 5 | *−0.44* | *23900* | *0.7* | *22000* |
| 6 | *0.71* | *26520* | *−1.3* | *24800* |
| 7 | 1.1 | 28475 | 1.22 | 28450 |

*a*The low signal-to-noise ratio between 11 000 and 14 000 $cm^{-1}$ precludes reliable deconvolution within this spectral window.

Magnetic Circular Dichroism.

To investigate whether a paramagnetic, tetrahedral intermediate is formed, magnetic CD (MCD) experiments were performed. Previous MCD experiments have shown that the primary Ni-NCC species in borate buffer at pH 10 is largely diamagnetic, although a minor paramagnetic (S=1) species was present. Here, MCD experiments performed on a freshly prepared Ni-NCC sample demonstrated that the species initially present in phosphate buffer is also primarily diamagnetic; a minor paramagnetic component that accounts for less than 1% of the sample can reflect an intermediate state that does not accumulate. After aging, these temperature-dependent signals are no longer observed. Therefore, it can be concluded that aged Ni-NCC contains neither appreciable amounts of S=1 $Ni^{II}$ or S=½ $Ni^{III}$ centers. These data collectively show that both fresh and aged Ni-NCC contain diamagnetic $Ni^{II}$ centers. These data collectively show that both fresh and aged Ni-NCC contain diamagnetic $Ni^{II}$ in square planar geometries; the differences in spectral features and in reactivity between the freshly prepared and aged samples led to further investigation of the changes in the Ni-NCC complex.

Electrochemistry and Reactivity of Ni-NCC.

Electrochemical experiments have shown that Ni-NCC in borate buffer at pH 9.3 has a midpoint potential of 0.72 V (vs. Ag/Ag$^+$). When attempts to measure the midpoint potential of Ni-NCC in phosphate buffer at the same pH were made, the complex prepared in phosphate buffer did not exhibit a measurable potential; however, when the same sample was aged for 24 hours, the midpoint potential was comparable to that of the sample in borate buffer (0.71 V vs. Ag/Ag$^+$). Previous studies have shown that square planar geometries, for example peptide mimics of Ni-SOD, coordinate cyanide in an axial position, as determined by IR of the bound cyanide. Similarly, IR experiments have demonstrated that Ni-NCC in borate buffer is capable of coordinating CN in the axial position, as a shift in the ν (C≡N) vibration occurs. The IR spectrum of Ni-NCC freshly prepared in phosphate buffer did not exhibit a peak corresponding to coordinated cyanide; however, addition of cyanide after aging the sample overnight generated the expected peak for the coordinated state (Table 2). These data lend support to a slow structural rearrangement that occurs over the course of hours, resulting in a structure that allows for the interaction of a fifth ligand with the Ni-NCC complex.

TABLE 2

Table 2. IR data for cyanide coordinated to nickel.

| Species | ν(C≡N) ($cm^{-1}$) |
|---|---|
| NaCN | 2088 |
| $K_2[Ni(CN)_4]$ | 2123 |
| Ni(CN)-(mSOD) | 2108 |
| Ni-NCC + CN borate | 2109 |
| Ni-NCC + CN phosphate (fresh) | N/A |
| Ni-NCC + CN phosphate (aged) | 2107 |

Deuterium Exchange.

The flip in sign of CD signals suggests the structural change that allows for ligand binding can be due to chiral inversion. Because of this possibility, NCC was transmetallated with Ni-IMAC resin in buffers prepared in $D_2O$ to determine if deuterium would be incorporated into the peptide at any non-exchangeable site. After back-exchanging the Ni-NCC into 1:1 water/methanol to preserve the integrity of the complex but remove any exchangeable deuterium atoms, ESI-MS demonstrated incorporation of deuterium into two non-exchangeable positions (392.98 vs. 394.99). ESI-MS of the same reaction performed in $H_2O$ showed no difference in m/z over 24 hours. Because Ni-GCC shows a similar inversion of CD signals with time, but lacks chirality in the first position, Ni-GCC was also examined for deuterium exchange. Ni-GCC exhibited incorporation of deuterium into one non-exchangeable position, suggesting that the chirality of Asn in the first position and only one of the Cys is affected. This information was used to predict the possible location(s) of the incorporated deuterium atom(s).

Characterization of Peptides Containing D Amino Acids.

The LDL-Ni-NCC, LLD-Ni-NCC, and DLD-Ni-NCC complexes were generated and each analyzed using absorption and CD spectroscopies and ESI-MS. All of the complexes exhibit the same mass profile (m/z=392.98) in ESI-MS, suggesting that each forms 1:1 complexes with the metal. To determine the chirality of the final, stable Ni-NCC arrangement, CD spectra of each D-containing peptide were compared to the data collected for the aged (>40 days) Ni-NCC sample in phosphate buffer. The DLD-Ni-NCC spectrum overlaid with the aged Ni-NCC spectrum shows parallel features. These data indicate chiral inversion occurs at the first and third position within Ni-NCC to generate the DLD-Ni-NCC complex.

Whereas the spectral features of DLD-Ni-NCC do not shift or lose intensity with time, the CD spectrum of LLD-Ni-NCC evolves over time to look like that of DLD-Ni-NCC. In contrast, the CD spectrum of aged LDL-Ni-NCC looks like the mirror image of that of DLD-Ni-NCC. When the freshly prepared peptides were reacted with cyanide, only DLD-Ni-NCC was able to immediately coordinate cyanide in the axial position, providing further evidence that the DLD-form is the arrangement that aged Ni-NCC reaches over time.

DFT-Optimized Models and Computed Energies.

Computations were performed on models of Ni-NCC to explore the structural and energetic changes associated with chiral inversion of the different amino acid residues in the tripeptide-$Ni^{II}$ complex. These results are summarized in Table 3. In the optimized structure of LLL-Ni-NCC, the nickel (II) ion is bound in a near-square planar geometry. The coordination of the terminal amine, internal amide, and sulfur of Cys2 form two five-membered chelate rings that share a common edge. The sulfur of Cys3 coordinates trans to the amide nitrogen, which requires that the peptide wrap around the nickel center, thereby blocking one coordination site perpendicular to the square plane. The other open coordination site is partially blocked by the Asn side chain. These results suggest that the metal center can be sterically occluded in the LLL-peptide complex, explaining the lack of CN coordination observed in the freshly prepared samples described above.

The energies of Ni-NCC models with the chirality of different amino acids inverted show that inversion of Asn1 leads to a model (DLL-Ni-NCC) that is isoenergetic to that of LLL-Ni-NCC. In addition, the models in which Cys2 is inverted, LDL- and DDL-Ni-NCC, have an energetic destabilization of ~5 kcal/mol when compared to LLL-Ni-NCC. In contrast, when Cys3 is inverted, as in LLD- and DLD-Ni-NCC, an energetic stabilization of ~11 kcal/mol is predicted. Investigation into the role of solvation on the total energy of the conformers shows that although DLD-Ni-NCC does have an overall stabilization with respect to LLL-Ni-NCC in solvation energy, the relief of steric strain of the loop containing Cys3 has a more pronounced effect on the total energy. These results for DLD-Ni-NCC agree with the experimental data described above. The inversion from LLL-Ni-NCC to DLD-Ni-NCC opens one face of the $Ni^{II}$ ion to interact with exogenous ligands, consistent with the observation that aged Ni-NCC binds CN.

Studies performed in the absence of oxygen result in metal binding but chiral inversion does not occur. Introduction of oxygen into the Ni-NCC sample facilitated conversion to the DLD state. Therefore in addition to the metal being bound in the unique MAP configuration, an electron transfer agent, in this case derived from molecular oxygen, must be present in various embodiments for modulation of the peptide. The concentration or partial pressure of oxygen can be altered to alter the rate of the reaction.

Example 2

Preparation of $O_2$-Exposed Samples.

LLL-NCC was purchased as a lyophilized powder from GenScript, of higher than 85% purity, and stored desiccated at −20° C. when not in use. Authentic D-containing peptides, DLD-NCC, LLD-NCC, and DLL-NCC were purchased from NeoBioSci and were stored the same way. The peptide was reconstituted with 50 mM potassium phosphate buffer, generated from dibasic potassium phosphate (Fisher) and adjusted to the appropriate pH with either HCl or KOH. Following dissolution, 1.0 or 1.2 molar equivalents of $NiSO_4 \cdot 6H_2O$ (Fisher) in deionized water were added, and the

TABLE 3

Table 3. Bond lengths (Å) and relative energies (kcal/mol) of DFT-optimized models of $Ni^{II}$-NCC with amino acids of differing chiralities.

|  | LLL-Ni-NCC | DLL-Ni-NCC | LDL-Ni-NCC | LLD-Ni-NCC | DDL-Ni-NCC | DLD-Ni-NCC |
|---|---|---|---|---|---|---|
| Ni—$N_{amine}$ | 1.976 | 1.972 | 1.974 | 1.982 | 1.979 | 1.990 |
| Ni—$N_{amine}$ | 1.890 | 1.856 | 1.867 | 1.866 | 1.866 | 1.887 |
| Ni—$S_{cys2}$ | 2.222 | 2.184 | 2.165 | 2.179 | 2.164 | 2.196 |
| Ni—$S_{cys3}$ | 2.161 | 2.199 | 2.199 | 2.221 | 2.199 | 2.238 |
| Relative Energy | 0.0 | −0.3 | 4.7 | −11.6 | 5.1 | −11.1 |

TD-DFT Computations.

TD-DFT computations were performed to determine if the structural differences between LLL-Ni-NCC and DLD-Ni-NCC can account for the experimentally observed red-shift in the $Ni^{II}$ d-d transition energies upon aging of Ni-NCC. Because Ni—S bond lengths are frequently overestimated in DFT geometry-optimized models, it is expected that the predicted electronic transition energies for both Ni-NCC models will be computed at lower energy than experimentally observed. Nonetheless, this known shortcoming in DFT-computed Ni—S bond lengths will not hinder the analysis performed here, as the focus is on reproducing the relative shift in $Ni^{II}$ d-d transitions between LLL-Ni-NCC and DLD-Ni-NCC. For an S=0, $d^8$ metal ion in a square planar geometry, four d-d transitions are expected from excitation from each of the four doubly-occupied d orbitals to the unoccupied $d_{x^2-y^2}$ orbital. The computed relative energies of these transitions are shown in Table 3. Relative to LLL-Ni-NCC, all calculated d-d transitions for DLD-Ni-NCC are red-shifted, consistent with the experimental observation. This shift in transition energies is directly related to the energy of the $d_{x^2-y^2}$ orbital. In an idealized square planar geometry (e.g., $D_{4h}$ symmetry), the $d_{x^2-y^2}$ orbital is the dominant σ* orbital and is significantly destabilized relative to the remaining four d orbitals. As the geometry is perturbed from this limit, other d orbitals take on partial σ* character. This leads to the $d_{x^2-y^2}$ orbital being at a relatively lower energy and a red shift in d-d transitions. The nickel(II) coordination sphere in DLD-Ni-NCC is more distorted from square planar geometry than that of LLL-Ni-NCC, which gives rise to a smaller splitting between the $Ni^{II}$ d orbitals and thus red shifted d-d transitions.

solution was inverted to ensure good mixing, just before the sample was inserted into the spectrometer for analysis. Samples generated for spectroscopic analysis were generated with 1.2 molar equivalents of $Ni^{II}$ to ensure maximum complex formation, whereas those that were produced for nitroblue tetrazolium (NBT) and acetaldehyde assays were made with 1.0 molar equivalent of $Ni^{II}$ ion.

All pH values are given for the potassium phosphate solutions after addition of NCC and $NiSO_4 \cdot 6H_2O$. For the lower pH value (7), which is within the buffering capacity of potassium phosphate, addition of the peptide and metal solutions had minimal (<0.2) change to the solution pH. However, for the higher pH values (8 and 9), addition of NCC and $NiSO_4 \cdot 6H_2O$ solutions to pH 9.3 and 10.4 potassium phosphate solutions significantly dropped the pH, by 1.3 pH units. This is because complex formation produces four equivalents of protons and the higher pH value solutions are outside of the buffering range of potassium phosphate. All solutions at pH>7.3 were pH-adjusted just prior to sample generation and analysis.

Preparation of $O_2$-Free Samples.

Peptide was reconstituted in 50 mM potassium phosphate buffer of the designated pH and transferred to a quartz cuvette that was stoppered with a Suba-Seal septum and further sealed with parafilm. $NiSO_4 \cdot 6H_2O$ prepared in water was placed into a small vial secured with a septum and also sealed with parafilm. Samples were purged with 99.5% Ar that was itself purified by passage through columns of activated BASF catalyst and molecular sieves for 20-30 minutes to remove $O_2$. 1.2 equivalents of Ar-purged $NiSO_4 \cdot 6H_2O$ in water were transferred to the NCC solution using a gastight syringe. The septum was sealed with parafilm, the solution slowly agitated for ~2 minutes to ensure proper mixing, and then the cuvette was placed in the spectrometer for data collection and left for the duration of the experiment.

Electronic Absorption Spectroscopy.

Electronic absorption spectra were collected with either a Cary 50 or Agilent 5500 diode array ultraviolet-visible spectrophotometer. All spectra were collected in one cm path length quartz cuvettes with samples at room temperature. $O_2$-exposed samples were stirred during data collection using the interfaced Unisoku cryostat to promote efficient mixing. Ar-purged solutions were not stirred, but were inverted gently prior to data collected to promote efficient mixing. Spectra were collected every 0.1 min for the first 60 minutes and then every minute thereafter for a minimum of 167 minutes. To monitor formation of $Ni^{II}$-NCC for $O_2$-exposed samples, full-spectra were collected for a total of at least 167 minutes with a spectrum collected every second for the first hour and then attenuated by 1% for each data collection point following.

Nitroblue Tetrazolium Reduction Assay.

The nitroblue tetrazolium (NBT) assay was performed to detect the presence of the superoxide anion ($O_2^-$) during the chiral inversion reaction of Ni-NCC. Conversion of NBT (yellow) to its four-electron reduced form, diformazin (blue), results in an increase in absorption at 530 nm. $Ni^{II}$-NCC was generated by addition of one molar equivalent of 0.1 M $NiSO_4 \cdot 6H_2O$ in water to 3 mM NCC in pH 7.3 potassium phosphate buffer. The $Ni^{II}$-NCC mixture was briefly mixed to ensure homogeneity and then the appropriate volume of 12 mM NBT (Alfa Aesar) in pH 7.3 potassium phosphate buffer was added rapidly, to determine the effect of aging $Ni^{II}$-NCC on the oxidation of NBT to diformazin. Final concentrations of $Ni^{II}$-NCC and NBT were 0.75 mM and 0.15 mM respectively. Absorption spectra were collected to monitor the formation of diformazin over the course of one hour.

Carbanion Trapping with Acetaldehyde.

In order to determine if a carbanion is an intermediate en route to chiral inversion in Ni-NCC, the aging complex was treated with acetaldehyde (ACS Reagent Grade, ≥99.5%, Sigma-Aldrich) and the reaction was monitored via electrospray ionization mass spectrometry (ESI-MS) on an LCT Premier (Waters Corporation) instrument operated in the positive ion mode. It has been established that aldehydes can react with carbanion intermediates in solution, resulting in the formation of a product with an increased mass equivalent to that of the deprotonated aldehyde. For example, an increase of 43 m/z (the molecular mass of $CH_3CHO$ is 44 Da) indicates the quenching of a single carbanion unit using acetaldehyde. Therefore, the reaction of acetaldehyde with aging $Ni^{II}$-NCC via ESI-MS was monitored for the formation of a new major ion peak corresponding to an increased mass, indicating quenching of the carbanion and addition of the aldehyde to the ligand. $Ni^{II}$-NCC was treated with excess (>30 equivalents) acetaldehyde and the reaction was allowed to incubate for at least 24 hours at room temperature.

Circular Dichroism (CD) Spectroscopy.

CD spectra were collected on a Jasco J-815 spectropolarimeter, using samples generated in quartz cuvettes. Spectra were scanned between 300 and 900 nm (33 333 and 11 111 cm$^{-1}$) unless otherwise noted. Instrumental parameters included 0.5 s response, 0.2 nm data pitch, 500 nm/min scan rate, and 5 nm bandwidth. Spectra were collected every ten minutes for a total of 600 minutes (61 total spectra collected) unless otherwise noted.

$O_2$ Addition to $O_2$-Free Prepared Ni-NCC.

Solutions of $O_2$-free Ni-NCC were generated as described previously. The $Ni^{II}$-NCC sample was incubated $O_2$-free for 300 minutes, and monitored by CD spectroscopy, in order to ensure maximum $Ni^{II}$-NCC complex formation. $O_2$ was added to the sample via bubbling for one minute. Prior it its addition, the $O_2$ was stored in a balloon, over a column of DriRite. CD spectra were collected every ten minutes for the first 300 minutes and then 600 minutes following $O_2$ addition.

Compared to CD spectroscopy, electronic absorption offers a more straightforward method for monitoring the formation of the colored LLL-$Ni^{II}$-NCC complex from the colorless dilute $NiSO_4$ and NCC components, because, in principle, electronic absorption spectroscopy is insensitive to the chirality of the complex. A drop in extinction coefficient with time should be indicative of chiral inversion.

Scheme 1. Complex formation (1.1) and chiral inversion (1.2) reactions of $Ni^{II}$-NCC.

(1.1)

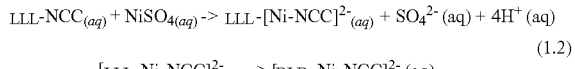

(1.2)

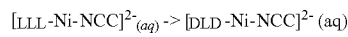

Formation of LLL-$Ni^{II}$-NCC Under $O_2$-Free Conditions.

Figure 2:
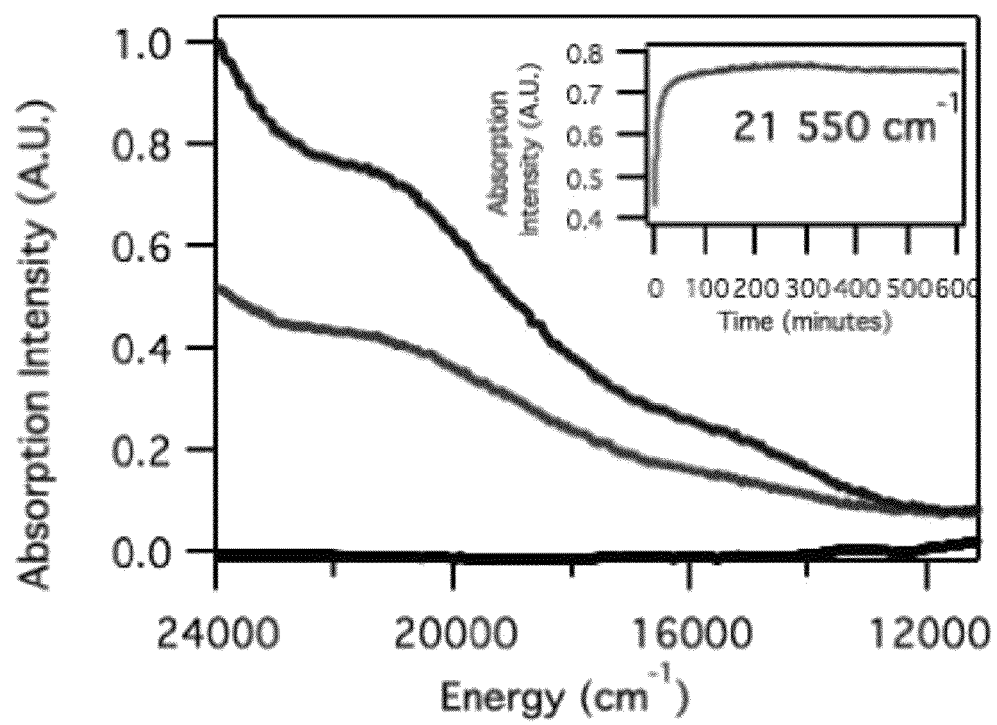
FIG. 2 shows electronic absorption spectra showing the formation of 0.75 mM LLL-Ni$^{II}$-NCC under O₂-free conditions in pH 7.3 50 mM potassium phosphate buffer. The spectra include LLL-NCC without metal (bottom trace), Ni-NCC shortly following addition of NiSO₄ to LLL-NCC (middle trace), and LLL-Ni$^{II}$-NCC incubated for ten hours (upper trace). Inset: absorption intensity at 21 550 cm$^{-1}$ as a function of time.

Electronic absorption data following the formation of 0.75 mM LLL-$Ni^{II}$-NCC under $O_2$-free conditions show a rise in absorption intensity in the visible and UV regions (FIG. 2) over time. The spectrum was collected approximately two minutes after metal was added to NCC in $O_2$-free solutions and represents the earliest accumulated data point for complex formation. The absorption intensity at 21 550 cm$^{-1}$ shows a rapid rise within the first minute of data collection and levels after 150 minutes (FIG. 2, inset). Attempts to model the kinetics of formation of LLL-$Ni^{II}$-NCC from $NiSO_4 \cdot 6H_2O$ and LLL-NCC to first-order or second-order rate equations were unsuccessful, given that complex formation likely involves several intermediate species. A drop in absorption intensity due to chiral inversion is not observed, as there is little change in absorption intensity after 150 minutes. In addition, the extinction coefficient observed under these $O_2$-free conditions is substantially greater than that for $O_2$-exposed LLL-$Ni^{II}$-NCC ($\epsilon_{21\,550}$=1 000 M$^{-1}$ cm$^{-1}$ for LLL-$Ni^{II}$-NCC formed $O_2$-free). The $\epsilon_{21\,550}$ for $O_2$-exposed LLL-$Ni^{II}$-NCC of 300 M$^{-1}$ cm$^{-1}$ is one-third that of the value above. See FIG. 2: Electronic absorption spectra showing the formation of 0.75 mM LLL-$Ni^{II}$-NCC under $O_2$-free conditions in pH 7.3 50 mM potassium phosphate buffer. The spectra include LLL-NCC without metal (dark), Ni-NCC shortly following addition of $NiSO_4$ to LLL-NCC (light), and LLL-$Ni^{II}$-NCC incubated for ten hours. Inset: absorption intensity at 21 550 cm$^{-1}$ as a function of time.

Formation of LLL-$Ni^{II}$-NCC in the Presence of $O_2$.

Figure 3:
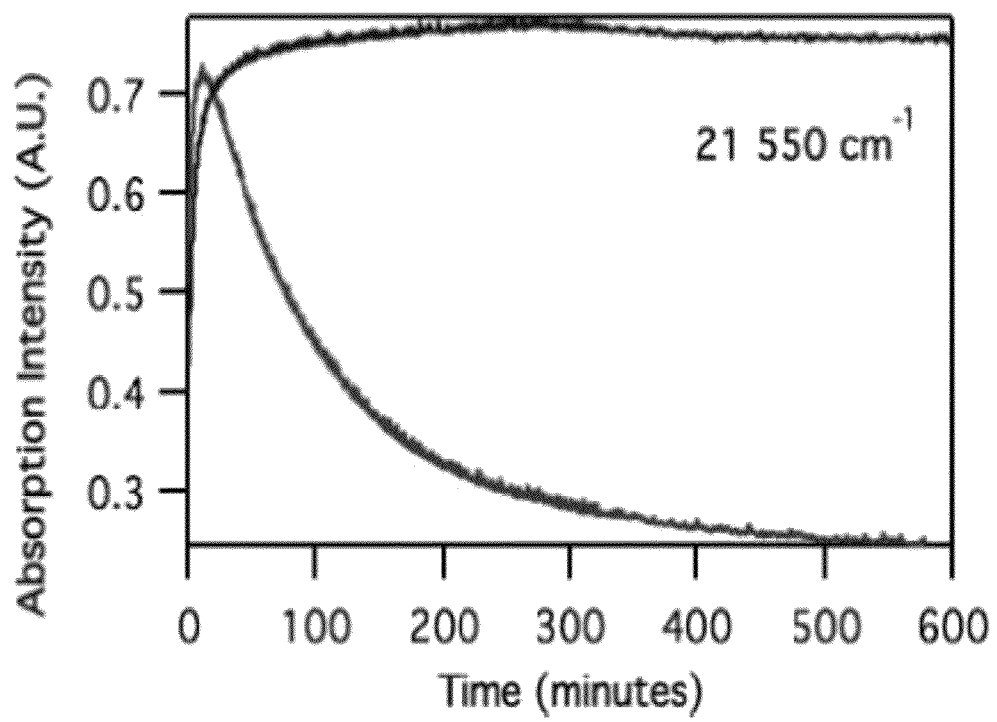
FIG. 3 shows single-energy time profile of electronic absorption spectra of 0.75 mM LLL-Ni$^{II}$-NCC prepared O₂-free (dark) and O₂-exposed (light) in pH 7.3 potassium phosphate buffer.

Upon addition of $NiSO_4 \cdot 6H_2O$ to NCC under an air atmosphere, the electronic absorption intensity rises rapidly to 0.75 AU within ten minutes (FIG. 3), indicating the formation of LLL-$Ni^{II}$-NCC in ~96% yield, using the extinction coefficient determined above. After ten minutes of aging, the absorption intensity at this wavelength drops rapidly, eventually leveling to 0.25 AU by ~500 minutes (FIG. 3). Assuming the chiral inversion of LLL-$Ni^{II}$-NCC is responsible for the drop in absorption intensity in the $O_2$-exposed sample, the inversion reaction proceeds rapidly following near full formation of the LLL-$Ni^{II}$-NCC only in the presence of $O_2$. See FIG. 3: Single-energy time profile of electronic absorption spectra of 0.75 mM LLL-$Ni^{II}$-NCC prepared $O_2$-free (dark) and $O_2$-exposed (light) in pH 7.3 potassium phosphate buffer.

The Chiral Inversion Reaction of LLL-$Ni^{II}$-NCC does not Occur in the Absence of $O_2$.

Figure 4:
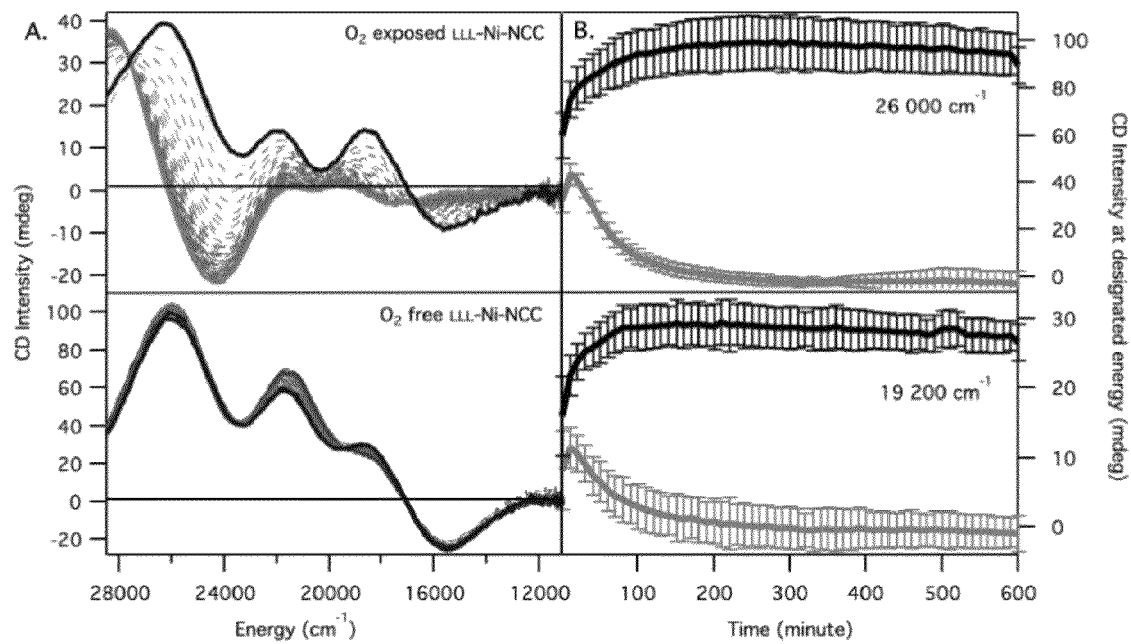
FIG. 4 panel A shows CD spectra of 0.75 mM LLL-Ni$^{II}$-NCC in pH 7.3 potassium phosphate buffer exposed to air (top) and purged with Ar (bottom). Spectra shown with a dark black line were obtained at the time the absorption spectra were at maximum intensity, indicating maximum LLL-Ni$^{II}$-NCC complex formation (t=10 minutes for O₂-exposed and t=150 minutes for O₂-free LLL-Ni$^{II}$-NCC). Spectra shown using a solid gray line were collected at t=590 minutes, and intermediate spectra obtained every ten minutes between these two times are represented as grey dotted traces. Panel B shows CD signal at single energies for 0.75 mM LLL-Ni$^{II}$-NCC incubated in O₂-free (black) and O₂-exposed (gray) pH 7.3 potassium phosphate buffer. Error bars represent +/- one standard deviation from an average of three trials.

CD spectra of LLL-$Ni^{II}$-NCC aged for 600 minutes under argon and air atmospheres are shown in FIG. 4. Spectra taken at maximum formation (t=10 minutes for $O_2$-exposed samples, t=150 minutes for $O_2$-free samples) are very similar but not identical. Both feature four prominent CD signals at 15 500 (−), 19 200 (+), 23 800 (+) and 26 000 $cm^{-1}$ (+). On the basis of a deconvolution of electronic absorption and CD spectra, these CD transitions are due to four d-d bands expected for a $Ni^{II}$ ion in a square planar geometry with 2N:2S ligand environment and three S—Ni charge transfer (CT) transitions. Starting at t=0 seconds, some increase in band intensity is initially observed, especially at 16 300, 18 900, 22 200 and 26 500 $cm^{-1}$, in both O2-free and $O_2$-exposed LLL-$Ni^{II}$-NCC, indicating complex formation (FIG. 4, panel B). Each band has a slightly different rate of change in formation, likely because LLL-$Ni^{II}$-NCC formation from LLL-NCC and $NiSO_4$ is not a two-state process and involves two or more intermediates. FIG. 4 panel A shows CD spectra of 0.75 mM LLL-$Ni^{II}$-NCC in pH 7.3 potassium phosphate buffer exposed to air (top) and purged with Ar (bottom). Dark spectra were obtained at the time the absorption spectra were at maximum intensity, indicating maximum LLL-$Ni^{II}$-NCC complex formation (t=10 minutes for $O_2$-exposed and t=150 minutes for $O_2$-free LLL-$Ni^{II}$-NCC), light spectra were collected at t=590 minutes, and intermediate spectra obtained every ten minutes between these two times are represented as grey dotted traces. FIG. 4, panel B shows CD signal at single energies for 0.75 mM LLL-$Ni^{II}$-NCC incubated in $O_2$-free (black) and $O_2$-exposed (lighter) pH 7.3 potassium phosphate buffer. Error bars represent +/− one standard deviation from an average of three trials.

The time-progression CD spectra of $O_2$-exposed LLL-$Ni^{II}$-NCC demonstrate distinct sign changes without significant band shifting, indicating chiral inversion of LLL-$Ni^{II}$-NCC. Major changes occur within the first 10 hours, where the absolute intensities of the bands at 16 000 and 23 000 $cm^{-1}$ decrease, and negative bands form at ~17 000 and 24 000 $cm^{-1}$. This CD spectrum does not look like that for DLD-$Ni^{II}$-NCC, but instead resembles that for LLL-$Ni^{II}$-NCC after 24 hours of aging. This ten-hour aged species represents either an intermediate, or a mixture of intermediate species, formed en route to DLD-$Ni^{II}$-NCC.

In contrast, the CD spectra collected for LLL-$Ni^{II}$-NCC prepared under an argon atmosphere offer no evidence of chiral inversion. The $O_2$-free sample does demonstrate a change in CD signal within the 600 minute time frame; however, these changes occur within the first 150 minutes and only lead to an increase in absolute ellipticity (FIG. 4, panel B, and FIG. 11); i.e., no change in sign of any CD features is observed. For $O_2$-free LLL-$Ni^{II}$-NCC, the individual time traces level after 150 minutes (FIG. 4, panel B), consistent with the time scale for formation of LLL-$Ni^{II}$-NCC from $NiSO_4.6H_2O$ and NCC established by the electronic absorption data described above. The intensities of the CD features for $O_2$-free LLL-$Ni^{II}$-NCC are approximately twice that of $O_2$-exposed LLL-$Ni^{II}$-NCC, suggesting that the CD spectrum of $O_2$-exposed LLL-$Ni^{II}$-NCC collected at t=10 minutes has contributions from multiple species. The CD spectrum for LLL-$Ni^{II}$-NCC prepared and aged under an Ar atmosphere thus represents the authentic CD spectrum of LLL-$Ni^{II}$-NCC; all previously reported spectra were complicated by the presence of additional species generated by this $O_2$-dependent reaction.

Addition of $O_2$ to LLL-$Ni^{II}$-NCC Prepared $O_2$-Free Induces the Chiral Inversion Reaction.

Figure 5:
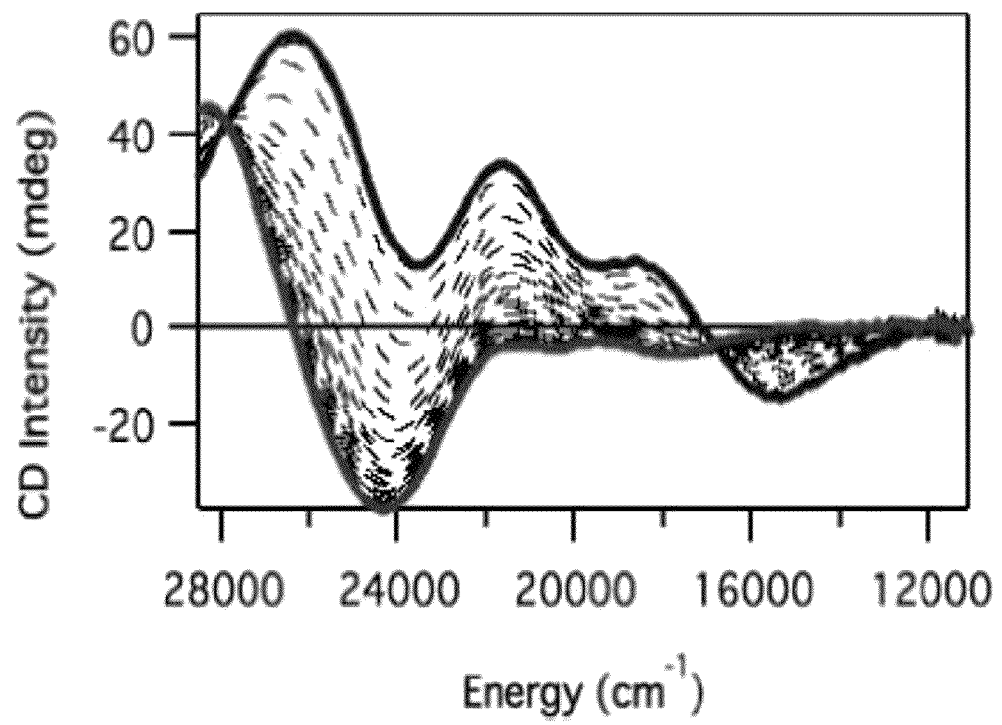
FIG. 5 shows CD spectra of 0.75 mM LLL-Ni$^{II}$-NCC generof $O_2$ exposure). Intermediate spectra obtained every ten minutes between these two times are represented as black dotted traces.

Conclusive evidence that $O_2$ causes the chiral inversion of LLL-$Ni^{II}$-NCC is provided by the observation of CD changes upon the addition of $O_2$ to $O_2$-free LLL-$Ni^{II}$-NCC. $O_2$ gas was added by a syringe to a sample of LLL-$Ni^{II}$-NCC that was prepared and incubated for 300 minutes under an Ar atmosphere to allow for maximum LLL-$Ni^{II}$-NCC formation. The CD spectrum of LLL-$Ni^{II}$-NCC prepared under an Ar atmosphere, then exposed to $O_2$ (FIG. 5), evolves in the same way as the $O_2$-exposed sample (FIG. 5 and FIG. 4, panel A, top), demonstrating that chiral inversion of LLL-$Ni^{II}$-NCC complex is completely dependent on $O_2$. See FIG. 5: CD spectra of 0.75 mM LLL-$Ni^{II}$-NCC generated $O_2$-free and incubated 300 minutes to achieve maximum formation of LLL-$Ni^{II}$-NCC, then treated with $O_2$. The dark spectrum was collected at t=300 minutes to allow for maximum complex formation, and then the sample was injected with $O_2$. The light spectrum was collected after 800 total minutes of incubation (600 minutes of $O_2$ exposure). Intermediate spectra obtained every ten minutes between these two times are represented as black dotted traces.

Superoxide is Formed by LLL-$Ni^{II}$-NCC Under an Atmosphere of Air.

The nitro blue tetrazolium (NBT) assay was employed to determine if the chiral inversion reaction of LLL-$Ni^{II}$-NCC involves reduction of $O_2$ to superoxide by the $Ni^{II}$ center. The assay detects formation of $O_2^-$, which oxidizes NBT to its four-electron oxidized species, diformazin, which absorbs strongly at 530 nm. Solutions containing the Ni-NCC complex and NBT absorbed more strongly at 530 nm than the control reactions, indicating the generation of superoxide under these conditions. In addition, monitoring the absorption at 530 nm over the course of an hour showed an increase in diformazin production, suggesting that superoxide forms as LLL-$Ni^{II}$-NCC undergoes chiral inversion.

LLL-$Ni^{II}$-NCC Forms Two Carbanion Intermediates En Route to Chiral Inversion.

Figure 12:
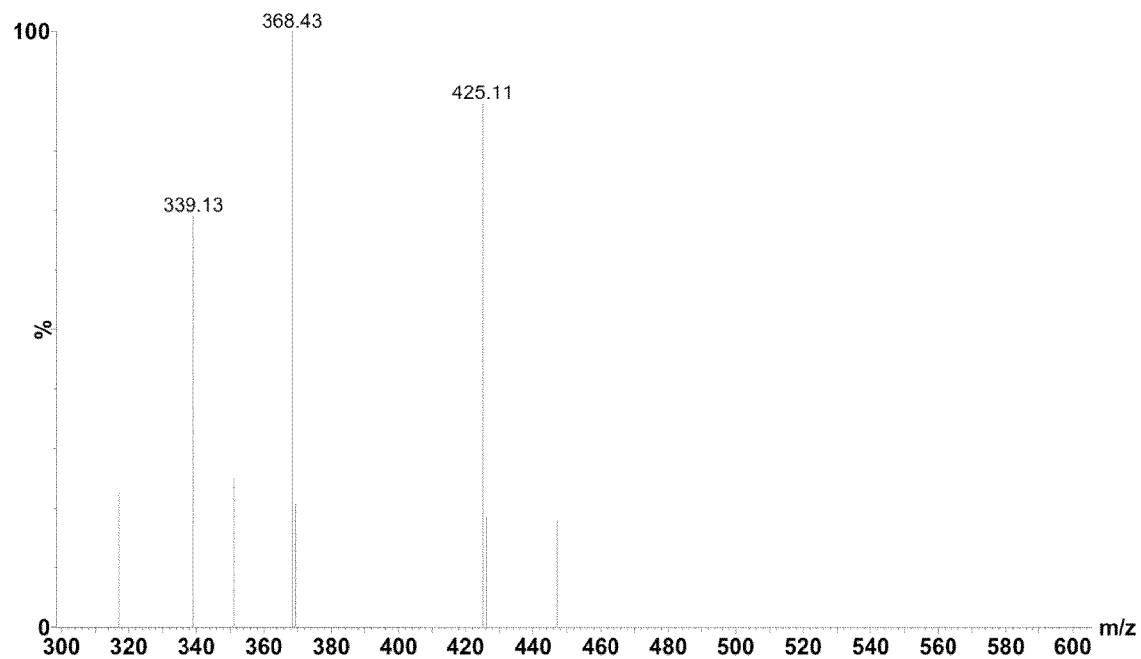
FIG. 12 shows ESI-MS spectrum of Ni-NCC incubated with excess acetaldehyde. The major ions include 339.13 m/z (NCC) and 425.11 m/z (NCC+2 acetaldehydes). The peak at 368.43 m/z is also found in samples without peptide and is therefore just due to the matrix and not the reaction of the aldehyde with the metal peptide complex.

LLL-$Ni^{II}$-NCC was incubated with excess acetaldehyde in order to determine if the chiral inversion reaction generates a carbanion intermediate. Aldehydes are known to quench carbanion intermediates in solution and generate a product with a mass increase equal to that of the deprotonated aldehyde. The reaction can be cleanly monitored using ESI-MS operated in positive ion mode. The spectra of LLL-$Ni^{II}$-NCC incubated with excess acetaldehyde over the course of a day clearly show both the free peptide (339 m/z) and NCC+2 acetaldehydes (425 m/z) (FIG. 12). These data indicate that over the course of 24 hours, two carbanion intermediates are formed per molecule of LLL-$Ni^{II}$-NCC. Therefore, each of the single chiral inversion reactions from LLL-Ni-NCC to DLD-Ni-NCC requires a carbanion intermediate.

The Chiral Inversion Reaction of LLL-$Ni^{II}$-NCC does not Show First Order Rate Dependence on Hydroxide Ion Concentration.

Figure 6:
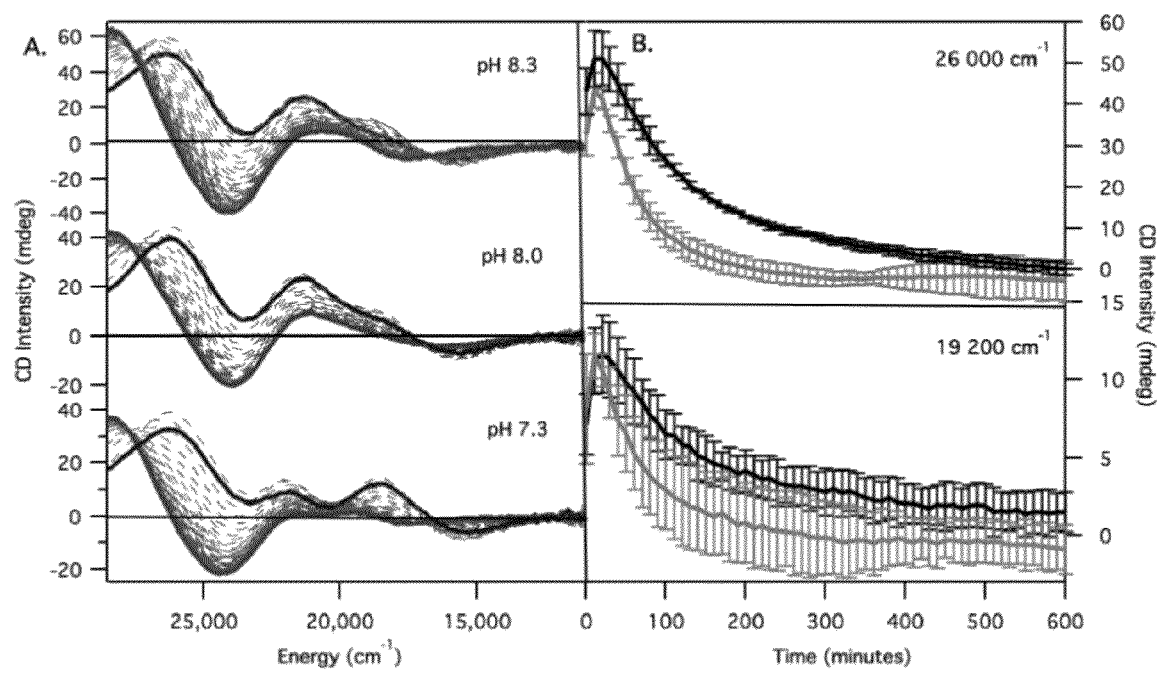
FIG. 6 panel A shows CD spectra of LLL-$Ni^{II}$-NCC in potassium phosphate buffer at pH 7.3 (bottom), pH 8.0 (middle), and pH 8.3 (top). The spectra shown with a black line were collected ~15 seconds after mixing, gray spectra were acquired after 600 minutes of incubation, and intermediate spectra obtained every ten minutes between the two time points are represented as black dotted traces. Panel B CD signal (mdeg) at designated single energies for pH 7.3 (gray) and pH 8.3 (black) potassium phosphate solutions. Error bars represent +/− one standard deviation from an average of three trials.

The chiral inversion of LLL-$Ni^{II}$-NCC was also followed for several different solution pH values, in order to determine the pH dependence of this reaction. The CD spectra of LLL-$Ni^{II}$-NCC aged in phosphate buffer at pH 7.3, pH 8.0, and pH 8.3 under an air atmosphere are shown in FIG. 6, panel A. For all three solutions, there is an initial increase in CD intensity, indicating LLL-$Ni^{II}$-NCC complex formation, followed by a change in sign of some CD signals, demonstrating the chiral inversion. Although the t=0 spectra are not identical for the three different samples (FIG. 6, panel A, dark), they all feature the same CD bands at the same energies, but of different intensities. This could be attributed to slightly different rates of formation and/or chiral inversion. The dependence on pH of the rate of chiral inversion is shown in FIG. 6, panel B, which compares the change in CD signals with time for samples at pH 7.3 and 8.3. While there is a modest dependence of the rate of change of the CD signal on the pH of the solution, a first-order dependence in this pH range was not observed. Additional experiments at even more elevated pH (>9.0) were performed, but the reproducibility of these results was poor. Without wishing to be bound by theory, it is thought that when the solution pH is well outside the buffering capacity of phosphate, slight changes in the amount of LLL-NCC or $Ni^{II}$ used in the experiment perturb the solution pH more significantly and therefore alter the aging progression profile of the complex. These data collectively demonstrate there is a minor pH effect on the rate of chiral inversion.

To assess whether inversion can occur at elevated pH in the absence of $O_2$, CD spectra were collected for pH 9.0 LLL-$Ni^{II}$-NCC prepared and aged under an Ar atmosphere. Under these conditions, the only changes observed in the CD spectra are attributed to complex formation (FIG. 13); there is no evidence for chiral inversion. Thus, regardless of whether the LLL-$Ni^{II}$-NCC is aged in neutral or basic solution, there is no chiral inversion observed in the absence of $O_2$. See FIG. 6, panel A. CD spectra of LLL-$Ni^{II}$-NCC in potassium phosphate buffer at pH 7.3 (bottom), pH 8.0 (middle), and pH 8.3 (top). Dark spectra were collected ~15 seconds after mixing, light spectra were acquired after 600 minutes of incubation, and intermediate spectra obtained every ten minutes between the two time points are represented as black dotted traces. See FIG. 6, panel B. CD signal (mdeg) at designated single energies for pH 7.3 (light) and pH 8.3 (dark) potassium phosphate solutions. Error bars represent +/- one standard deviation from an average of three trials.

DLD-$Ni^{II}$-NCC Shows Time-Dependent CD Changes.

Figure 7:
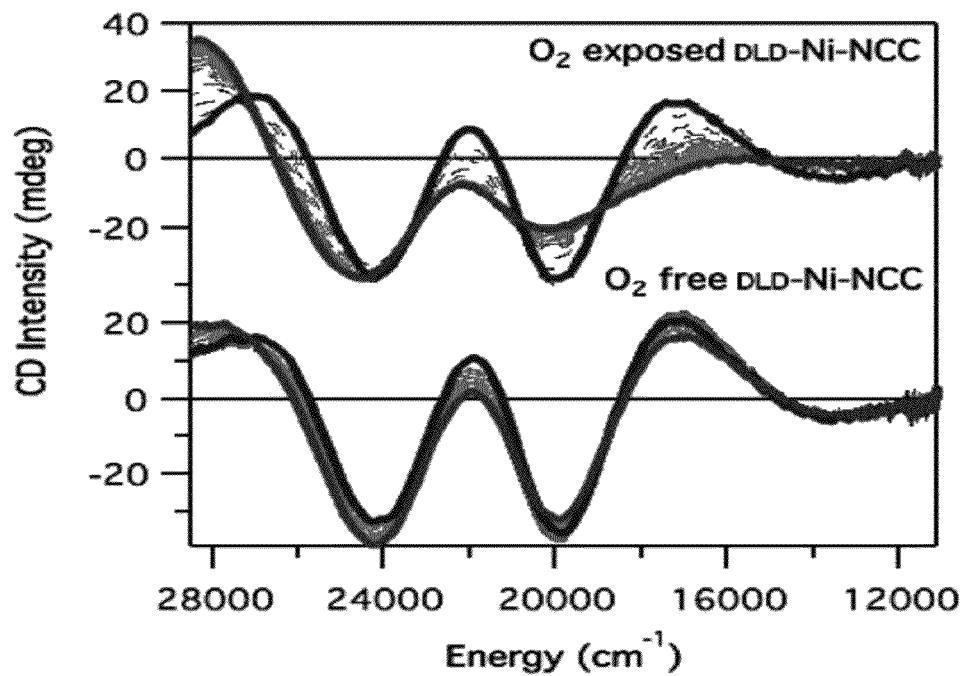
FIG. 7 shows CD spectra of DLD-$Ni^{II}$-NCC generated in pH 7.3 potassium phosphate buffer and prepared in the absence (bottom) and presence (top) of $O_2$. Spectra were collected at t=0 minutes (black), t=600 minutes (gray), and every ten minutes in between (dotted black traces).

The changes in the CD spectra of DLD-$Ni^{II}$-NCC aged under an Ar atmosphere are consistent with complex formation (FIG. 7, bottom). However, the final spectrum is distinct from that for DLD-$Ni^{II}$-NCC. Specifically, in the current spectrum, there is an additional positive feature at 17 000 cm$^{-1}$ not otherwise observed. The intensity of this positive feature decreases over time in the $O_2$-exposed sample (FIG. 7, top). Thus, CD data collected for DLD-$Ni^{II}$-NCC in the presence of $O_2$ are consistent with some extent of racemization, or secondary reaction. These changes were not detected because these modifications happened during the time-course of sample preparation. However, the ten-hour CD spectrum of $O_2$-exposed DLD-$Ni^{II}$-NCC is essentially identical to that for $O_2$-exposed LLL-$Ni^{II}$-NCC aged ~40 days. Thus, both LLL-, and DLD-$Ni^{II}$-NCC proceed to the same end point. See FIG. 7. CD spectra of DLD-$Ni^{II}$-NCC generated in pH 7.3 potassium phosphate buffer and prepared in the absence (bottom) and presence (top) of $O_2$. Spectra were collected at t=0 minutes (dark), t=600 minutes (light), and every ten minutes in between (dotted black traces).

Figure 8:
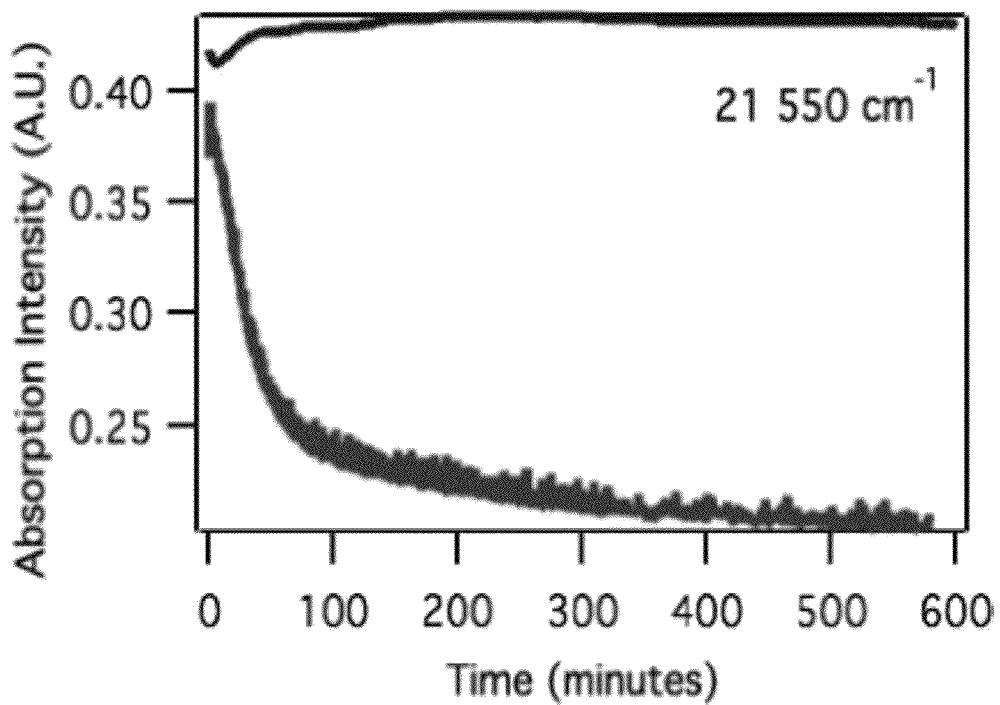
FIG. 8 shows single-energy time profile of electronic absorption spectra of DLD-$Ni^{II}$-NCC prepared $O_2$-free (black) and $O_2$-exposed (gray) in pH 7.3 potassium phosphate buffer.

Electronic absorption data collected for $O_2$-free and $O_2$-exposed DLD-$Ni^{II}$-NCC reinforce the CD data. In the absence of $O_2$, the electronic absorption intensity of DLD-$Ni^{II}$-NCC at 21 550 cm$^{-1}$ is essentially constant at 0.43 AU ($\epsilon$=570 M$^{-1}$ cm$^{-1}$) over the course of 600 minutes (FIG. 8). In contrast, in the $O_2$-exposed sample, the absorption intensity at 21 550 cm$^{-1}$ decreases rapidly from 0.40 to 0.20 AU over the course of ~100-200 minutes. See FIG. 8. Single-energy time profile of electronic absorption spectra of DLD-$Ni^{II}$-NCC prepared $O_2$-free (dark) and $O_2$-exposed (light) in pH 7.3 potassium phosphate buffer.

DLL-$Ni^{II}$-NCC Shows Time-Dependent CD Changes.

Figure 9:
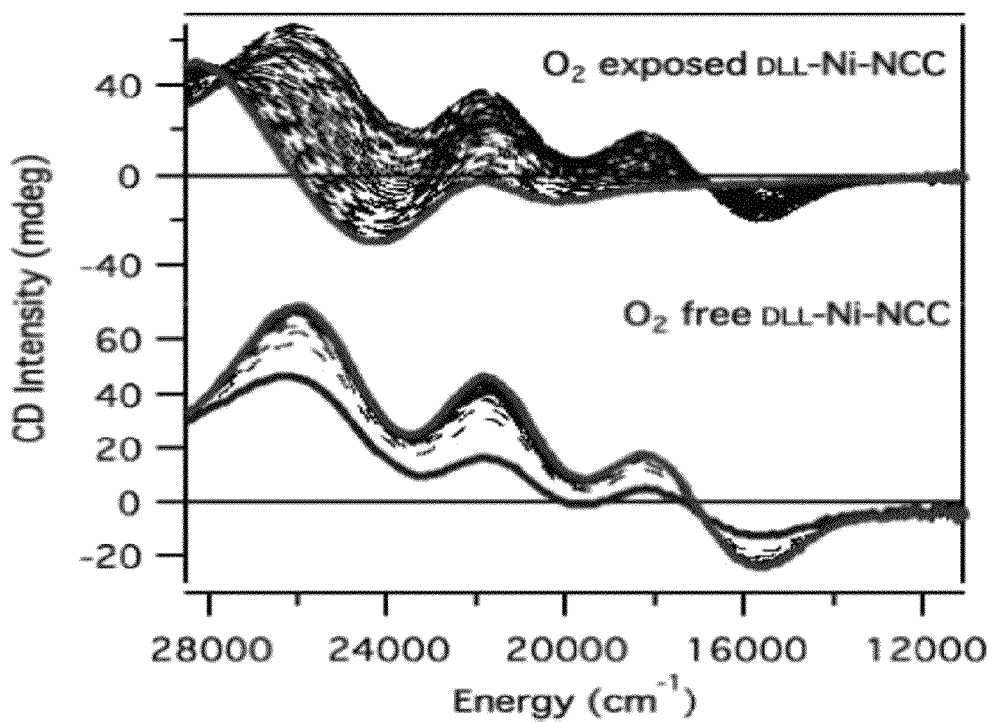
FIG. 9 shows CD spectra of DLL-$Ni^{II}$-NCC generated in pH 7.3 potassium phosphate buffer and prepared in the absence (bottom) and presence (top) of $O_2$. Spectra were collected at t=0 minutes (black), t=600 minutes (gray), and every ten minutes in between (dotted black traces).

The CD spectra of DLL-$Ni^{II}$-NCC are nearly identical to those of LLL-$Ni^{II}$-NCC (FIG. 4, panel A, and FIG. 9). Changes in the CD spectrum of DLL-$Ni^{II}$-NCC aged under an Ar atmosphere are consistent with complex formation (FIG. 9, bottom). In addition, the CD spectra of DLL-$Ni^{II}$-NCC generated in the presence of $O_2$ change to look like the spectrum of aged, $O_2$-exposed DLD-$Ni^{II}$-NCC over the course of 600 minutes (FIG. 9, top). Thus, DLL-$Ni^{II}$-NCC reached the final end point significantly faster than LLL-$Ni^{II}$-NCC. See FIG. 9. CD spectra of DLL-$Ni^{II}$-NCC generated in pH 7.3 potassium phosphate buffer and prepared in the absence (bottom) and presence (top) of $O_2$. Spectra were collected at t=0 minutes (dark), t=600 minutes (light), and every ten minutes in between (dotted black traces).

LLD-Ni-NCC Undergoes Spectral Changes, Even in the Absence of $O_2$.

Figure 10:
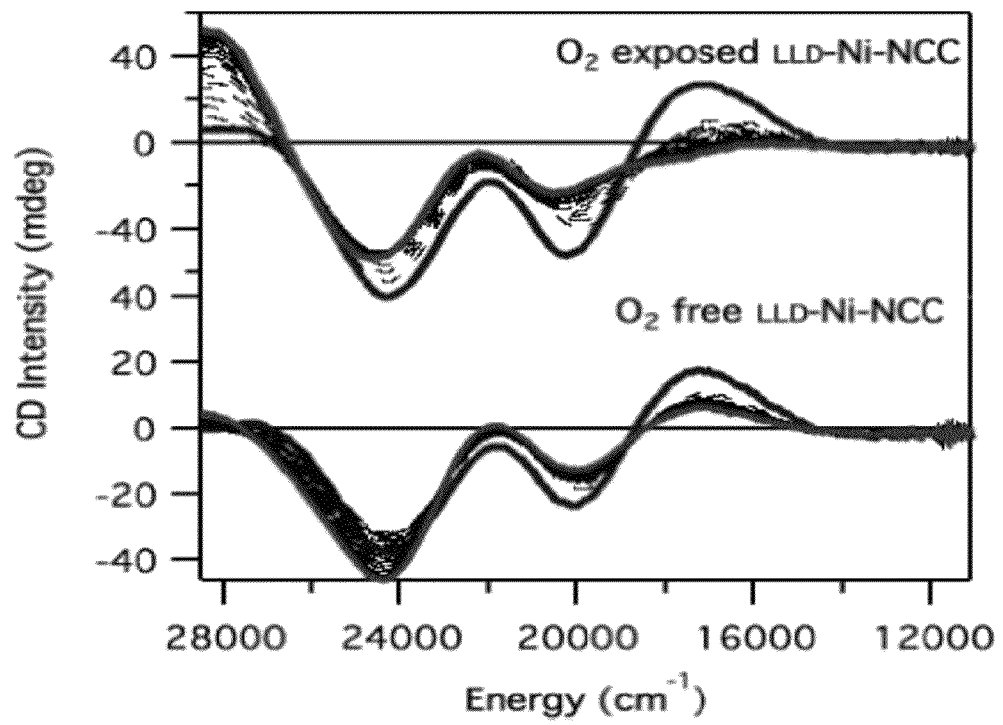
FIG. 10 shows CD spectra of LLD-$Ni^{II}$-NCC generated in pH 7.3 potassium phosphate buffer and prepared in the absence (bottom) and presence (top) of $O_2$. Spectra were collected at t=0 minutes (black), t=600 minutes (gray), and every ten minutes in between (dotted black traces).

In the absence of $O_2$, the initial CD spectra of LLD-$Ni^{II}$-NCC look similar to those of DLD-$Ni^{II}$-NCC (FIGS. 10 and 7). Moreover, when CD data are collected under an atmosphere of air, the CD features of LLD-$Ni^{II}$-NCC at ~17 000, 20 000, and 24 000 cm$^{-1}$ lose intensity, with the largest effect at the lowest energy band. However, unlike both LLL- and DLD-$Ni^{II}$-NCC, LLD-$Ni^{II}$-NCC shows spectral changes even in the absence of $O_2$ (FIG. 7, bottom). Given the nature of these spectral changes, this can indicate increased propensity for secondary reactions for the $Ni^{II}$-form of LLD-NCC. See FIG. 10. CD spectra of LLD-$Ni^{II}$-NCC generated in pH 7.3 potassium phosphate buffer and prepared in the absence (bottom) and presence (top) of $O_2$. Spectra were collected at t=0 minutes (dark), t=600 minutes (light), and every ten minutes in between (dotted black traces).

Figure 11:
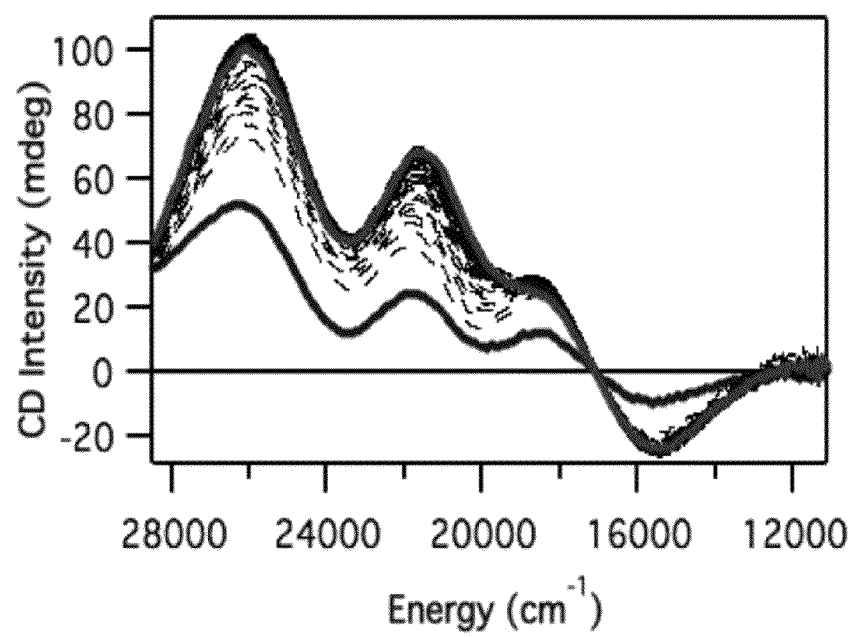
FIG. 11 shows CD spectra of $O_2$-free LLL-$Ni^{II}$-NCC collected for 600 minutes in pH 7.3 potassium phosphate buffer. Spectra include those for the sample at approximately two minutes after complex formation (light), after 300 minutes of incubation to represent maximum complex formation (dark), and after 600 minutes (medium). Spectra collected every ten minutes between the red and blue spectra are represented as black dotted lines and those collected between the blue and green spectra are shown as grey dotted lines.

FIG. 11 shows the CD spectra of $O_2$-free LLL-$Ni^{II}$-NCC collected for 600 minutes in pH 7.3 potassium phosphate buffer. Spectra include those for the sample at approximately two minutes after complex formation (light), after 300 minutes of incubation to represent maximum complex formation (dark), and after 600 minutes (medium). Spectra collected every ten minutes between the red and blue spectra are represented as black dotted lines and those collected between the blue and green spectra are shown as grey dotted lines.

FIG. 12 shows the ESI-MS spectrum of Ni-NCC incubated with excess acetaldehyde. The major ions include 339.13 m/z (NCC) and 425.11 m/z (NCC+2 acetaldehydes). The peak at 368.43 m/z is also found in samples without peptide and is therefore just due to the matrix and not the reaction of the aldehyde with the metal peptide complex.

Figure 13:
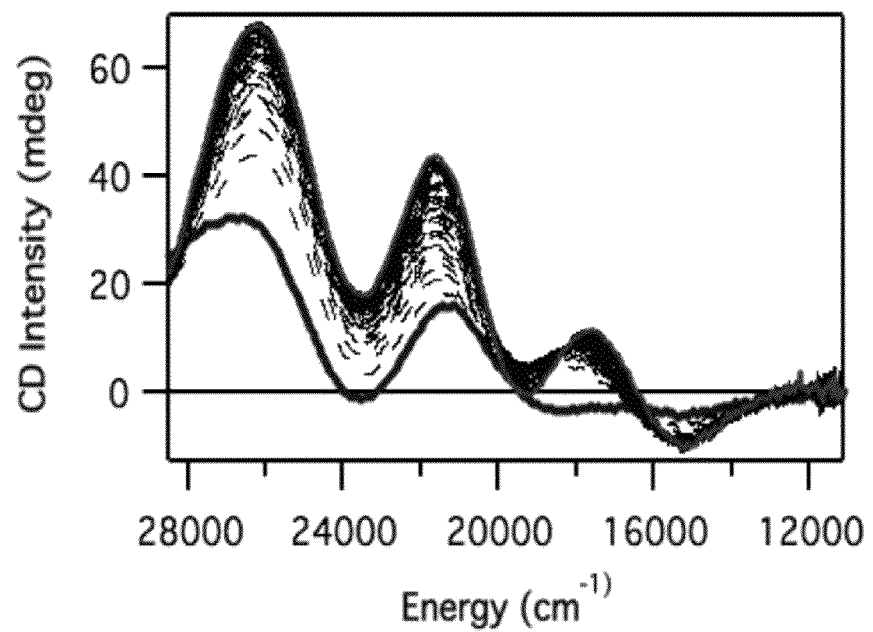
FIG. 13 shows CD spectra of $O_2$-free LLL-$Ni^{II}$-NCC collected for 600 minutes in pH 9.0 potassium phosphate. CD spectra of Ni-NCC in pH 9.0 potassium phosphate, prepared $O_2$ free. Spectra were collected after ~2 minutes (dark), following 600 minutes incubation (light), and every ten minutes in between (dotted black lines).

FIG. 13 shows the CD spectra of $O_2$-free LLL-$Ni^{II}$-NCC collected for 600 minutes in pH 9.0 potassium phosphate. CD spectra of Ni-NCC in pH 9.0 potassium phosphate, prepared $O_2$ free. Spectra were collected after ~2 minutes (dark), following 600 minutes incubation (light), and every ten minutes in between (dotted black lines).

The Effect of pH, Distinct Buffer Systems, and Aging on MAP Tag Peptide Binding.

Optically active amino acids and peptides are known to undergo racemization in aqueous solution in the absence of metal at temperatures above 100° C. and at pH values above 8 and below 5. Binding of a transition metal to the amino acid residues allows the process to occur under milder conditions. Metal-bound peptides are able to undergo racemization over the course of hours to days at temperatures between 35° C. and 40° C. and at a pH above 9. In both cases, the racemization or chiral inversion proceeds by deprotonation of an alpha hydrogen atom. Reprotonation by solvent gives either the D- or L-isomer. Coordination of the amino acid or peptide to a metal center renders the deprotonation event more thermodynamically favorable, leading to racemization or chiral inversion under milder conditions. In most cases where metal-facilitated chiral inversion occurs instead of racemization, steric factors promote the formation of the D-isomer over the L-form.

Figure 14:
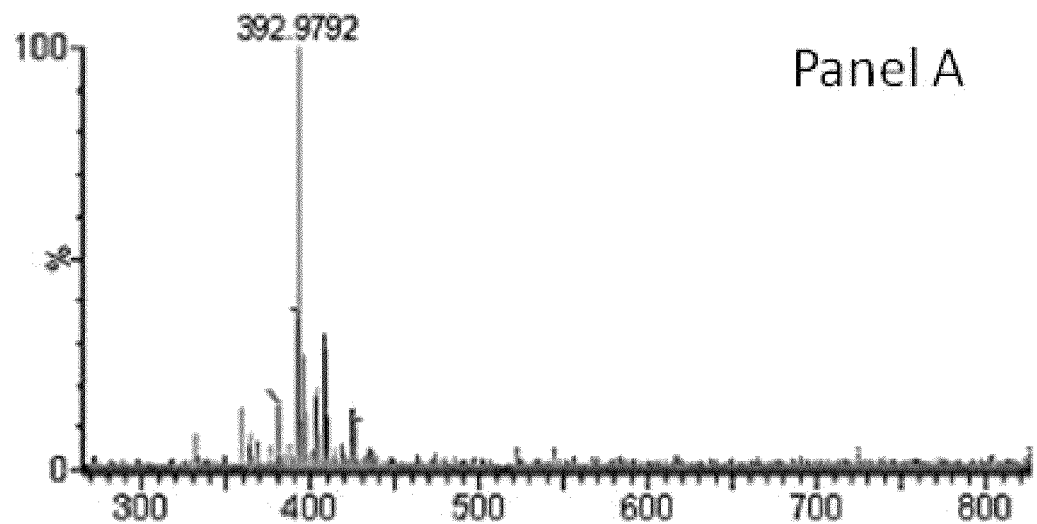
FIG. 14 panel A shows ESI-MS of the nickel-bound tripeptide acquired at pH 10, where the mass indicates that nickel is bound to the peptide. Panel B, shows ESI-MS spectrum after dropping the pH of the sample to 5, showing that nickel has been released from the peptide.
Figure 14:
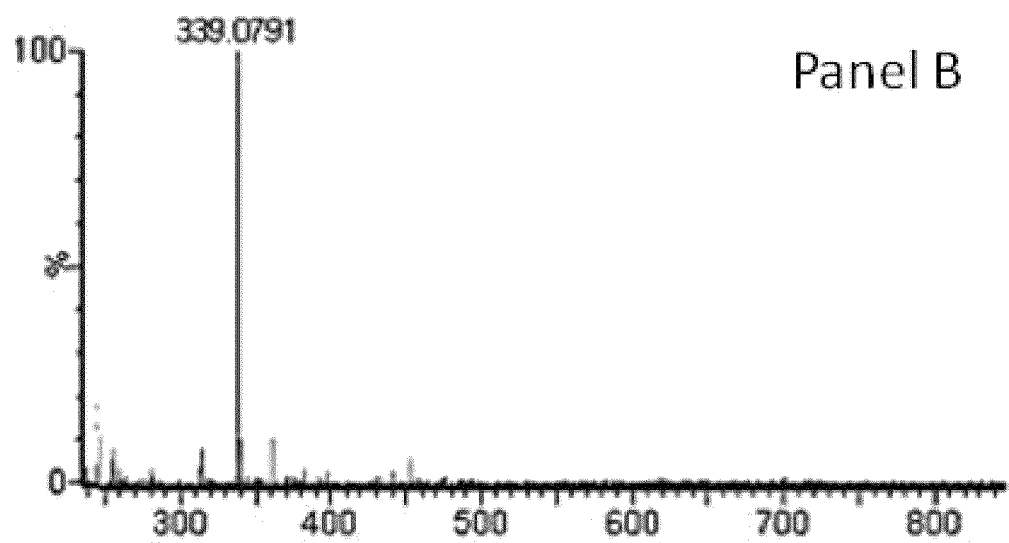

FIG. 14 is a representative figure of the effect of pH on a tripeptide sequence capable of abstracting a metal ion from a chelator and binding to it. Panel A shows ESI-MS of the nickel-bound tripeptide acquired at basic pH where the mass indicates that nickel is bound to the peptide. Panel B shows ESI-MS spectrum after dropping the pH to an acidic pH, showing that nickel has been released from the peptide.

Figure 15:
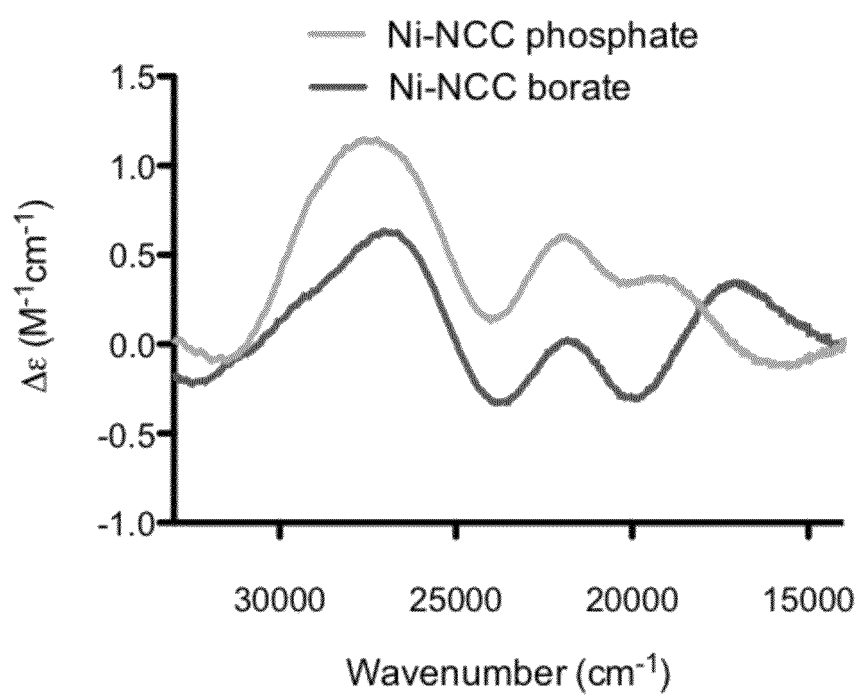
FIG. 15 shows that in different buffer systems, Ni-NCC has different CD spectral features.

In some embodiments, the initial spectra of Ni-NCC peptides in different buffer systems is different, but later converges to a common final state. FIG. 15 is a representative figure indicating that a tripeptide sequence capable of abstracting a metal ion from a chelator and binding to the metal can initially present different CD spectral features in different buffer systems, but later converges to a final state. FIG. 15 corresponds to the CD spectra of the Ni-NCC sequence in a phosphate (light line) and a borate (dark line) buffer system.

Figure 16:
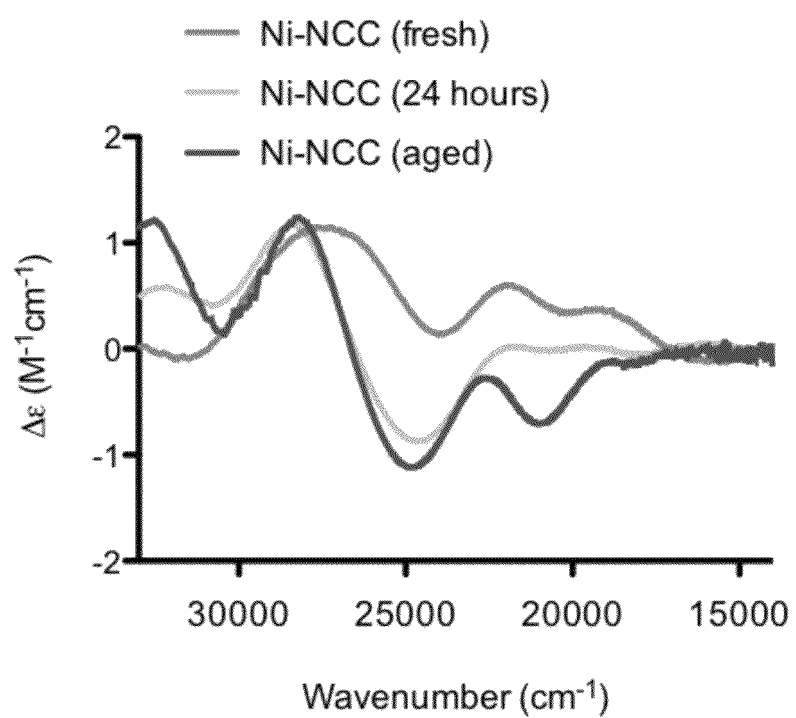
FIG. 16 shows an aging progression of Ni-NCC in phosphate.

In some embodiments, a Ni-NCC peptide complex rearranges over time to a more stable structure. FIG. 16 shows an aging progression of a general Ni-NCC tripeptide in phosphate buffer, where samples were prepared in sparged solutions, but no further precautions were taken to avoid oxygen dissolution during aging.

Figure 17:
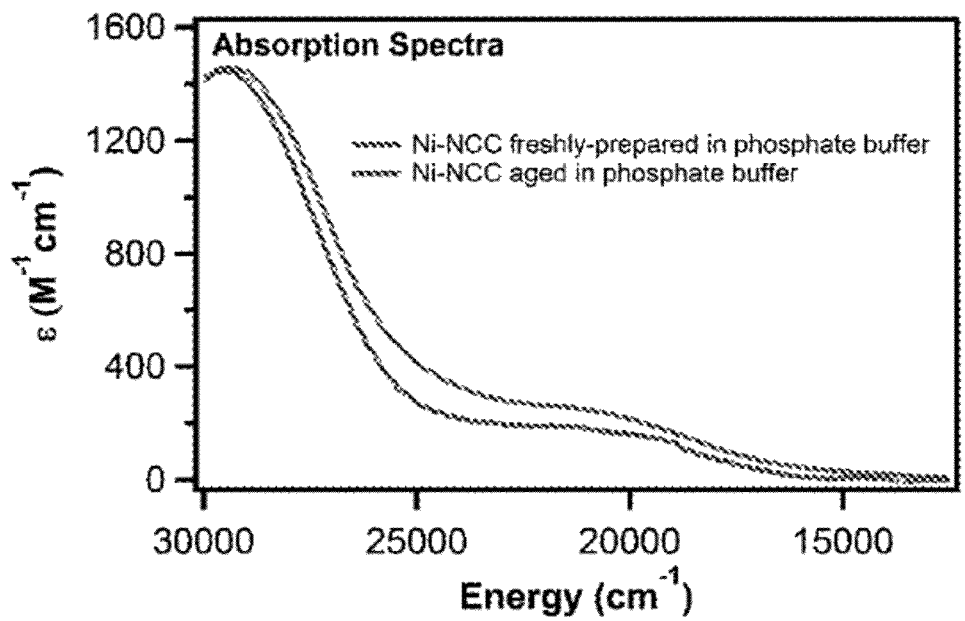
FIG. 17 panel A shows electronic absorption spectra of freshly prepared and aged Ni-NCC in 50 mM phosphate buffer at pH 7.4. Panel B shows CD spectra of the same samples. Individual Gaussian curves ( . . . ) and their sums ( - - - ) obtained from fits of the CD data are displayed.
Figure 17:
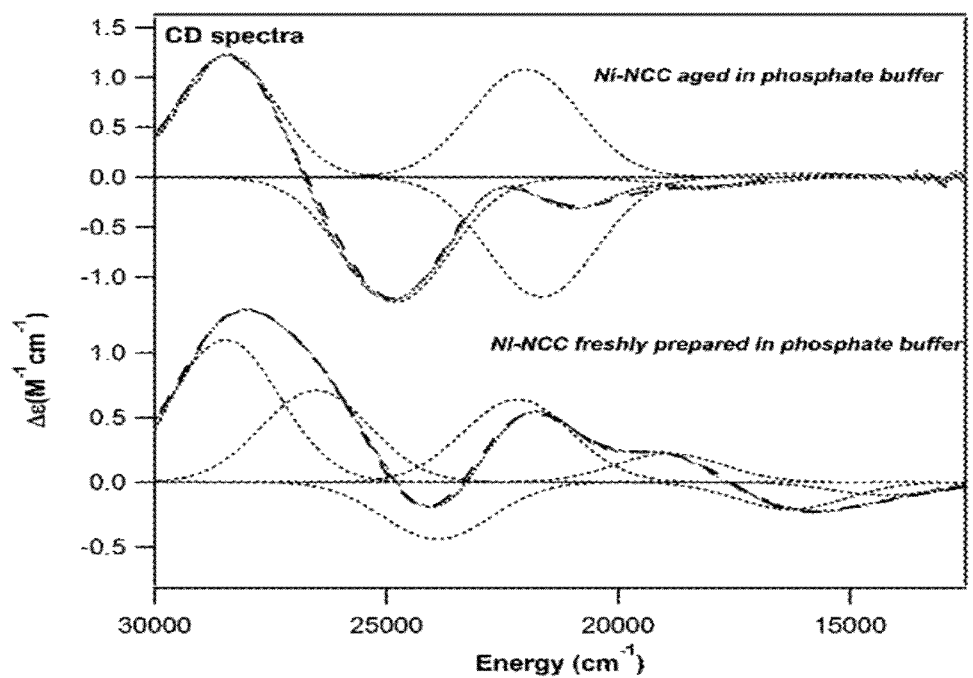

The effect of time and "aging" in the Ni-NCC geometry was investigated with electronic absorption and circular dichroism (CD) methods. The electronic absorption spectrum of a Ni-NCC peptide complex freshly prepared in phosphate buffer shows a similar pattern to the electronic absorption spectra of a Ni-NCC peptide complex aged for 40 days in phosphate buffer (FIG. 17, panel A). Both feature a broad envelope centered at 21000 cm$^{-1}$ ($\epsilon$=210 M$^{-1}$ cm$^{-1}$) with a higher energy feature 29000 cm$^{-1}$ ($\epsilon$=1400 M$^{-1}$ cm$^{-1}$). These data can be consistent with both species having a four-coordinate Ni$^{II}$ center in an N2:S2 square planar geometry. Spectral deconvolutions of these data were performed to determine the energies and signs of the electronic transitions (FIG. 17 panel B).

In addition to promoting racemization or inversion, the coordination of peptides to metals is also known to facilitate peptide degradation and/or oxidation. One example of this is the nickel complex of the tripeptide glycine-glycine-L-histidine, Ni-GGH. Ni$^{II}$-GGH has been studied for its ability to catalyze site-specific oxidation and cleavage of DNA, as well as peptide crosslinking. However, oxidation of Ni$^{II}$-GGH by O$_2$ generates Ni$^{III}$-GGH, which undergoes spontaneous decarboxylation at the C-terminus of the peptide. The decarboxylated product undergoes further reactivity including hydroxylation and racemization. Additional Ni$^{III}$-mediated reactivity in peptides includes ligand oxidation and disulfide bond formation/peptide crosslinking.

O$_2$-Dependent Chiral Inversion of Ni-NCC.

In the absence of O$_2$, LLL-Ni$^{II}$-NCC forms rapidly from Ni$^{II}$SO$_4$ and NCC, and this complex is stable for at least ten hours, showing no evidence of inversion or secondary reactions, even at pH 9.0. This is in contrast to other square planar Ni$^{II}$-peptide complexes that readily undergo base-catalyzed, metal-facilitated racemization at pH≥9 over the course of several hours to days. The lack of chiral inversion in LLL-Ni$^{II}$-NCC under anaerobic conditions is attributed to the presence of two anionic cysteinate ligands and one anionic amide ligand. Charge donation from these ligands is expected to reduce the Lewis acidity of the Ni$^{II}$ center, mitigating the ability of the metal to promote deprotonation of the C$\alpha$—H groups. A complementary rationale is that the anionic ligands, along with the deprotonated carboxylate group, give Ni$^{II}$-NCC an overall charge of −2, which would disfavor deprotonation on electrostatic grounds. This same behavior is observed for DLD-Ni$^{II}$-NCC, which is also unchanged for at least ten hours when under an Ar atmosphere.

In the presence of O$_2$, LLL-Ni$^{II}$-NCC shows fairly rapid spectroscopic changes that are consistent with inversion (or racemization) of the NCC peptide. On the basis of trapping experiments with acetaldehyde, two carbanions are formed during the O$_2$-dependent inversion. Studies of the inversion reaction at pH 7.3-8.3 reveal a minor increase in the rate of inversion as the pH is increased. These data are consistent with inversion proceeding by C$\alpha$—H deprotonation, but this deprotonation does not occur for LLL-Ni$^{II}$-NCC. In addition, another step must impact the rate of inversion more significantly than C$\alpha$—H deprotonation. The evidence for superoxide formation, as well as the O$_2$ dependence of this reaction, suggest that LLL-Ni$^{II}$-NCC reacts with O$_2$ to form superoxide and LLL-Ni$^{III}$-NCC. The higher oxidation state Ni$^{III}$ center promotes C$\alpha$—H deprotonation, leading to inversion (or racemization) for LLL-Ni$^{III}$-NCC upon reprotonation. Subsequent reaction of superoxide, or some alternative reductant, with Ni$^{III}$-NCC, would regenerate the Ni$^{II}$ form of NCC. Perpendicular-mode X-band EPR spectra collected for frozen aliquots of LLL-Ni$^{II}$-NCC during the aging process showed a very weak feature whose position and lineshape are consistent with a NI$^{III}$ center, albeit in very low concentration.

Pathway to Chiral Inversion in Ni-NCC.

Over the course of ~40 days, LLL-Ni$^{II}$-NCC evolved to a species, or two or more species, with a CD spectrum most similar to that of DLD-Ni$^{II}$-NCC. This directed inversion was rationalized on the basis of DFT-computed energies of models of Ni$^{II}$-NCC (Scheme 2). The CD spectra of LLD-Ni$^{II}$-NCC that developed over time was similar, but not identical, to the CD spectrum of DLD-Ni$^{II}$-NCC. The same was true for DLL-Ni$^{II}$-NCC. Thus, regardless of the entry point to the cycle shown in Scheme 2, the final spectra of all species are most similar to that of DLD-Ni$^{II}$-NCC. DLD-Ni$^{II}$-NCC evolved over time when exposed to O$_2$, although the change is significantly more minor than that observed for LLL-Ni$^{II}$-NCC (FIGS. 7 and 4).

Scheme 2. Pathway to chiral inversion in Ni-NCC, with DFT-computed relative energies of each model shown. All energy values are given relative to that of LLL-Ni$^{II}$-NCC, whose energy is defined as 0 kcal/mol.

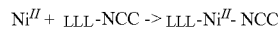 (2.1)

Ni$^{II}$ + LLL-NCC -> LLL-Ni$^{II}$-NCC

 (2.2)

LLL-Ni$^{II}$-NCC -> DLL-Ni$^{II}$-NCC (-0.3 kcal/mol)

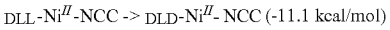 (2.3)

DLL-Ni$^{II}$-NCC -> DLD-Ni$^{II}$-NCC (-11.1 kcal/mol)

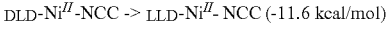 (2.4)

DLD-Ni$^{II}$-NCC -> LLD-Ni$^{II}$-NCC (-11.6 kcal/mol)

According to the DFT-computed energies (Scheme 2), the inversion of Asn1 results in very little change in energy (2.2), whereas inversion of Cys3 leads to a stabilization of −11 kcal/mol (2.2 and 2.3). The accuracy of DFT-computed energies at this level of theory is ~3-5 kcal/mol. CD spectra show a prominent positive band at ~17 000 cm$^{-1}$, whereas this band disappears with time in the O$_2$-exposed samples (FIGS. 7 and 9). LLD-Ni$^{II}$-NCC shows some spectral changes in the absence of O$_2$, suggesting that this isomer can be reactive even in the Ni$^{II}$ oxidation state. The O$_2$-dependent conversion of DLD-Ni$^{II}$-NCC to LLD-Ni$^{II}$-NCC, followed by the formation of some secondary product from the latter complex, could account for the spectral changes observed for O$_2$-exposed DLD-Ni$^{II}$-NCC. Thus, the likely end point in the cycle shown in Scheme 2 is DLD-Ni$^{II}$-NCC in the presence of secondary products that represent a small population of the sample.

Figure 18:
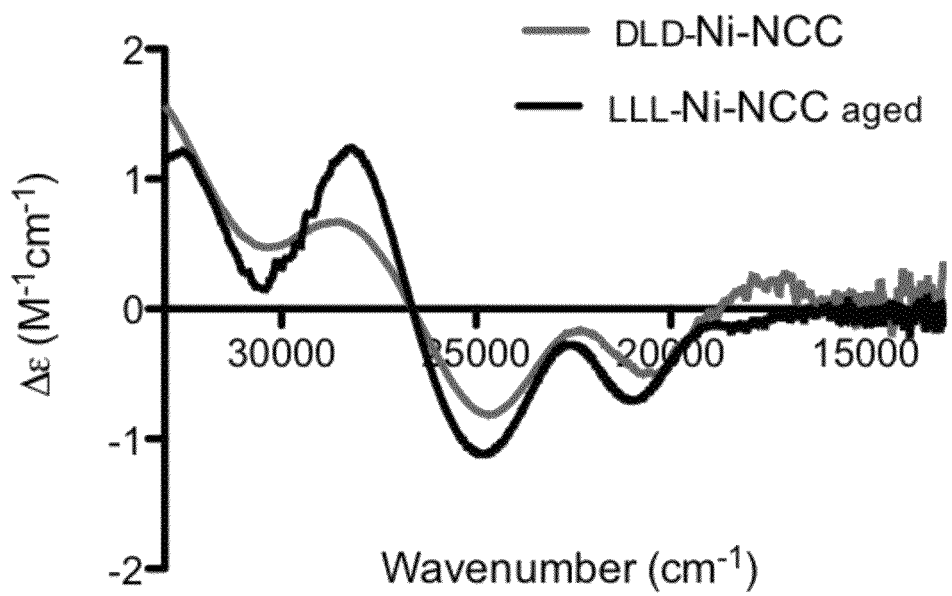
FIG. 18 shows CD spectra of Ni-NCC aged in phosphate buffer vs. DLD-Ni-NCC.
Figure 19:
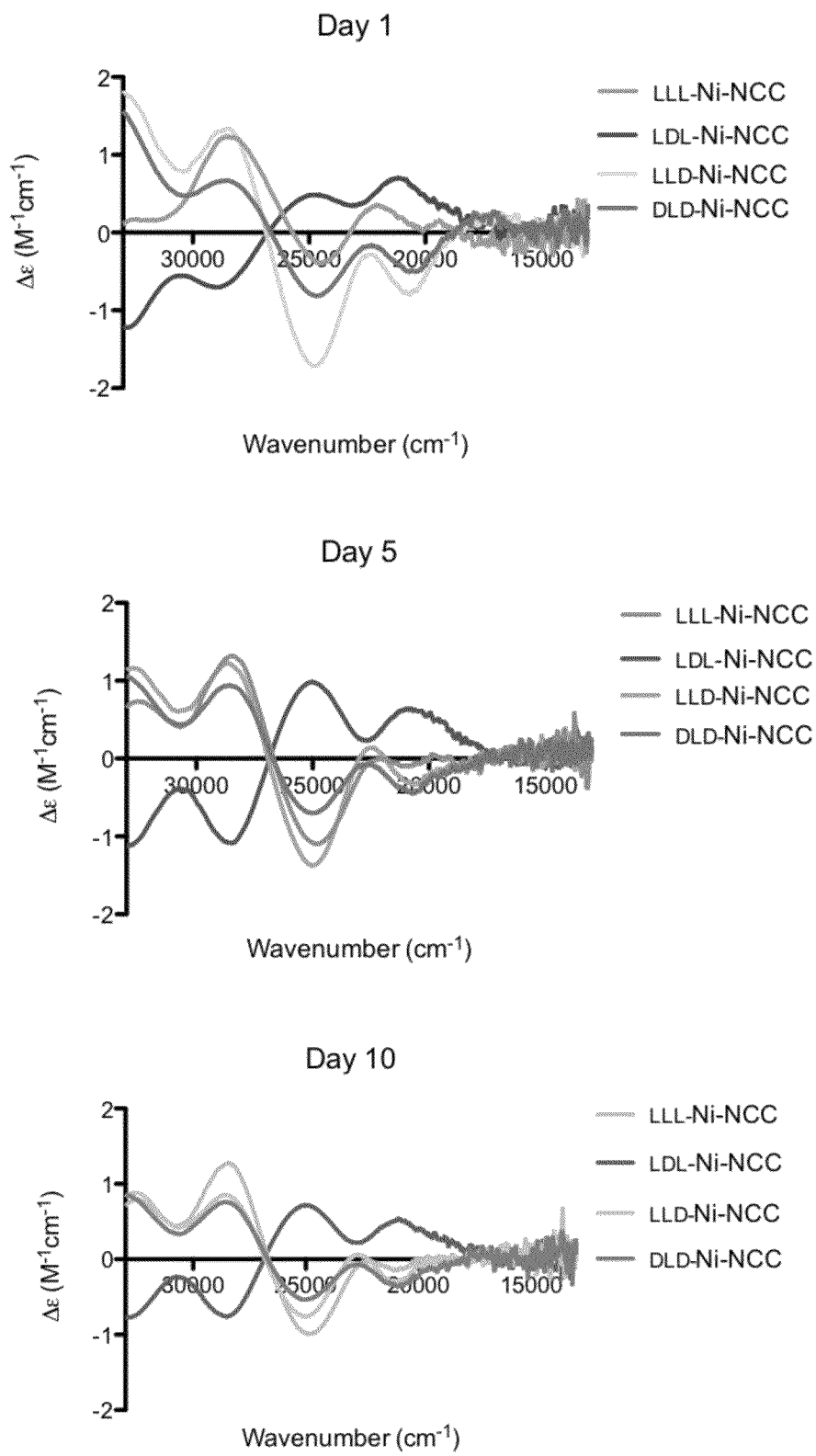
FIG. 19 shows CD spectra depicting the aging progression of various chiral versions of the Ni-NCC complex.

FIG. 18 further illustrates the characterization of Ni-NCC complexes containing D amino acids with aging. The DLD-Ni$^{II}$-NCC spectrum overlaid with the aged Ni-NCC spectrum shows parallel features (FIG. 18). These data indicate chiral inversion occurs at the first and third position within Ni-NCC to generate the DLD-Ni$^{II}$-NCC complex. Whereas the spectral features of DLD-Ni$^{II}$-NCC do not shift or lose intensity with time, the CD spectrum of LLD-Ni$^{II}$-NCC evolves over time to look like that of DLD-Ni$^{II}$-NCC (FIG. 19). In contrast, the CD spectrum of aged LDL-Ni$^{II}$-NCC looks like the mirror image of that of DLD-Ni$^{II}$-NCC.

Figure 20:
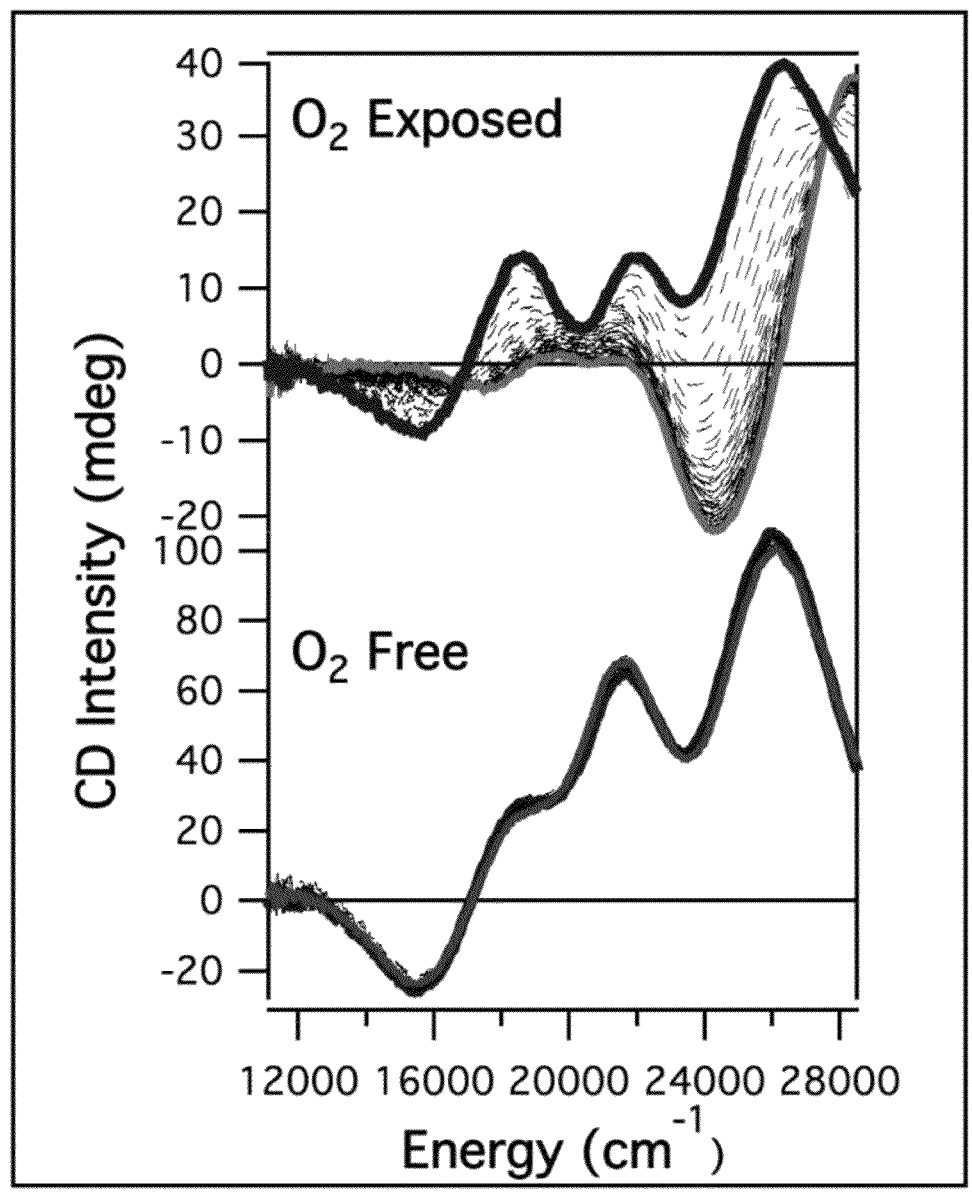
FIG. 20 shows CD spectra of aging Ni-NCC in pH 7.4 potassium phosphate buffer exposed to air (top) and purged with Ar (bottom). Darker spectra were obtained at the time the absorption spectra were at maximum intensity, indicating maximum LLL-Ni-NCC complex formation (t=10 minutes for $O_2$ exposed and t=300 minutes for $O_2$-free), lighter spectra were collected at t=590 minutes, and intermediate spectra obtained every ten minutes between these two times are represented as black dotted lines.

FIG. 20 shows CD spectra of aging Ni-NCC in pH 7.4 potassium phosphate buffer exposed to air (top) and purged with Ar (bottom). Darker spectra were obtained at the time the absorption spectra were at maximum intensity, indicating maximum LLL-Ni-NCC complex formation (t=10 minutes for O$_2$ exposed and t=300 minutes for O$_2$-free), lighter spectra were collected at t=590 minutes, and intermediate spectra obtained every ten minutes between these two times are represented as black dotted lines.

Figure 21:
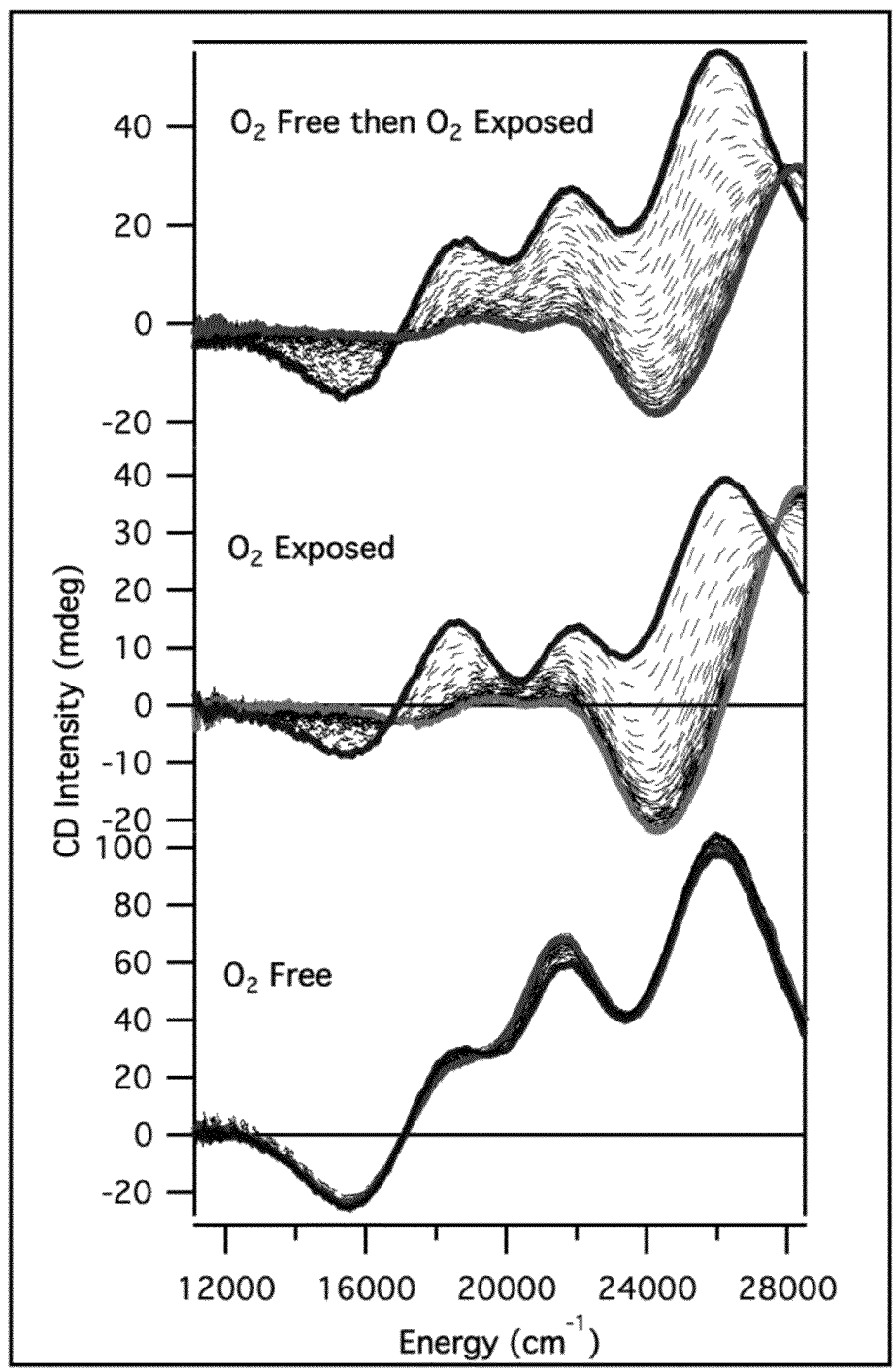
FIG. 21 shows CD spectra of Ni-NCC generated $O_2$-free and incubated 120 minutes to form LLL-Ni-NCC complex, then injected with $O_2$ (top), Ni-NCC generated $O_2$-exposed (middle), and Ni-NCC generated $O_2$-free (bottom). Darker spectra were obtained at t=10 minutes for the $O_2$-exposed sample and t=130 minutes for the sample prepared $O_2$-free and the sample formed $O_2$-free, then injected with $O_2$. The lighter spectra were collected after t=600 minutes for all three samples. Intermediate spectra obtained every ten minutes between these two times are represented as black dotted lines.

FIG. 21 shows CD spectra of Ni-NCC generated O$_2$-free and incubated 120 minutes to form LLL-Ni-NCC complex, then injected with O$_2$ (top), Ni-NCC generated O$_2$-exposed (middle), and Ni-NCC generated O$_2$-free (bottom). Darker spectra were obtained at t=10 minutes for the O$_2$-exposed sample and t=130 minutes for the sample prepared O$_2$-free and the sample formed O$_2$-free, then injected with O$_2$. The lighter spectra were collected after t=600 minutes for all three samples. Intermediate spectra obtained every ten minutes between these two times are represented as black dotted lines.

Figure 22:
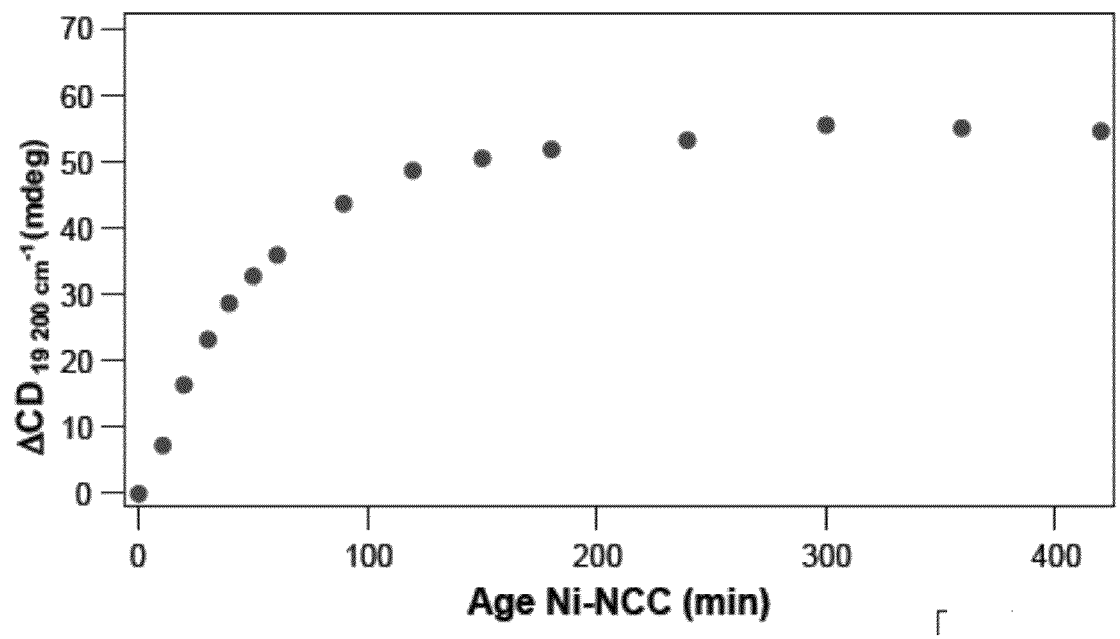
FIG. 22 shows a plot of the change in intensity of the CD signal at 19 200 $cm^{-1}$ as a function of exposure to oxygen in air.

FIG. 22 shows a plot of the change in intensity of the CD signal at 19 200 cm$^{-1}$ as a function of exposure to oxygen in air.

Figure 23:
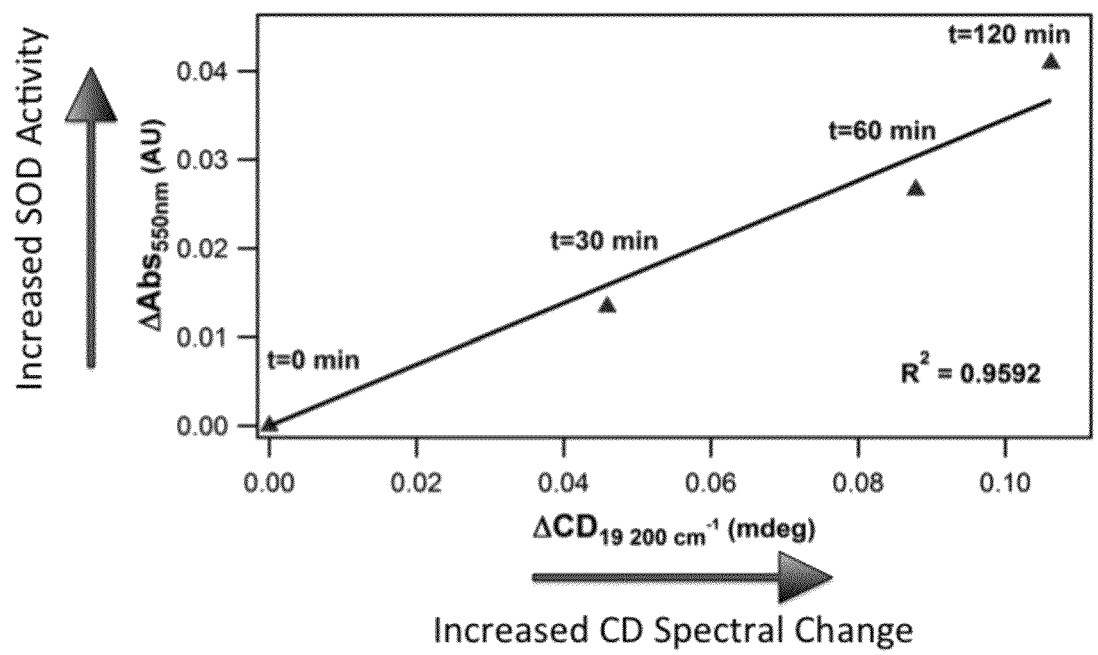
FIG. 23 shows a plot of the change in intensity of the CD signal at 19 200 $cm^{-1}$ verses the amount of SOD (superoxide dismutase) activity as a function of exposure to oxygen in air.

FIG. 23 shows a plot of the change in intensity of the CD signal at 19 200 cm$^{-1}$ verses the amount of SOD (superoxide dismutase) activity as a function of exposure to oxygen in air.

The time-progression of the CD and electronic absorption spectra of LLL-Ni$^{II}$-NCC indicate the accumulation of an intermediate after ~10 hours of incubation with metal. The CD spectrum of this intermediate is identical to that of the 24-hour intermediate described previously, and is nearly featureless below 22 000 cm$^{-1}$. This intermediate is not a singly-inverted species, as the CD spectra collected for authentic DLL- and/or LLD-Ni$^{II}$-NCC are different than the corresponding spectrum of the ten-hour intermediate. Attempts to reproduce the CD spectrum of the ten-hour intermediate via spectral combinations of authentic (i.e., O$_2$-free) LLL-, DLL-, LLD- and DLD-Ni$^{II}$-NCC were unsuccessful. The CD spectra of LLD- and DLD-Ni$^{II}$-NCC both show a positive band at ~17 000 cm$^{-1}$ whereas those of DLL-Ni$^{II}$-NCC and LLL-Ni$^{II}$-NCC have a negative band at ~16 000 cm$^{-1}$. Therefore, the lower-energy features, although varied in sign, are significantly shifted such that they do not cancel each other out to make the spectrum appropriately featureless below 21 000 cm$^{-1}$. This suggests that the ten-hour-aged intermediate is not a mixture of various chiral forms of Ni$^{II}$-NCC. Another possible assignment of the ten-hour aged intermediate is a Ni$^{II}$-form of NCC where Cys3 has dissociated from the Ni$^{II}$ center, in a "Cys3-off" configuration. The CD spectra of authentic (i.e., O$_2$-free) LLD-, and DLD-Ni$^{II}$-NCC both show a positive band at ~17 000 cm$^{-1}$ (FIGS. 7 and 10), whereas the CD spectra of LLL-, and DLL-Ni$^{II}$-NCC show a negative feature near this energy (at ~16 000 cm$^{-1}$; FIG. 4 and FIG. 9). Therefore, the band at 17 000 cm$^{-1}$ is directly related to the chiral state of Cys3. Therefore, removal of a thiolate ligand could account for the lack of significant CD spectral features below 21 000 cm$^{-1}$. Considering the structure of LLL-Ni$^{II}$-NCC, it is expected that the inversion of Cys3 would not occur without dissociation of this cysteinate ligand. Thus, the CD spectrum of the ten-hour aged species has contributions from a species where Cys3 has dissociated from the Ni$^{II}$ center. This "Cys3-off" form of Ni$^{II}$-NCC could also offer a potential route to the secondary reactions of the complex. For the related enzyme Ni-SOD, removal of one Cys ligand by site-directed mutagenesis led to the lack of any sulfur incorporation and the formation of a high-spin (S=1) Ni$^{II}$ protein. $^1$H-NMR experiments on Ni$^{II}$-NCC have been hampered by the presence of a minor paramagnetic component, which, on the basis of low-temperature, variable-temperature, variable-field magnetic circular dichroism (VTVH MCD) data was assigned to a high-spin Ni$^{II}$ component that represented less than 1% of the sample under the conditions of the VTVH MCD experiment.

Controlled Reactivity in Ni$^{II}$-NCC.

The data underscore the specific and unique reactivity of the Ni$^{II}$-NCC complexes in the absence of O$_2$, as well as their chemistry when O$_2$ is available to react with the Ni$^{II}$ center. Oxidation to the Ni$^{III}$ form initiates a cascade of reactions that convert the bulk of the sample to DLD-Ni$^{II}$-NCC and some secondary products. The preferred coordination geometry of a low-spin, thiolate-bound Ni$^{II}$ center is different than that of a Ni$^{III}$ ion (square planar versus distorted octahedral geometry). Thus, the Ni$^{III}$ forms of nickel-peptide complexes can be stabilized in a different fashion than the Ni$^{II}$ centers to prevent undesired secondary or peptide-modifying reactions.

In Ni-SOD, metal oxidation is coupled to a change in the coordination environment around the metal center. Specifically the square planar N2:S2 geometry of Ni$^{II}$-SOD converts to square pyramidal N3:S2 geometry in Ni$^{III}$-SOD through the axial ligation of a histidine. Without wishing to be bound by theory, histidine coordination can serve several functions, including tuning the reduction potential of the Ni center. Axial histidine ligation to the Ni$^{III}$ center can also serve to prevent any side-reactions for Ni$^{III}$-SOD.

Example 3

Generation of Metal-Peptide Complexes.

The peptides GGNCC (SEQ ID NO. 1), GGGCC (SEQ ID NO. 3), GNNCC (SEQ ID NO. 4), and GNGCC (SEQ ID NO. 5), as well as GGNCC (SEQ ID NO. 1) with D-cysteine in the fifth position (XXLLD-GGNCC) (SEQ ID NO. 8), GGNCC (SEQ ID NO. 1) with D-asparagine in the third position and D-cysteine in the fifth position (XXDLD-GGNCC) (SEQ ID NO. 9), and GGNCC (SEQ ID NO. 1) with D-cysteine in the fourth position (XXLDL-GGNCC) (SEQ ID NO. 10), and GGNCC (SEQ ID NO. 1) with D-asparagine in the third position and D-cysteine in the fourth position (XXDDL-GGNCC) (SEQ ID NO. 11), were purchased from Genscript Corporation. (Piscataway, N.J., USA). The longer sequences GGGCCGGK (SEQ ID NO. 6) and GGNCCGGK (SEQ ID NO. 2), where the NCC sequence is in the middle of the peptide sequence rather than at the C-terminus, were also purchased. Nickel-polypeptide complexes were generated in 50 mM potassium phosphate at pH 7.4 either by adding one equivalent of NiSO$_4$ or by incubation with nickel-charged immobilized metal affinity chromatography resin, as previously described.

Expression and Purification of Ni-PRL-1.

PRL was expressed and purified as described previously. Briefly, the gene for PRL-1 encoded in a pET-30 Xa/LIC expression vector was transformed into BL21(DE3) *E. coli* cells and grown at 37° C. in minimal media supplemented with trace metals in an orbital shaker at 250 rpm. Expression was induced with 1 mM IPTG at an OD600 of 0.6 to 0.8 and harvested by centrifugation after 3 hours. Cells were lysed with a French pressure cell and centrifuged for 1 hour at 21,000×g. The soluble protein was purified using Ni-IMAC chromatography, during which metal was incorporated into the NCC tripeptide sequence. Protein was eluted with imidazole, the His tag was cleaved with Factor Xa, and a size exclusion chromatography step was performed to obtain the pure nickel-bound protein. Protein concentration was determined from the absorbance at 280 nm ($\epsilon_{280}$=19,420 L mol$^{-1}$ cm$^{-1}$).

CD and Absorption Studies.

Ni-peptide samples were placed in a cuvette with a 1-cm path length and scanned from 800-300 nm using both absorption and CD spectroscopy. Samples were scanned immediately after generation and then subsequently monitored at various time points. Background scans of buffer alone were subtracted from each scan. Spectra for Ni-PRL-1 were also collected immediately after purification. Absorption studies were performed on an Agilent 8453 UV/Visible spectrophotometer. Circular dichroism analysis was performed on a J-815 (Jasco Corporation) spectropolarimeter.

Deconvolution of CD and Absorption Data.

Deconvolution of CD and absorption data was performed using Igor Pro (Wavemetrics). Iterative Gaussian deconvolutions were performed with a constant peak width of 1600 cm$^{-1}$. Absorption band energies were kept within 10% of the corresponding CD bands due to the broad nature of the absorption spectrum.

ESI-MS.

Samples of Ni-GGGCC (SEQ ID NO. 3), Ni-GGNCC (SEQ ID NO. 1), Ni-GNNCC (SEQ ID NO. 4), and Ni-GNGCC (SEQ ID NO. 5) were diluted 100× in a 1:1 mixture of methanol/water and analyzed on an LCT Premier (Waters Corporation) operating in negative ion mode, as described previously.

MCD.

Samples containing 3 mM Ni-GGNCC (SEQ ID NO. 1) were prepared in 50 mM phosphate at pH 7.4. An equal volume of glycerol was added, yielding a 50% glycerol solution containing 1.5 mM Ni-GGNCC (SEQ ID NO. 1). The sample was placed in an MCD cell and flash frozen. Spectra were collected on a J-815 (Jasco Corporation) interfaced with an Oxford Spectromag 4000 at +7 and −7 Tesla, and the difference was found via subtraction in order to remove any CD signal. Spectra were collected at 20, 8, and 4.5 K, and analyzed to identify any changes in the spectra that indicate paramagnetic character. The feasibility of correlating these low temperature data with the structure of Ni-GGNCC (SEQ ID NO. 1) at room temperature is demonstrated by the lack of apparent changes in the corresponding CD spectra collected at 298 and 4.5 K.

Preparation of Nickel-Released Samples for Nuclear Magnetic Resonance (NMR).

Ni-GGNCC (SEQ ID NO. 1) was generated via spiking 3 mM GGNCC (SEQ ID NO. 1) in 50 mM potassium phosphate at pH 7.4 with NiSO$_4$. The pH was dropped to approximately 5.0 by the addition of 1M HCl to release the metal. The sample was purified using reverse-phase HPLC on a Luna 5µ C18(2) column (Phenomenex) to remove the released nickel and to isolate the apo, nickel-exposed peptide sample (nickel-exposed GGNCC (SEQ ID NO. 1)). Fractions containing nickel-exposed GGNCC (SEQ ID NO. 1) were pooled and lyophilized.

Nuclear Magnetic Resonance (NMR).

Peptide samples (xxLLD-GGNCC; SEQ ID NO. 8), (xxDLD-GGNCC; SEQ ID NO. 9), (xxLDL-GGNCC; SEQ ID NO. 10), (xxDDL-GGNCC; SEQ ID NO. 11), and (xxLLL-GGNCC; SEQ ID NO. 1), as well as nickel-exposed GGNCC (SEQ ID NO. 1) were dissolved at a concentration of 3 mM in 50 mM potassium phosphate, pH 7.4, containing 10% D$_2$O. $^1$H spectra were acquired using a 500 MHz Bruker DRX spectrometer equipped with a triple resonance probe. Water suppression was accomplished using presaturation.

Ni-SOD Xanthine/Xanthine Oxidase Coupled Assay.

Superoxide scavenging activity was determined as reported previously, except Ni-peptides were generated in situ using one equivalent of NiSO$_4$. Superoxide scavenging activity of Ni-GGGCC (SEQ ID NO. 3), Ni-GGNCC (SEQ ID NO. 1), Ni-GNNCC (SEQ ID NO. 4), and Ni-GNGCC (SEQ ID NO. 5) was determined using the standard xanthine/xanthine oxidase method developed by Crapo and coworkers. All reagents were generated in 50 mM potassium phosphate, 100 µM EDTA reaction buffer at pH 7.8 except for the Ni-peptide complexes, which were generated in 50 mM potassium phosphate, pH 7.4. In this assay, 600 µM cytochrome c from bovine heart (Sigma), 300 µM xanthine (Sigma) and enough xanthine oxidase from buttermilk (Sigma) to cause a change in absorbance at 550 nm of 0.02-0.04 AU per minute were added to a final volume of 300 µL with reaction buffer. The change in absorbance at 550 nm was monitored on a Cary 100 UV-Visible spectrophotometer (Varian).

Electrochemistry.

Electrochemical data were collected as previously described. 3-mL samples of 3 mM Ni-GGNCC (SEQ ID NO. 1) and Ni-GGGCC (SEQ ID NO. 3) were prepared in 50 mM potassium phosphate at pH 7.4. After incorporation, pH was raised to 10 to observe more intense signal. Cyclic voltammetry (CV) data were collected with a CH1812C Electrochemical Analyzer potentiostat (CH Instruments) with a three-electrode setup (platinum working electrode, Bioanalytical Systems, Inc.; Pt auxiliary electrode; Ag/AgCl reference electrode) in a glass CV cell. Potential was applied from zero to 1.2 V with a scan rate of 0.2 V per second, and current was measured.

Coordination of Cyanide and IR Analysis.

Samples of Ni-GGGCC (SEQ ID NO. 3) and Ni-GGNCC (SEQ ID NO. 1) were prepared at a concentration of 3 mM in 50 mM potassium phosphate at pH 7.4. One equivalent of potassium cyanide was added to each of the samples. Samples were flash frozen and lyophilized. IR analysis was performed to observe the cyanide peak in each sample. IR spectra were acquired from dry powder samples on a Perkin Elmer Spectrum 100 FT-IR spectrometer equipped with a universal ATR (Attenuated Total Reflection) sampling accessory. The spectrum of solid potassium cyanide was used to compare the shift of i(C≡N) vibration from the free to the nickel-coordinated state.

Preparation and Spectroscopic Characterization of Ni-Peptides and Ni-PRL-1.

The NCC tripeptide sequence was incorporated into a series of four pentapeptides (GGNCC (SEQ ID NO. 1), GGGCC (SEQ ID NO. 3), GNNCC (SEQ ID NO. 4), and GNGCC (SEQ ID NO. 5)), two 8 mers (GGGCCGGK (SEQ ID NO. 6) and GGNCCGGK (SEQ ID NO. 2)), and within full-length PRL-1. Metal incorporation in the appropriate geometry occurs via metal transfer from a weaker chelating moiety. While immobilized metal affinity chromatography resin has been a choice for obtaining pure compounds for examination following the metallation reaction, for studies requiring immediate spectroscopic analysis, a solution transfer is preferred. Although $NiCl_2$ fails to generate the desired complex, $NiSO_4$ enables metal incorporation and provides the same spectral features without the need for a solid support. The peptides were analyzed with CD spectroscopy to validate the ligands involved in the metal coordination.

Figure 24:
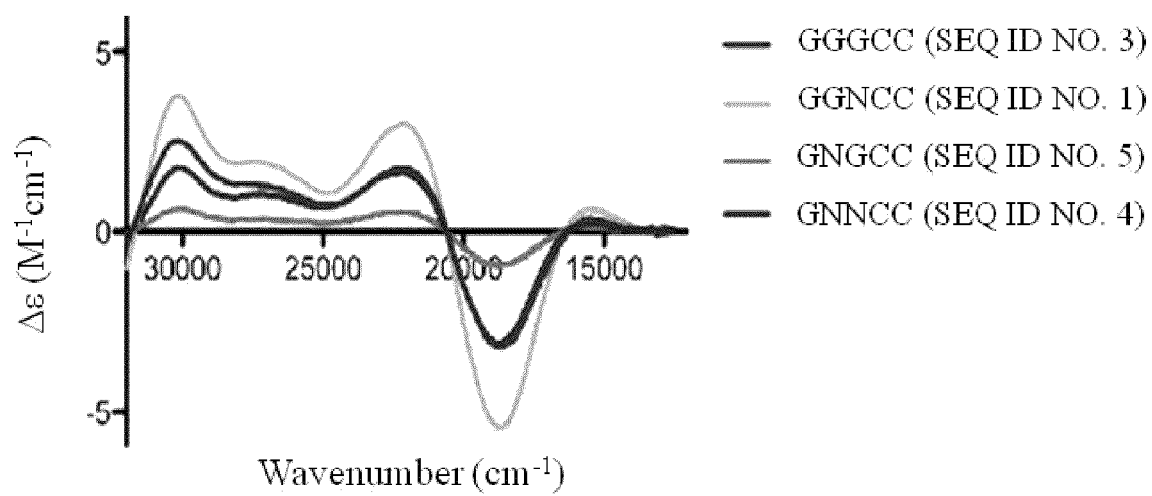
FIG. 24 shows the CD spectra of Ni-pentapeptides in 50 mM potassium phosphate at pH 7.4. The spectral features are similar with different peptides, while intensity differences are present.
Figure 25:
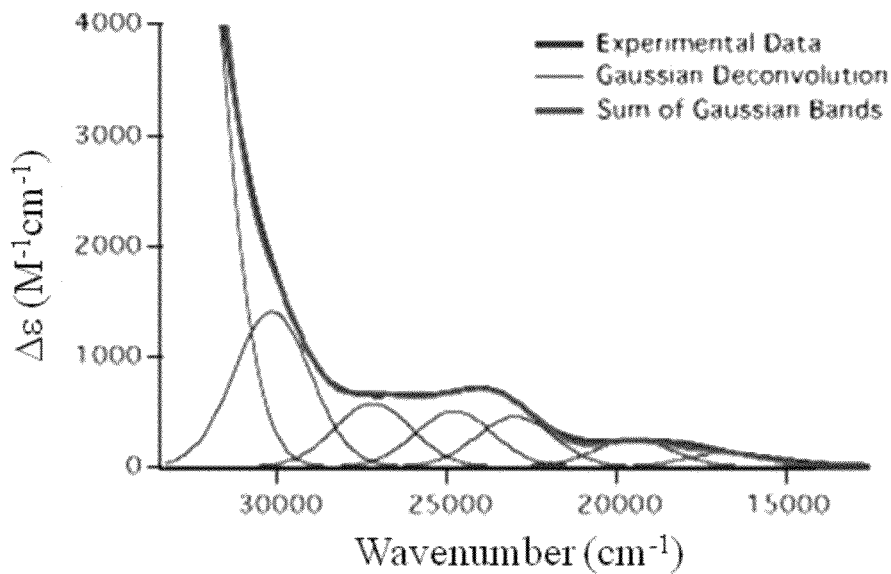
FIG. 25 panel A shows Gaussian deconvoluted absorption spectra of Ni-GGNCC (SEQ ID NO. 1). Panel B shows CD spectra of Ni-GGNCC (SEQ ID NO. 1).
Figure 25:
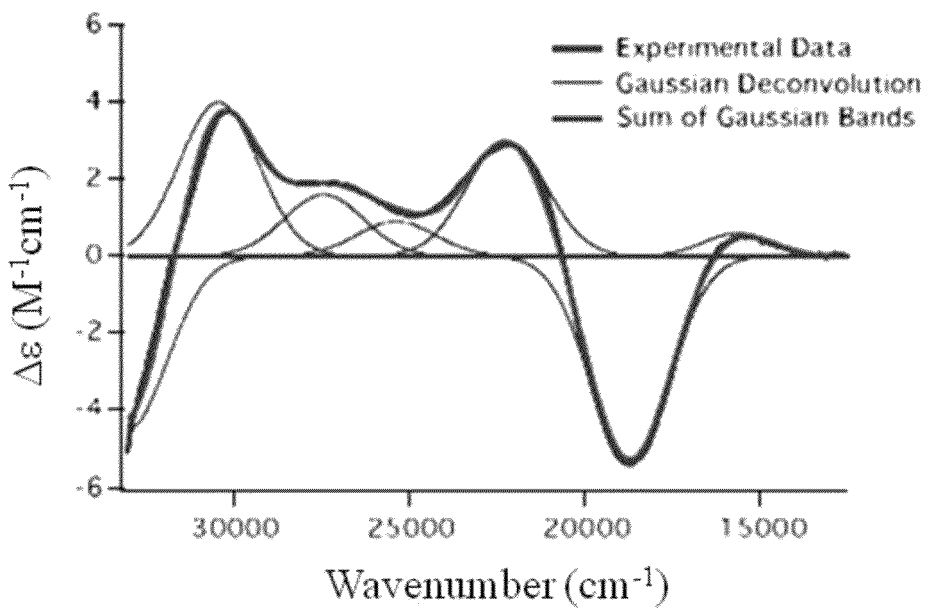

The spectral features were slightly different than those previously reported for the Ni-NCC tripeptide, which is expected because the amine nitrogen ligand from the N-terminus in the tripeptide is replaced by an amide nitrogen ligand in the longer peptides. The four pentapeptides have identical spectral profiles, with only differences in intensity (FIG. 24). Absorbance and CD spectra were deconvoluted (FIG. 24, and Table 4). MS data confirm the Ni complex of each pentapeptide is at the expected mass (e.g. Ni-GGNCC (SEQ ID NO. 1), m/z=506.22, calculated=506.02). See FIG. 24. for CD spectra of Ni-pentapeptides in 50 mM potassium phosphate pH 7.4. Spectral features are the same with different peptides, though intensity differences are present. See FIG. 25 for Gaussian deconvoluted absorption (top) and CD (bottom) spectra of Ni-GGNCC (SEQ ID NO. 1).

TABLE 4

Table 4. Energies of spectral bands in Ni-GGNCC (SEQ ID NO. 1).

Ni-GGNCC (SEQ ID NO. 1)

| CD | | Absorption | |
|---|---|---|---|
| Energy (cm$^{-1}$) | Δε (M$^{-1}$cm$^{-1}$) | Energy (cm$^{-1}$) | ε (M$^{-1}$cm$^{-1}$) |
| 15 600 | 0.6 | 16 800 | 120 |
| 18 700 | −5.3 | 19 500 | 240 |
| 22 200 | 3.0 | 23 000 | 450 |
| 25 200 | 0.9 | 24 980 | 530 |
| 27 410 | 1.8 | 27 400 | 580 |
| 30 400 | 4.0 | 30 300 | 1300 |
| 33 000 | −4.5 | 32 900 | 6900 |

Figure 26:
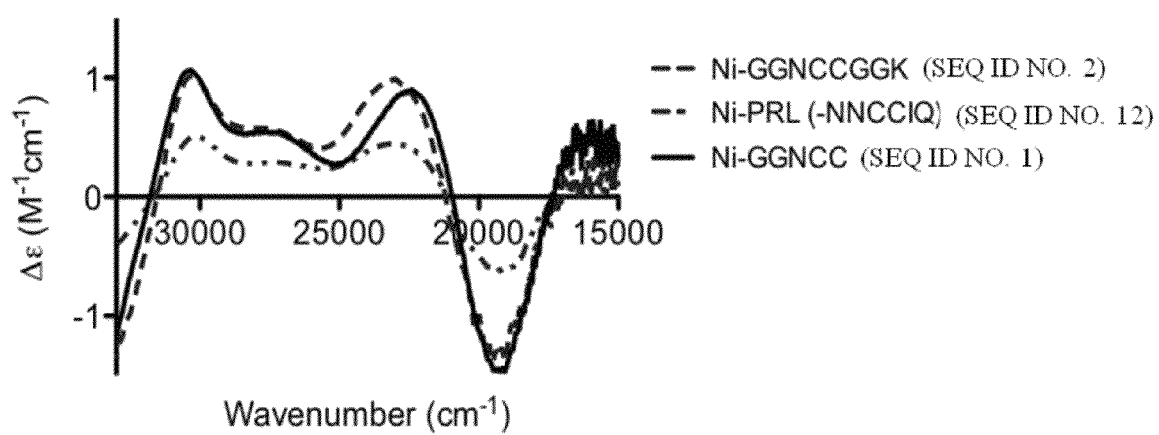
FIG. 26 shows CD spectra of NCC in longer sequences, including GGNCC (SEQ ID NO. 1), GGNCCGGK (SEQ ID NO. 2), and PRL-1, which each contain the NCC sequence. All samples were scanned 24 hours after metal incorporation to match the time frame under which PRL-1 data were collected.

The tripeptide sequences NCC or GCC were also placed in the middle of an 8 mer peptide, generating GGNCCGGK (SEQ ID NO. 2) and GGGCCGGK (SEQ ID NO. 6), respectively. The spectral features of the octomers are similar to that of the pentapeptides, showing that embedding NCC in a longer sequence does not further change the coordination, indicating the metal is bound in the same cis 2N:2S square planar arrangement as observed with NCC (FIG. 26). Differences in intensity are observed, likely due to differences in efficiency of metal incorporation. ESI-MS operating in negative ion mode confirms 1:1 stoichiometry of peptide to metal, and no thiol oxidation or change in the peptide:metal ratio were observed in samples analyzed 24 hours after generation. The peptide GGNCHGGK (SEQ ID NO. 7) was also used to show that the absence of one of the cysteine ligands results in different coordination. MS data indicate the metal did not insert into the modified sequence, suggesting the incorporation mechanism depends on the presence of the second Cys. Taken together, these data further indicate that the coordination is the same here as in the nickel tripeptide complex (FIG. 1). See FIG. 26: CD spectra of GGNCC (SEQ ID NO. 1), GGNCCGGK (SEQ ID NO. 2), and PRL-1 (SEQ ID NO. 12), which contain the NCC sequence. All samples were scanned 24 hours after metal incorporation to match the time frame under which PRL-1 data were collected.

In the case of the Ni-NCC tripeptide complex, the nickel ion is primarily $Ni^{II}$, however, it was considered that change from amine/amide coordination that is present in the tripeptide to the bis-amide coordination that is present in the pentapeptide can stabilize a $Ni^{III}$ state and cause more of a $Ni^{II/III}$ mixture to be present. To test for the presence of $Ni^{III}$, MCD data was collected on the Ni-GGNCC (SEQ ID NO. 1) sample. MCD data show no temperature dependence of the spectra at field, which indicates no paramagnetic component is present and suggests $Ni^{III}$ does not accumulate.

Circular Dichroism Analysis of Ni-Pentapeptide Complexes Containing D Amino Acids.

Figure 27:
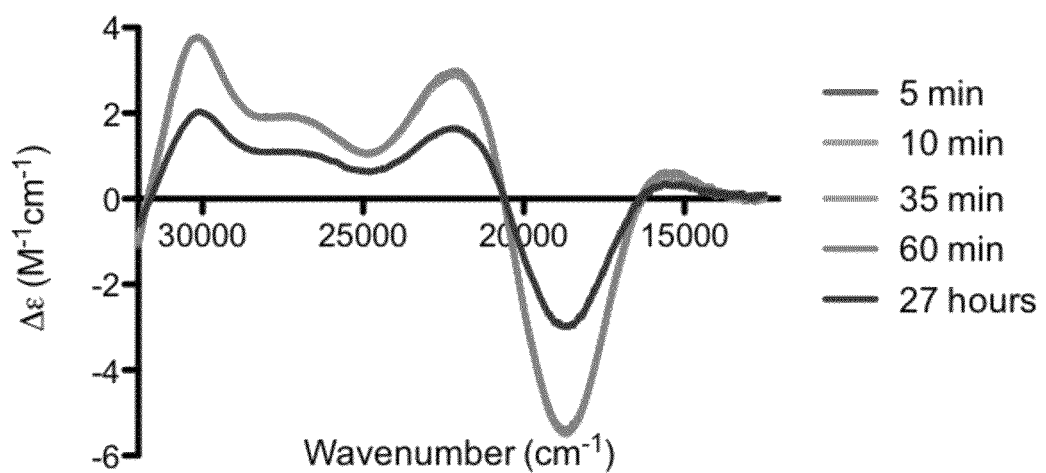
FIG. 27 shows minimal changes of aging for the spectral features of Ni-GGNCC (SEQ ID NO. 1) within a given buffer system of 50 mM potassium phosphate at pH 7.4.

In the NCC tripeptide, chiral inversion occurs at the first and third positions, where nickel incorporated into LLL-NCC converts it to the DLD-NCC isoform over the course of hours. The inversion of the asparagine Cα reorients its side chain away from the space above the plane, allowing coordination of a fifth ligand or substrate and thereby promoting activity. This chiral inversion is apparent in the CD spectra, as the signs of the DLD-NCC peaks are opposite of those of the LLL-NCC. With the pentapeptide complex, however, following the insertion reaction, changes in sign are not observed in the CD spectra, but only a small decrease in intensity occurs on this timescale (FIG. 27). As such, the lack of sign change suggests chiral inversion either does not occur or is concomitant with metal incorporation; additional studies were performed to examine the possibility of rapid chiral inversion in the pentapeptide system. See FIG. 27: Aging does not change the spectral features of Ni-GGNCC (SEQ ID NO. 1) within a given buffer system. (50 mM potassium phosphate pH 7.4)

Figure 28:
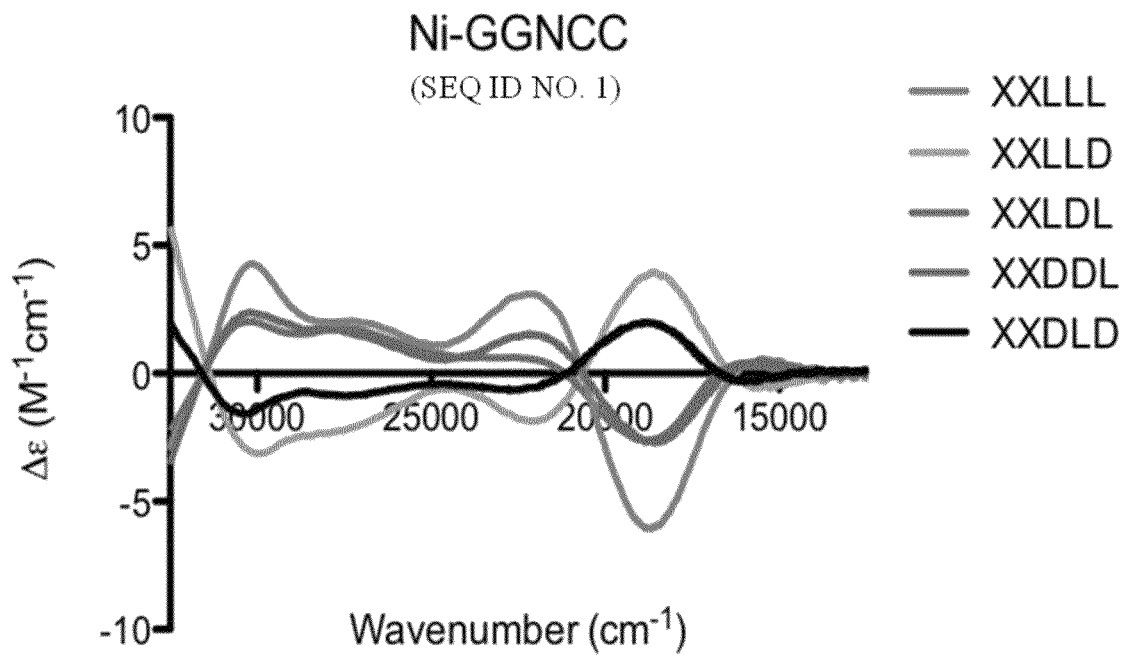
FIG. 28 panel A shows CD profiles of several chiral forms of GGNCC (SEQ ID NO. 1) in phosphate buffer. Panel B shows CD profiles of several chiral forms of GGNCC (SEQ ID NO. 1) in phosphate buffer, normalized at 22,000 $cm^{-1}$.
Figure 28:
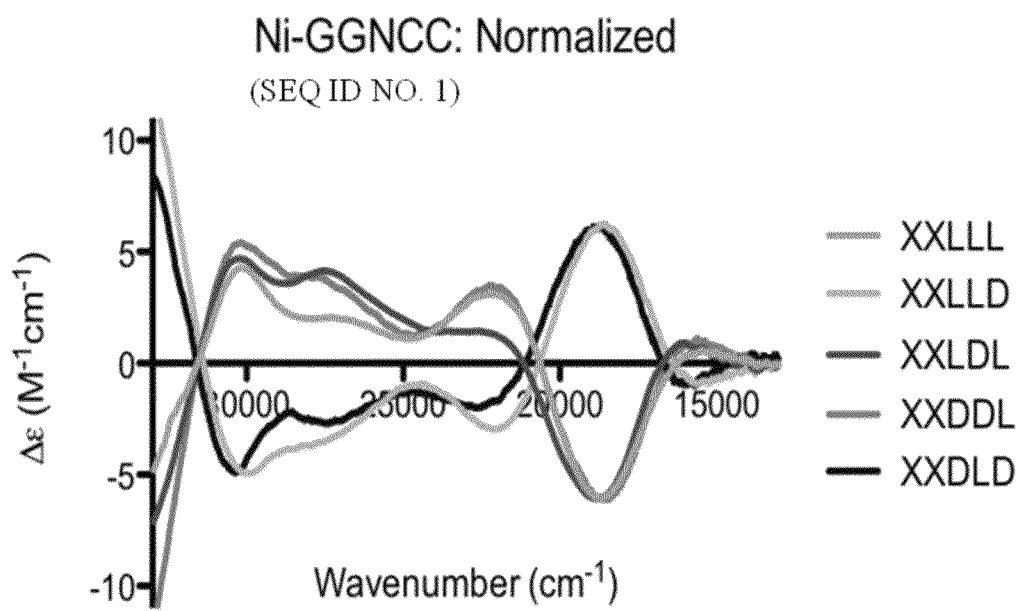

In order to further explore the possibility of chiral inversion in the pentapeptide and identify any affected position(s), the pentapeptides xxLLD-GGNCC (SEQ ID NO. 8), xxDLD-GGNCC (SEQ ID NO. 9), xxLDL-GGNCC (SEQ ID NO. 10), xxDDL-GGNCC (SEQ ID NO. 11), and xxLLL-GGNCC (SEQ ID NO. 1), were metallated and compared to the all-L form. CD spectra of the D-containing sequences were collected and compared to data from the all-L isoform (FIG. 28, panel A). The data were normalized at 22,000 cm$^{-1}$ to compare relative intensity differences that result from different chiral species (FIG. 28, panel B). The spectra of the D-amino acid-containing peptides are all different from that observed for the all-L form of GGNCC (SEQ ID NO. 1), suggesting chiral inversion likely does not occur in the pentapeptide complex. Specifically, the xxDLD-GGNCC (SEQ ID NO. 9) and xxLLL-GGNCC (SEQ ID NO. 1) nickel complexes have spectra that are nearly mirror images of one another; since DLD-NCC is the final form of the tripeptide complex, this indicates the bisamide pentapeptide complex and the mixed amine/amide tripeptide complex behave differently with respect to chiral inversion chemistry. See FIG. 28, panel A. CD profiles of several chiral forms of GGNCC (SEQ ID NO. 1) in phosphate buffer. FIG. 28, panel B. CD profiles of several chiral forms of GGNCC (SEQ ID NO. 1) in phosphate buffer, but normalized at 22,000 cm$^{-1}$.

Nuclear Magnetic Resonance of Chiral Forms of the Pentapeptides.

Figure 29:
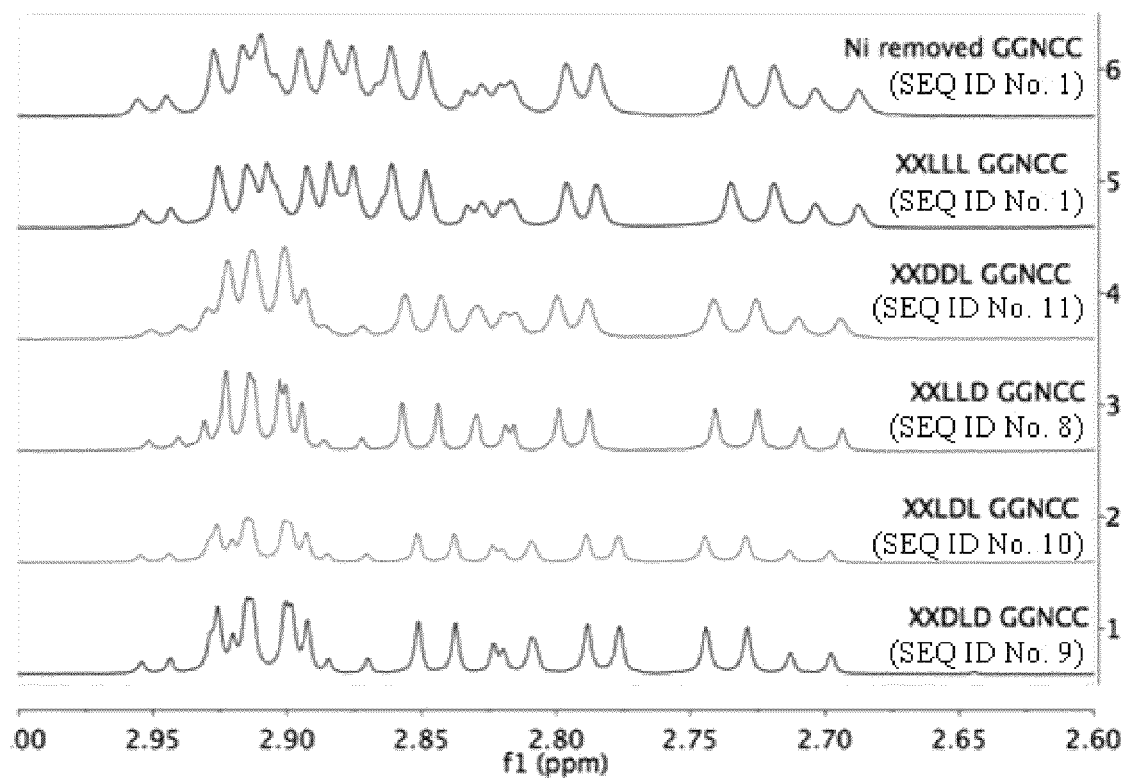
FIG. 29 shows NMR spectra of Ni-exposed GGNCC (SEQ ID NO. 1) compared to each D-containing form. Differences in splitting patterns between 2.6 and 3.0 ppm correspond to the different chiralities of the respective pentapeptides.
Figure 30:
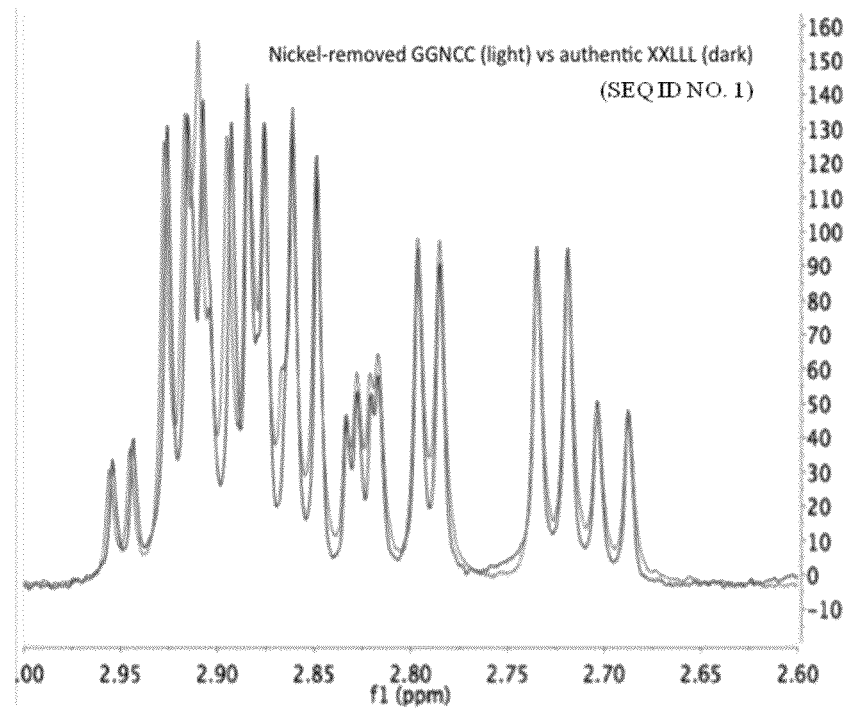
FIG. 30 panel A shows superimposed NMR spectra of GGNCC (SEQ ID NO. 1) and nickel-exposed GGNCC (SEQ ID NO. 1). Panel B shows stacked NMR spectra of GGNCC (SEQ ID NO. 1) and nickel-exposed GGNCC (SEQ ID NO. 1). Peaks correspond to the $^1H$ on the $CH_2$ on the Asn and Cys side chains.
Figure 30:
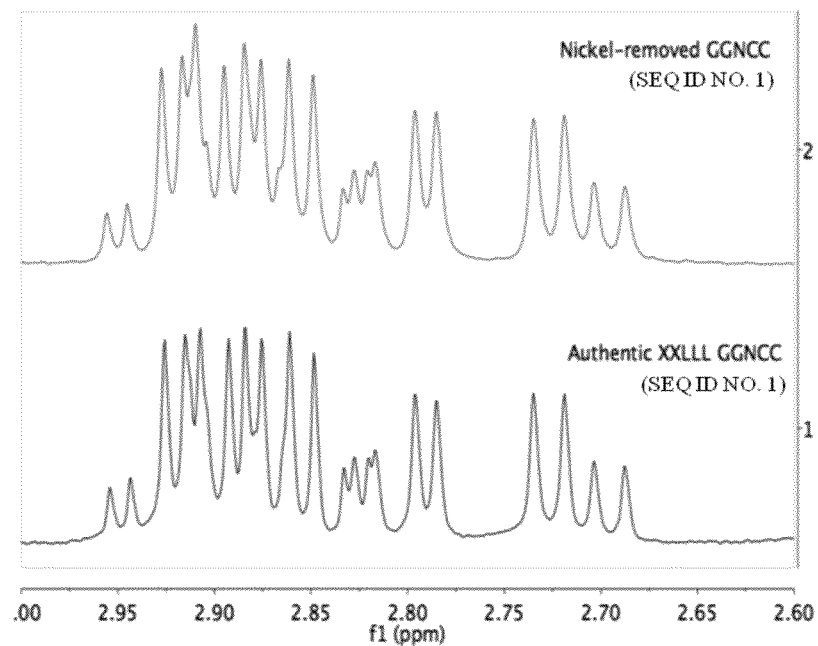

To further validate the absence of chiral inversion in the Ni-pentapeptide system, NMR data were collected for a set of control peptides. NMR spectra were acquired for the apo forms of the xxLLD-GGNCC (SEQ ID NO. 8), xxDLD-GGNCC (SEQ ID NO. 9), xxLDL-GGNCC (SEQ ID NO. 10), xxDDL-GGNCC (SEQ ID NO. 11), and xxLLL-GGNCC (SEQ ID NO. 1) systems to assess difference in splitting patterns for species containing D-amino acids. To determine which form the nickel-exposed GGNCC (SEQ ID NO. 1) resembles, a sample of GGNCC (SEQ ID NO. 1) was metallated, the pH was dropped to release the metal, and the peptide was separated from free nickel using reverse phase HPLC. After purification and isolation of the nickel-exposed GGNCC (SEQ ID NO. 1), NMR was employed, and the spectrum of the nickel-exposed GGNCC (SEQ ID NO. 1) was compared to that of each GGNCC (SEQ ID NO. 1) form. The spectra of the peptides are very similar, with modest differences between 2.65 and 3.0 ppm (FIG. 29). These peaks correspond to the $CH_2$ groups on the Asn and Cys side chains, and their splitting patterns experience differences based on how they are oriented in space and how they communicate with the nearby protons, which varies with the D or L configuration of each amino acid residue. The xxDLD-GGNCC (SEQ ID NO. 9) and xxLDL-GGNCC (SEQ ID NO. 10) are similar to one another, and the xxLLD-GGNCC (SEQ ID NO. 8) and xxDDL-GGNCC (SEQ ID NO. 11) are similar to one another, based on the exact opposite chiralities of these peptides. xxLLL-GGNCC (SEQ ID NO. 1) and nickel-exposed GGNCC (SEQ ID NO. 1) exhibit nearly identical NMR spectra (FIG. 30) suggesting nickel-exposed GGNCC (SEQ ID NO. 1) maintains its xxLLL-GGNCC (SEQ ID NO. 1) configuration and chiral inversion does not occur in the pentapeptide. FIG. 29: NMR spectra of Ni-exposed GGNCC (SEQ ID NO. 1) compared to each D-containing form. Differences in splitting patterns between 2.6 and 3.0 ppm correspond to the different chiralities of the different pentapeptides. FIG. 30: Superimposed (A) and stacked (B) NMR spectra of xxLLL-GGNCC (SEQ ID NO. 1) and nickel-exposed GGNCC (SEQ ID NO. 1). Peaks correspond to the $^1$H on the $CH_2$ on the Asn and Cys side chains.

Reactivity of Pentapeptides: Superoxide Scavenging, Coordination of Fifth Ligand, and Electrochemistry.

In the NCC tripeptide, chiral inversion occurs at the first and third positions, such that nickel incorporation into LLL-NCC converts it to the DLD-NCC isoform over the course of hours. The inversion of the asparagine C-α reorients its side chain away from the space above the plane, allowing coordination of a fifth ligand or substrate and thereby promoting activity. Therefore, with the NCC tripeptide, measures of chiral inversion include the ability of the complex to coordinate a fifth ligand, to have a measurable midpoint potential, and exhibit superoxide scavenging activity. The Ni pentapeptide complexes do not undergo chiral inversion, presumably due to the bis-amide coordination rather than mixed amine/amide coordination found in the tripeptide systems. The xanthine/xanthine oxidase assay was performed, coordination of $CN^-$ was monitored with CD and IR, and electrochemical studies were performed using CV.

The aged NCC tripeptide, which corresponds to the activity of the chirally inverted form, has superoxide scavenging activity (IC50=$4.1 \times 10^{-5}$ M). Despite having bis-amide 2N:2S coordination, as opposed to the mixed amine/amide 2N:2S coordination of the tripeptide system, the longer Ni-peptide complexes have similar superoxide scavenging activity, on the same order of magnitude as the Ni-NCC tripeptide complex (IC50=$9.1 \pm 5 \times 10^{-6}$ M for Ni-GGNCC (SEQ ID NO. 1)).

Cyclic voltammetry was used to measure the midpoint potential of the pentapeptides. The GGGCC (SEQ ID NO. 3) and GGNCC (SEQ ID NO. 1) peptides have similar potentials (respectively, 0.78 and 0.80 mV vs Ag/AgCl at pH 10). These values are slightly higher than those reported for the chirally inverted Ni-NCC tripeptide complex (0.71 mV vs Ag/AgCl). Despite not undergoing chiral inversion, the Ni-pentapeptide signal can be measured immediately after generation, whereas the tripeptide does not have a measurable potential until it has aged and therefore chirally inverted. The small difference in redox potential for the different systems is likely due to a minor deviation in bond length or planarity, but the relatively close potentials are because the overall charge of the complex does not change.

In the Ni-NCC complex, inversion of the asparagine Cα can reorient its side chain away from the space above the plane, allowing coordination of a fifth ligand. To determine if $CN^-$ has access to bind the metal, the pentapeptide complexes Ni-GGNCC (SEQ ID NO. 1) and Ni-GGGCC (SEQ ID NO. 3) were generated, and solid phase IR data were collected on free cyanide and cyanide in the presence of the Ni-pentapeptide complexes. The vibration of $CN^-$ is shifted and corresponds to Ni-bound $CN^-$ (Table 5), as was observed previously with the tripeptide complex, suggesting that $CN^-$ is able to coordinate to the nickel-pentapeptide complex immediately after metal insertion. These data suggest access to the axial position is available and structural rearrangement is not necessary for access to the axial position.

TABLE 5

Table 5. Coordination of $CN^-$ to different nickel species, showing that $CN^-$ coordinates to the pentapeptide immediately after generation, whereas with the tripeptide, chiral inversion must occur before a fifth ligand can bind. NCC and GGNCC (SEQ ID NO. 1) samples were examined in potassium phosphate buffer at pH 7.4.

| Species | $\nu(C \equiv N)$ (cm$^{-1}$) |
|---|---|
| KCN | 2076 |
| K2[Ni(CN)4][18] | 2123 |
| Ni(CN)-(mSOD)[18] | 2108 |
| Ni-NCC + CN- (fresh)[2] | N/A |
| Ni-NCC + $CN^-$ (aged-chirally inverted)[2] | 2107 |
| Ni-GGNCC (SEQ ID NO. 1) + CN- | 2113 |

The peptide sequence NCC is capable of coordinating nickel in a 2N:2S geometry, where the sulfur ligands come from the cysteine side chains, one amino nitrogen ligand is from the N-terminus, and one amido nitrogen ligand is from the peptide backbone. After metal is incorporated with the peptide composed of all-L amino acids, LLL-NCC is converted nearly completely to DLD-NCC within hours. After this site-specific chiral inversion, the Ni-tripeptide complex is a functional mimic of the enzyme nickel superoxide dismutase. This chiral inversion is critical for the superoxide scavenging activity, as conversion from the LLL to DLD correlates directly with activity.

The tripeptide sequence can be incorporated into a longer sequence without disrupting metal complex formation. Here, the coordination of nickel by the NCC sequence within a series of polypeptides was examined. ESI-MS confirms monomeric incorporation of nickel into each pentapeptide, and MCD studies reveal that the nickel is diamagnetic nickel (II), as is the case in the tripeptide. The CD spectral features differ from those of the tripeptide, and the transitions in the pentapeptide complex are shifted to higher energy because the amine nitrogen ligand from the N-terminus in the tripeptide is replaced by an amide in the pentapeptides. These data together indicate that the ligating moieties are analogous; the same two cysteinyl sulfur and backbone nitrogen ligands are utilized, but the extension at the N-terminus changes the nitrogen coordination from mixed amine/amide to bis-amide. The similarity of four pentapeptides, with and without asparagine present in position 3, confirms that the asparagine side chain is not directly involved in metal coordination and nitrogen ligation is due solely to the backbone amides. In the tripeptide the rate of chiral inversion can be monitored because a change in spectral features is clearly observed over time, but no observable changes occur within the pentapeptide. This lack of change implies that chiral inversion either does not occur or it is concomitant with metal incorporation. Examination of several chiral permutations of the GGNCC (SEQ ID NO. 1) pentapeptide revealed that none of their corresponding CD spectra match that of the Ni-GGNCC (SEQ ID NO. 1) pentapeptide complex, suggesting the Ni-pentapeptide complex does not undergo chiral inversion. NMR spectroscopy was employed for cross-validation. While the overall NMR spectral features of all five chiral permutations of the GGNCC (SEQ ID NO. 1) pentapeptide are similar, differences in the chemical shift positions and splitting were observed between 2.60 and 3.0 ppm. This region corresponds to the $CH_2$ group on the side chains of the asparagine and cysteine amino acids, which is shifted by the altered configuration of a D-amino acid. While differences are observed in the peptides synthesized to contain D amino acid residues in various positions, the XXLLL-GGNCC (SEQ ID NO. 1) and the nickel-exposed GGNCC (SEQ ID NO. 1) are nearly identical; thus, unlike the tripeptide system, chiral inversion does not occur in the pentapeptide system (FIG. 30).

The Ni-NCC tripeptide complex is not able to bind a fifth ligand, have a measurable redox potential, or exhibit superoxide scavenging activity until site-specific chiral inversion has occurred. In contrast, even immediately after generation, the pentapeptides containing the NCC sequence exhibit all of these features, suggesting open access to the axial position is immediately available. The extension of the sequence from NCC to GGNCC (SEQ ID NO. 1) causes differences in the two peptides. First, the N-terminal amine that participates in binding nickel in the tripeptide is an amide in the pentapeptide. Second, the addition of extra residues can change the dynamics of the peptide and access to the metal center. The difference between bis-amide and amine/amide coordination alters the occurrence of chiral inversion in the pentapeptide system and the electron transfer mechanism, eliminating the primary chiral inversion reaction observed in the tripeptide complex but permitting the second, superoxide scavenging chemistry.

Example 4

Polymerization Reaction-Polymerization of Methacrylate

Figure 31:
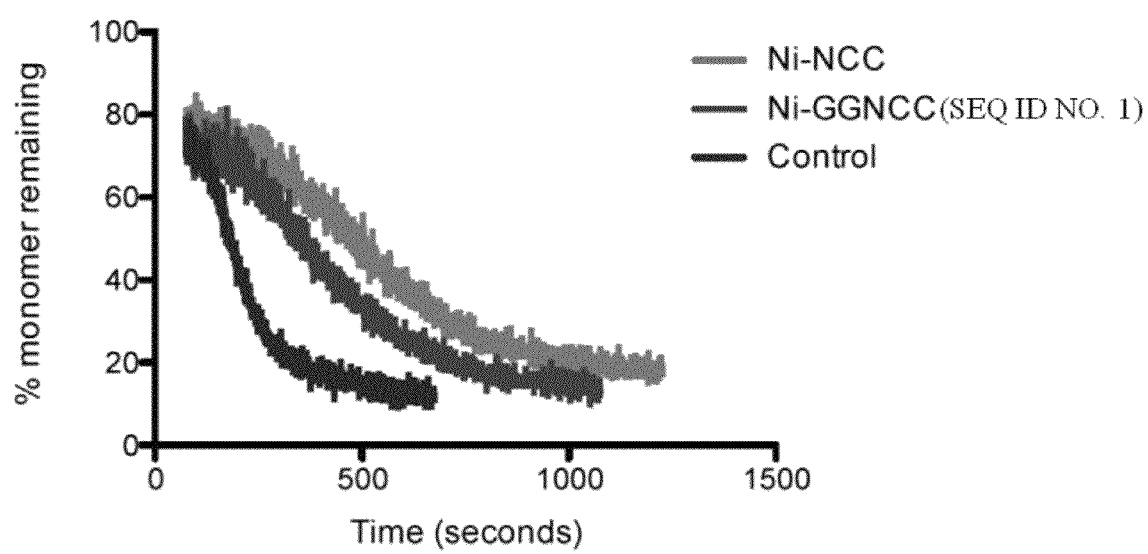
FIG. 31 shows photopolymerization of hydroxy ethyl methacrylic acid (HEMA) initiated using a UV light source for 40 seconds. Addition of the Ni-GGNCC (SEQ ID NO. 1) complex alters the rate of polymerization.

Photopolymerization of hydroxy ethyl methacrylic acid (HEMA) was initiated using a visible light-curing unit (Spectrum® 800, Dentsply, Milford, Del., USA) at an intensity of 550 mW cm-2 for 40 seconds. The subsequent rate of polymerization was measured via FTIR and is reported as a normalized ratio of peak intensities from unreacted and reacted monomer (1455 $cm^{-1}$ and 1673 $cm^{-1}$). The rate of polymerization was altered by the addition of Ni-NCC and Ni-GGNCC (SEQ ID NO. 1). See FIG. 31, illustrating the percentage of polymer remaining over time. Both peptides slowed the rate of polymerization.

EMBODIMENTS

The following non-limiting embodiments provide illustrative examples of the invention, but do not limit the scope of the invention.

Embodiment 1

A method of treating a defect in superoxide dismutase in a subject in need thereof, the method comprising administering to the subject a therapeutically-effective amount of: i) a peptide comprising a sequence $XC_1C_2$, wherein X is any natural or non-natural amino acid or amino acid analog, and further wherein $C_1$ and $C_2$ are each individually chosen from a cysteine and a sulfur-containing alpha or beta amino acid; and ii) a metal bound to the peptide.

Embodiment 2

The method of Embodiment 1, wherein the peptide and the metal are in a unit dosage form, wherein the unit dosage form further comprises a pharmaceutically-acceptable excipient.

Embodiment 3

The method of any one of Embodiments 1 and 2, wherein the sequence $XC_1C_2$ is of all L-amino acids.

Embodiment 4

The method of any one of Embodiments 1 and 2, wherein the sequence $XC_1C_2$ is of an achiral amino acid and two L-amino acids.

Embodiment 5

The method of any one of Embodiments 1 and 2, wherein the sequence $XC_1C_2$ is of an achiral amino acid and two D-amino acids.

Embodiment 6

The method of any one of Embodiments 1-5, wherein the sequence $XC_1C_2$ is included in a sequence $Z_1$—$XC_1C_2$, wherein $Z_1$ is any natural or non-natural amino acid or sequence of natural or non-natural amino acids.

Embodiment 7

The method of any one of Embodiments 1-6, wherein the sequence $XC_1C_2$ is included in a sequence $XC_1C_2$—$Z_2$, wherein $Z_2$ is any natural or non-natural amino acid or sequence of natural or non-natural amino acids.

Embodiment 8

The method of any one of Embodiments 1-7, wherein the sequence $XC_1C_2$ is included in a sequence $Z_1$—$XC_1C_2$—$Z_2$, wherein $Z_1$ and $Z_2$ are each individually any natural or non-natural amino acid or sequence of natural or non-natural amino acids.

Embodiment 9

The method of any one of Embodiments 1-8, wherein the peptide comprises a basic amino acid adjacent to either X or $C_2$.

Embodiment 10

The method of any one of Embodiments 1-9, wherein $C_1$ and $C_2$ are each cysteine.

Embodiment 11

The method of any one of Embodiments 1-10, wherein X is asparagine.

Embodiment 12

The method of any one of Embodiments 1-11, wherein the metal is a group 10 metal.

Embodiment 13

The method of any one of Embodiments 1-12, wherein the metal is nickel.

Embodiment 14

The method of any one of Embodiments 1-13, wherein the composition has a concentration of the peptide and a concentration of the metal, and further wherein the concentration of the peptide and the concentration of the metal are in a ratio from about 1:about 2 to about 2:about 1.

Embodiment 15

The method of Embodiment 15, wherein the ratio is about 1:about 1.

Embodiment 16

The method of any one of Embodiments 1-15, wherein the sequence $XC_1C_2$ binds the metal.

Embodiment 17

The method of any one of Embodiments 1-16, wherein the peptide binds the metal in a square planar orientation.

Embodiment 18

The method of any one of Embodiments 1-16, wherein the peptide binds the metal in a square pyramidal orientation.

Embodiment 19

The method of any one of Embodiments 1-18, wherein the peptide comprises at least 20 amino acids.

Embodiment 20

The method of any one of Embodiments 1-19, wherein the peptide comprises no more than 500 amino acids.

Embodiment 21

The method of any one of Embodiments 1-20, wherein the amount is from about 1 to about 5000 mg.

Embodiment 22

The method of any one of Embodiments 1-21, wherein a complex of the peptide and the metal acts as a preservative.

Embodiment 23

The method of any one of Embodiments 1-22, wherein a complex of the peptide and the metal acts as an antioxidant.

Embodiment 24

The method of any one of Embodiments 1-23, wherein the amount is from about 0.001% to about 0.1% w/v.

Embodiment 25

The method of any one of Embodiments 1-24, wherein the administration is intravenous.

Embodiment 26

A method of reducing pain in a subject in need thereof, the method comprising administering to the subject a therapeutically-effective amount of: i) a peptide comprising a sequence $XC_1C_2$, wherein X is any natural or non-natural amino acid or amino acid analog, and further wherein $C_1$ and $C_2$ are each individually chosen from a cysteine and a sulfur-containing alpha or beta amino acid; and ii) a metal bound to the peptide.

Embodiment 27

The method of Embodiment 26, wherein the peptide and the metal are in a unit dosage form, wherein the unit dosage form further comprises a pharmaceutically-acceptable excipient.

Embodiment 28

The method of any one of Embodiments 26 and 27, wherein the sequence $XC_1C_2$ is of all L-amino acids.

Embodiment 29

The method of any one of Embodiments 26 and 27, wherein the sequence $XC_1C_2$ is of an achiral amino acid and two L-amino acids.

Embodiment 30

The method of any one of Embodiments 26 and 27, wherein the sequence $XC_1C_2$ is of an achiral amino acid and two D-amino acids.

Embodiment 31

The method of any one of Embodiments 26-30, wherein the sequence $XC_1C_2$ is included in a sequence $Z_1$—$XC_1C_2$, wherein $Z_1$ is any natural or non-natural amino acid or sequence of natural or non-natural amino acids.

Embodiment 32

The method of any one of Embodiments 26-31, wherein the sequence $XC_1C_2$ is included in a sequence $XC_1C_2$—$Z_2$, wherein $Z_2$ is any natural or non-natural amino acid or sequence of natural or non-natural amino acids.

Embodiment 33

The method of any one of Embodiments 26-32, wherein the sequence $XC_1C_2$ is included in a sequence $Z_1$—$XC_1C_2$—$Z_2$, wherein $Z_1$ and $Z_2$ are each individually any natural or non-natural amino acid or sequence of natural or non-natural amino acids.

Embodiment 34

The method of any one of Embodiments 26-33, wherein the peptide comprises a basic amino acid adjacent to either X or $C_2$.

Embodiment 35

The method of any one of Embodiments 26-34, wherein $C_1$ and $C_2$ are each cysteine.

Embodiment 36

The method of any one of Embodiment 26-35, wherein X is asparagine.

Embodiment 37

The method of any one of Embodiments 26-36, wherein the metal is a group 10 metal.

Embodiment 38

The method of any one of Embodiments 26-37, wherein the metal is nickel.

Embodiment 39

The method of any one of Embodiments 26-38, wherein the composition has a concentration of the peptide and a concentration of the metal, and further wherein the concentration of the peptide and the concentration of the metal are in a ratio from about 1:about 2 to about 2:about 1.

Embodiment 40

The method of Embodiment 39, wherein the ratio is about 1:about 1.

Embodiment 41

The method of any one of Embodiments 26-40, wherein the sequence $XC_1C_2$ binds the metal.

Embodiment 42

The method of any one of Embodiments 26-41, wherein the peptide binds the metal in a square planar orientation.

Embodiment 43

The method of any one of Embodiments 26-41, wherein the peptide binds the metal in a square pyramidal orientation.

Embodiment 44

The method of any one of Embodiments 26-43, wherein the peptide comprises at least 20 amino acids.

Embodiment 45

The method of any one of Embodiments 26-44, wherein the peptide comprises no more than 500 amino acids.

Embodiment 46

The method of any one of Embodiments 26-45, wherein the amount is from about 1 to about 5000 mg.

Embodiment 47

The method of any one of Embodiments 26-46, wherein a complex of the peptide and the metal acts as a preservative.

Embodiment 48

The method of any one of Embodiments 26-47, wherein a complex of the peptide and the metal acts as an antioxidant.

Embodiment 49

The method of any one of Embodiments 26-48, wherein the amount is from about 0.001% to about 0.1% w/v.

Embodiment 50

The method of any one of Embodiments 26-49, wherein the administration is intravenous.

Embodiment 51

A method of reducing inflammation in a subject in need thereof, the method comprising administering to the subject a therapeutically-effective amount of: i) a peptide comprising a sequence $XC_1C_2$, wherein X is any natural or non-natural amino acid or amino acid analog, and further wherein $C_1$ and $C_2$ are each individually chosen from a cysteine and a sulfur-containing alpha or beta amino acid; and ii) a metal bound to the peptide.

Embodiment 52

The method of Embodiment 51, wherein the peptide and the metal are in a unit dosage form, wherein the unit dosage form further comprises a pharmaceutically-acceptable excipient.

Embodiment 53

The method of any one of Embodiments 51 and 52, wherein the sequence $XC_1C_2$ is of all L-amino acids.

Embodiment 54

The method of any one of Embodiments 51 and 52, wherein the sequence $XC_1C_2$ is of an achiral amino acid and two L-amino acids.

Embodiment 55

The method of any one of Embodiments 51 and 52, wherein the sequence $XC_1C_2$ is of an achiral amino acid and two D-amino acids.

Embodiment 56

The method of any one of Embodiments 51-55, wherein the sequence $XC_1C_2$ is included in a sequence $Z_1$—$XC_1C_2$, wherein $Z_1$ is any natural or non-natural amino acid or sequence of natural or non-natural amino acids.

Embodiment 57

The method of any one of Embodiments 51-56, wherein the sequence $XC_1C_2$ is included in a sequence $XC_1C_2$—$Z_2$, wherein $Z_2$ is any natural or non-natural amino acid or sequence of natural or non-natural amino acids.

Embodiment 58

The method of any one of Embodiments 51-57, wherein the sequence $XC_1C_2$ is included in a sequence $Z_1$—$XC_1C_2$—

$Z_2$, wherein $Z_1$ and $Z_2$ are each individually any natural or non-natural amino acid or sequence of natural or non-natural amino acids.

Embodiment 59

The method of any one of Embodiments 51-58, wherein the peptide comprises a basic amino acid adjacent to either X or $C_2$.

Embodiment 60

The method of any one of Embodiments 51-59, wherein $C_1$ and $C_2$ are each cysteine.

Embodiment 61

The method of any one of Embodiments 51-60, wherein X is asparagine.

Embodiment 62

The method of any one of Embodiments 51-61, wherein the metal is a group 10 metal.

Embodiment 63

The method of any one of Embodiments 51-62, wherein the metal is nickel.

Embodiment 64

The method of any one of Embodiments 51-63, wherein the composition has a concentration of the peptide and a concentration of the metal, and further wherein the concentration of the peptide and the concentration of the metal are in a ratio from about 1:about 2 to about 2:about 1.

Embodiment 65

The method of Embodiment 64, wherein the ratio is about 1:about 1.

Embodiment 66

The method of any one of Embodiments 51-65, wherein the sequence $XC_1C_2$ binds the metal.

Embodiment 67

The method of any one of Embodiments 51-66, wherein the peptide binds the metal in a square planar orientation.

Embodiment 68

The method of any one of Embodiments 51-66, wherein the peptide binds the metal in a square pyramidal orientation.

Embodiment 69

The method of any one of Embodiments 51-68, wherein the peptide comprises at least 20 amino acids.

Embodiment 70

The method of any one of Embodiments 51-69, wherein the peptide comprises no more than 500 amino acids.

Embodiment 71

The method of any one of Embodiments 51-70, wherein the amount is from about 1 to about 5000 mg.

Embodiment 72

The method of any one of Embodiments 51-71, wherein a complex of the peptide and the metal acts as a preservative.

Embodiment 73

The method of any one of Embodiments 51-72, wherein a complex of the peptide and the metal acts as an antioxidant.

Embodiment 74

The method of any one of Embodiments 51-73, wherein the amount is from about 0.001% to about 0.1% w/v.

Embodiment 75

The method of any one of Embodiments 51-74, wherein the administration is intravenous.

Embodiment 76

A method of increasing in-vivo half-life of a therapeutic polypeptide, the method comprising: i) providing a therapeutic polypeptide with an amino terminus, wherein the amino terminus has a sequence $XC_1C_2$, wherein X is any natural or non-natural amino acid or amino acid analog, and further wherein $C_1$ and $C_2$ are each individually chosen from a cysteine and a sulfur-containing alpha or beta amino acid; ii) forming a complex between a metal and the therapeutic polypeptide under conditions suitable for chiral inversion of $C_2$; and iii) separating the metal from the therapeutic polypeptide with chirally inverted $C_2$, wherein the in vivo half-life of the therapeutic polypeptide is increased.

Embodiment 77

The method of Embodiment 76, wherein X is a chiral amino acid, and further wherein X is chirally inverted.

Embodiment 78

The method of any one of Embodiments 76 and 77, wherein $C_2$ has L-stereochemistry prior to chiral inversion.

Embodiment 79

The method of any one of Embodiments 76-78, wherein $C_1$ and $C_2$ are each cysteine.

Embodiment 80

The method of any one of Embodiments 76-79, wherein the metal is a group 10 metal.

Embodiment 81

The method of any one of Embodiments 76-80, wherein the metal is nickel.

Embodiment 82

The method of any one of Embodiments 76-81, wherein the sequence $XC_1C_2$ binds the metal.

Embodiment 83

The method of any one of Embodiments 76-82, wherein the therapeutic polypeptide binds the metal in a square planar orientation.

Embodiment 84

The method of any one of Embodiments 76-82, wherein the therapeutic polypeptide binds the metal in a square pyramidal orientation.

Embodiment 85

The method of any one of Embodiments 76-84, wherein the therapeutic polypeptide comprises at least 20 amino acids.

Embodiment 86

The method of any one of Embodiments 76-85, wherein the therapeutic polypeptide comprises no more than 500 amino acids.

Embodiment 87

The method of any one of Embodiments 76-86, wherein the therapeutic polypeptide adopts a tertiary structure under physiological conditions, wherein a basic amino acid located at least 17 amino acids away from $C_1$ by amino acid sequence is located within 20 angstroms in space from $C_1$.

Embodiment 88

The method of any one of Embodiments 76-87, wherein the therapeutic polypeptide is insulin.

Embodiment 89

The method of any one of Embodiments 76-88, wherein the conditions suitable for chiral inversion comprise exposure to an electron transfer agent.

Embodiment 90

The method of Embodiment 89, wherein the electron transfer agent is molecular oxygen.

Embodiment 91

A method of performing a chemical reaction, the method comprising contacting: i) a peptide comprising a sequence $XC_1C_2$, wherein X is any natural or non-natural amino acid or amino acid analog, wherein $C_1$ and $C_2$ are each individually chosen from a cysteine and a sulfur-containing alpha or beta amino acid, and wherein a metal is bound to the peptide; and ii) chemical starting materials, whereupon the chemical starting materials are combined into a product.

Embodiment 92

The method of Embodiment 91, wherein the peptide is $XC_1C_2$.

Embodiment 93

The method of any one of Embodiments 91 and 92, wherein $C_1$ and $C_2$ are each cysteine.

Embodiment 94

The method of any one of Embodiments 91-93, wherein X is asparagine.

Embodiment 95

The method of any one of Embodiments 91-94, wherein the metal is a group 10 metal.

Embodiment 96

The method of any one of Embodiments 91-95, wherein the metal is nickel.

Embodiment 97

The method of any one of Embodiments 91-96, wherein the sequence $XC_1C_2$ binds the metal.

Embodiment 98

The method of any one of Embodiments 91-97, wherein the peptide binds the metal in a square planar orientation.

Embodiment 99

The method of any one of Embodiments 91-97, wherein the peptide binds the metal in a square pyramidal orientation.

Embodiment 100

The method of any one of Embodiments 91-99, wherein the product comprises at least two chemical starting materials linked by at least one covalent bond.

Embodiment 101

The method of any one of Embodiments 91-100, wherein the chemical reaction is a polymerization reaction.

Embodiment 102

The method of any one of Embodiments 91-101, wherein a complex of the peptide and the metal acts as an initiator.

Embodiment 103

The method of any one of Embodiments 91-101, wherein a complex of the peptide and the metal acts as a radical scavenger.

Embodiment 104

The method of any one of Embodiments 91-103, wherein the peptide has from 3 to about 10 amino acids.

What is claimed is:

1. A method of treating a defect in superoxide dismutase in a subject in need thereof, the method comprising administering to the subject a therapeutically-effective amount of:
   i) a peptide comprising a sequence $XC_1C_2$, wherein X is any natural or non-natural amino acid or amino acid analog, and further wherein $C_1$ and $C_2$ are each individually a sulfur-containing amino acid, wherein the peptide comprises at least 20 amino acids; and
   ii) a metal bound to the peptide.

2. The method of claim 1, wherein the peptide and the metal are in a unit dosage form, wherein the unit dosage form further comprises a pharmaceutically-acceptable excipient.

3. The method of claim 1, wherein the sequence $XC_1C_2$ is of all L-amino acids.

4. The method of claim 1, wherein the sequence $XC_1C_2$ is of an achiral amino acid and two L-amino acids.

5. The method of claim 1, wherein the sequence $XC_1C_2$ is of an achiral amino acid and two D-amino acids.

6. The method of claim 1, wherein the sequence $XC_1C_2$ is included in a sequence $Z_1$—$XC_1C_2$, wherein $Z_1$ is any natural or non-natural amino acid or sequence of natural or non-natural amino acids.

7. The method of claim 1, wherein the sequence $XC_1C_2$ is included in a sequence $XC_1C_2$—$Z_2$, wherein $Z_2$ is any natural or non-natural amino acid or sequence of natural or non-natural amino acids.

8. The method of claim 1, wherein the sequence $XC_1C_2$ is included in a sequence $Z_1$—$XC_1C_2$—$Z_2$, wherein $Z_1$ and $Z_2$ are each individually any natural or non-natural amino acid or sequence of natural or non-natural amino acids.

9. The method of claim 1, wherein the peptide comprises a basic amino acid adjacent to either X or $C_2$.

10. The method of claim 1, wherein $C_1$ and $C_2$ are each cysteine.

11. The method of claim 10, wherein X is asparagine.

12. The method of claim 1, wherein the metal is a group 10 metal.

13. The method of claim 1, wherein the metal is nickel.

14. The method of claim 1, wherein the peptide and the metal are administered to the subject in a composition having a concentration of the peptide and a concentration of the metal, and further wherein the concentration of the peptide and the concentration of the metal are in a ratio from about 1:about 2 to about 2:about 1.

15. The method of claim 14, wherein the ratio is about 1:about 1.

16. The method of claim 1, wherein the sequence $XC_1C_2$ binds the metal.

17. The method of claim 1, wherein the metal is platinum.

18. The method of claim 1, wherein the metal is copper.

19. The method of claim 11, wherein the metal is platinum.

20. The method of claim 11, wherein the metal is copper.

21. The method of claim 1, wherein the peptide comprises no more than 500 amino acids.

22. The method of claim 1, wherein the amount is from about 1 mg to about 50 mg.

23. The method of claim 1, wherein a complex of the peptide and the metal acts as a preservative.

24. The method of claim 1, wherein a complex of the peptide and the metal acts as an antioxidant.

25. The method of claim 1, wherein the amount is from about 0.001% w/v to about 0.1% w/v.

26. The method of claim 1, wherein the administration is intravenous.

27. A method of reducing pain in a subject in need thereof, the method comprising administering to the subject a therapeutically-effective amount of:
   i) a peptide comprising a sequence $XC_1C_2$, wherein X is any natural or non-natural amino acid or amino acid analog, and further wherein $C_1$ and $C_2$ are each individually a sulfur-containing amino acid, wherein the peptide comprises at least 20 amino acids; and
   ii) a metal bound to the peptide.

28. The method of claim 27, wherein the peptide and the metal are in a unit dosage form, wherein the unit dosage form further comprises a pharmaceutically-acceptable excipient.

29. The method of claim 27, wherein the sequence $XC_1C_2$ is of all L-amino acids.

30. The method of claim 27, wherein the sequence $XC_1C_2$ is of an achiral amino acid and two L-amino acids.

31. The method of claim 27, wherein the sequence $XC_1C_2$ is of an achiral amino acid and two D-amino acids.

32. The method of claim 27, wherein the sequence $XC_1C_2$ is included in a sequence $Z_1$—$XC_1C_2$, wherein $Z_1$ is any natural or non-natural amino acid or sequence of natural or non-natural amino acids.

33. The method of claim 27, wherein the sequence $XC_1C_2$ is included in a sequence $XC_1C_2$—$Z_2$, wherein $Z_2$ is any natural or non-natural amino acid or sequence of natural or non-natural amino acids.

34. The method of claim 27, wherein the sequence $XC_1C_2$ is included in a sequence $Z_1$—$XC_1C_2$—$Z_2$, wherein $Z_1$ and $Z_2$ are each individually any natural or non-natural amino acid or sequence of natural or non-natural amino acids.

35. The method of claim 27, wherein the peptide comprises a basic amino acid adjacent to either X or $C_2$.

36. The method of claim 27, wherein $C_1$ and $C_2$ are each cysteine.

37. The method of claim 36, wherein X is asparagine.

38. The method of claim 27, wherein the metal is a group 10 metal.

39. The method of claim 27, wherein the metal is nickel.

40. The method of claim 27, wherein the peptide and the metal are administered to the subject in a composition having a concentration of the peptide and a concentration of the metal, and further wherein the concentration of the peptide and the concentration of the metal are in a ratio from about 1:about 2 to about 2:about 1.

41. The method of claim 40, wherein the ratio is about 1:about 1.

42. The method of claim 27, wherein the sequence $XC_1C_2$ binds the metal.

43. The method of claim 27, wherein the peptide comprises no more than 500 amino acids.

44. The method of claim 27, wherein the amount is from about 1 mg to about 5000 mg.

45. The method of claim 27, wherein a complex of the peptide and the metal acts as a preservative.

46. The method of claim 27, wherein a complex of the peptide and the metal acts as an antioxidant.

47. The method of claim 27, wherein the amount is from about 0.001% w/v to about 0.1% w/v.

48. The method of claim 27, wherein the administration is intravenous.

49. The method of claim 27, wherein the metal is platinum.

50. The method of claim 27, wherein the metal is copper.

51. The method of claim 37, wherein the metal is platinum.

52. The method of claim 37, wherein the metal is copper.

53. A method of reducing inflammation in a subject in need thereof, the method comprising administering to the subject a therapeutically-effective amount of:
i) a peptide comprising a sequence $XC_1C_2$, wherein X is any natural or non-natural amino acid or amino acid analog, and further wherein $C_1$ and $C_2$ are each individually a sulfur-containing amino acid, wherein the peptide comprises at least 20 amino acids; and
ii) a metal bound to the peptide.

54. The method of claim 53, wherein the peptide and the metal are in a unit dosage form, wherein the unit dosage form further comprises a pharmaceutically-acceptable excipient.

55. The method of claim 53, wherein the sequence $XC_1C_2$ is of all L-amino acids.

56. The method of claim 53, wherein the sequence $XC_1C_2$ is of an achiral amino acid and two L-amino acids.

57. The method of claim 53, wherein the sequence $XC_1C_2$ is of an achiral amino acid and two D-amino acids.

58. The method of claim 53, wherein the sequence $XC_1C_2$ is included in a sequence $Z_1$—$XC_1C_2$, wherein $Z_1$ is any natural or non-natural amino acid or sequence of natural or non-natural amino acids.

59. The method of claim 53, wherein the sequence $XC_1C_2$ is included in a sequence $XC_1C_2$—$Z_2$, wherein $Z_2$ is any natural or non-natural amino acid or sequence of natural or non-natural amino acids.

60. The method of claim 53, wherein the sequence $XC_1C_2$ is included in a sequence $Z_1$—$XC_1C_2$—$Z_2$, wherein $Z_1$ and $Z_2$ are each individually any natural or non-natural amino acid or sequence of natural or non-natural amino acids.

61. The method of claim 53, wherein the peptide comprises a basic amino acid adjacent to either X or $C_2$.

62. The method of claim 53, wherein $C_1$ and $C_2$ are each cysteine.

63. The method of claim 62, wherein X is asparagine.

64. The method of claim 53, wherein the metal is a group 10 metal.

65. The method of claim 53, wherein the metal is nickel.

66. The method of claim 53, wherein the peptide and the metal are administered to the subject in a composition having a concentration of the peptide and a concentration of the metal, and further wherein the concentration of the peptide and the concentration of the metal are in a ratio from about 1:about 2 to about 2:about 1.

67. The method of claim 66, wherein the ratio is about 1:about 1.

68. The method of claim 53, wherein the sequence $XC_1C_2$ binds the metal.

69. The method of claim 53, wherein the peptide comprises no more than 500 amino acids.

70. The method of claim 53, wherein the amount is from about 1 mg to about 5000 mg.

71. The method of claim 53, wherein a complex of the peptide and the metal acts as a preservative.

72. The method of claim 53, wherein a complex of the peptide and the metal acts as an antioxidant.

73. The method of claim 53, wherein the amount is from about 0.001% w/v to about 0.1% w/v.

74. The method of claim 53, wherein the administration is intravenous.

75. The method of claim 53, wherein the metal is platinum.

76. The method of claim 53, wherein the metal is copper.

77. The method of claim 63, wherein the metal is platinum.

78. The method of claim 63, wherein the metal is copper.

* * * * *